US011434231B2

(12) United States Patent
Tian et al.

(10) Patent No.: US 11,434,231 B2
(45) Date of Patent: Sep. 6, 2022

(54) SUBSTITUTED IMIDAZOLES FOR THE TREATMENT OF CANCER

(71) Applicant: THE ROYAL INSTITUTION FOR THE ADVANCEMENT OF LEARNING/McGILL UNIVERSITY, Montreal (CA)

(72) Inventors: Xiaohong Tian, Urumqi (CN); Jian Hui Wu, Saint-Laurent (CA); Qianhui Yi, Westmount (CA)

(73) Assignee: THE ROYAL INSTITUTION FOR THE ADVANCEMENT OF LEARN

( * ) Notice: Subject to any disclaimer, the term of this patent is extended or adjusted under 35 U.S.C. 154(b) by 0 days.

(21) Appl. No.: 16/924,157

(22) Filed: Jul. 8, 2020

(65) Prior Publication Data
US 2020/0339554 A1 Oct. 29, 2020

Related U.S. Application Data

(63) Continuation-in-part of application No. 15/746,230, filed as application No. PCT/CA2016/050866 on Jul. 22, 2016, now Pat. No. 10,844,051.

(60) Provisional application No. 62/195,485, filed on Jul. 22, 2015.

(51) Int. Cl.
| | |
|---|---|
| *A61K 31/4178* | (2006.01) |
| *C07D 233/64* | (2006.01) |
| *C07D 413/12* | (2006.01) |
| *C07D 411/14* | (2006.01) |
| *A61K 31/422* | (2006.01) |
| *C07D 403/12* | (2006.01) |
| *C07D 263/32* | (2006.01) |
| *A61K 31/496* | (2006.01) |
| *C07D 413/04* | (2006.01) |
| *A61K 31/454* | (2006.01) |
| *C07D 413/14* | (2006.01) |
| *C07D 401/14* | (2006.01) |
| *A61K 31/5377* | (2006.01) |
| *C07D 401/06* | (2006.01) |
| *C07D 413/06* | (2006.01) |
| *C07D 401/12* | (2006.01) |
| *A61K 45/06* | (2006.01) |

(52) U.S. Cl.
CPC ........ *C07D 413/12* (2013.01); *A61K 31/4178* (2013.01); *A61K 31/422* (2013.01); *A61K 31/454* (2013.01); *A61K 31/496* (2013.01); *A61K 31/5377* (2013.01); *A61K 45/06* (2013.01); *C07D 233/64* (2013.01); *C07D 263/32* (2013.01); *C07D 401/06* (2013.01); *C07D 401/12* (2013.01); *C07D 401/14* (2013.01); *C07D 403/12* (2013.01); *C07D 411/14* (2013.01); *C07D 413/04* (2013.01); *C07D 413/06* (2013.01); *C07D 413/14* (2013.01)

(58) Field of Classification Search
CPC .......................... A61K 31/4178; C07D 233/64
USPC ....................................... 514/397; 548/343.5
See application file for complete search history.

(56) References Cited

PUBLICATIONS

Jordan, V. C. Nature Reviews: Drug Discovery, 2, 2003, 205.*
Vippagunta, et al. Advanced Drug Delivery Reviews, 48, 2001, 18.*
Galons, et al. Synthesis, 12, 1982, 1103-1105.*
Ambrogio et al, KRAS Dimerization Impacts MEK Inhibitor Sensitivity and Oncogenic Activity of Mutant KRAS; Cell 172, 857-868.e1-e7, Feb. 8, 2018.
Bery et al, BRET-Based RAS Biosensors that Show a Novel Small Molecule is an Inhibitor of RAS-Effector Protein-Protein Interactions; eLife, 7:e37122. DOI: https://doi.org/10.7554/eLife.37122, 2018.
Bishop, Colon Cancer Data Key as Pfizer Buys Array; Cancer Discovery, DOI: 10.1158/2159-8290.CD-NB2019-073, 2019.
Boutin et al, Oncogenic Kras Drives Invasion and Maintains Metastases in Colorectal Cancer; Genes & Development 31:370-382 Published by Cold Spring Harbor Laboratory Press, ISSN 0890-9369/17, 2017.
Chen et al, Ras Dimer Formation as a New Signaling Mechanism and Potential Cancer Therapeutic Target; Mini-Reviews in Medicinal Chemistry, 16, 391-403, 2016.
Collins et al, Oncogenic Kras is Required for Both the Initiation and Maintenance of Pancreatic Cancer in Mice; J Clin Invest.,122(2):639-653, 2012.
Collins et al, Kras as a Key Oncogene and Therapeutic Target in Pancreatic Cancer; Frontiers in Physiology, vol. 4, Article 407, 2014.
Cox et al, Drugging the Undruggable RAS: Mission Possible?; Nature Reviews, Drug Discovery, vol. 13, 828-851, 2014.

(Continued)

*Primary Examiner* — Douglas M Willis
(74) *Attorney, Agent, or Firm* — Lavery, De Billy, LLP; Beatrice Ngatcha

(57) ABSTRACT

There are provided compounds, their preparation and their use in the treatment of KRAS-driven cancers. The compounds according to the invention (general formula Class III) disrupt dimerization of KRAS and are inhibitors of KRAS mutants such as KRAS G12D, KRAS G12V and KRAS 12C. Embodiments of the compounds according to the invention are selective inhibitors of KRAS mutants over the wild-type (WT) KRAS.

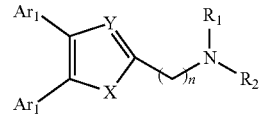

Class III

30 Claims, 8 Drawing Sheets

(56) References Cited

PUBLICATIONS

Cox et al, Targeting RAS Membrane Association: Back to the Future for Anti-RAS Drug Discovery?; American Association for Cancer Research, doi: 10.1158/1078-0432.CCR-14-3214, 2015.

Eser S. et al, Oncogenic KRAS Signalling in Pancreatic Cancer; British Journal of Cancer, 111, 817-822, doi: 10.1038/bjc.2014.215, 2014.

Garrido-Laguna et al., Pancreatic Cancer: From State-of-the-Art Treatments to Promising Novel Therapies; Nat. Rev. Clin. Oncol. 12, 319-334, 2015.

Janes et al, Targeting KRAS Mutant Cancers with a Covalent G12C-Specific Inhibitor; Cell 172, 578-589, 2018.

Jones et al, Specific Mutations in KRAS Codon 12 are Associated with Worse Overall Survival in Patients with Advanced and Recurrent Colorectal Cancer; British Journal of Cancer, 116, 923-929, doi: 10.1038/bjc.2017.37, 2017.

Kanda et al, Presence of Somatic Mutations in Most Early-Stage Pancreatic Intraepithelial Neoplasia; Gastroenterology, 142:730-733, 2012.

Kessler et al, Drugging an Undruggable Pocket on KRAS; PNAS, vol. 116, No. 32,15823-15829, Aug. 6, 2019.

Khvalevskya et al, Mutant KRAS is a Druggable Target for Pancreatic Cancer; PNAS, vol. 110, No. 51, 20723-20728, 2013.

Lito et al, Allele-Specific Inhibitors Inactivate Mutant Kras G12C by a Trapping Mechanism; Science 351 (6273), 604-608, 2016.

McCormick, KRAS as a Therapeutic Target; American Association for Cancer Research, doi: 10.1158/1078-0432.CCR-14-2662, 2015.

Meanwell et al, Nonprostanoid Prostacyclin Mimetics. 2. 4,5-Diphenyloxazole Derivatives; J. Med. Chem., 35, 3483-3497, 1992.

Meanwell et al, Nonprostanoid Prostacyclin Mimetics. 5. Structure-Activity Relationships Associated with [3-[4-(4,5-Diphenyl-2-oxazolyl)-5-oxazolyl]phenoxy]acetic Acid; J. Med. Chem., 36, 3884-3903, 1993.

Morkel et al., Similar but Different: Distinct Roles for KRAS and BRAF Oncogenes in Colorectal Cancer Development and Therapy Resistance; Oncotarget, vol. 6, No. 25, 2015.

Nussinov et al., Is Nanoclustering Essential for All Oncogenic KRas Pathways? Can it Explain Why Wild-Type KRas Can Inhibit its Oncogenic Variant?; Seminars in Cancer Biology 54, 114-120, 2019.

Ostrem et al, K-Ras(G12C) Inhibitors Allosterically Control GTP Affinity and Effector Interactions; Nature, vol. 503, doi:10.1038/nature12796, 2013.

Patricelli et al., Selective Inhibition of Oncogenic KRAS Output with Small Molecules Targeting the Inactive State; American Association for Cancer Research, DOI: 10.1158/2159-8290, 2016.

Ryan et al., Pancreatic Adenocarcinoma; N Engl J Med, 371:1039-49, DOI: 10.1056/NEJMra1404198, 2014.

Samatar et al, Targeting RAS-ERK Signalling in Cancer: Promises and Challenges; Nature Reviews, Drug Discovery, vol. 13, 928-941, 2014.

Spencer-Smith et al, Inhibition of RAS Function Through Targeting an Allosteric Regulatory Site; Nature chemical biology, vol. 13, 62-68, 2017.

Zhou et al, The Role of Wild Type RAS Isoforms in Cancer; Seminars in Cell & Developmental Biology 58, 60-69, 2016.

* cited by examiner

SUBSTITUTED IMIDAZOLES FOR THE TREATMENT OF CANCER

CROSS-REFERENCE TO RELATED APPLICATIONS FIELD OF THE INVENTION

This application is a continuation-in-part application of U.S. patent application Ser. No. 15/746,230 filed on Jul. 22, 2016, and is a National Entry Application of PCT application Serial No. PCT/CA2016/050866 filed on Jul. 22, 2016, which itself claims benefit of U.S. provisional application Ser. No. U.S. 62/195,485 filed on Jul. 22, 2015. All the documents above are incorporated herein in their entirety by reference

FIELD OF THE INVENTION

The invention relates generally to compounds, their preparation and their use in the treatment of KRAS-driven cancers. More specifically, the compounds of the invention disrupt dimerization of KRAS and are inhibitors of KRAS, including KRAS G12D, KRAS G12V and KRAS 12C mutants. Embodiments of the compounds of the invention are selective inhibitors of KRAS mutants over the wild-type (WT) KRAS.

BACKGROUND OF THE INVENTION

Oncogenic KRAS is a key driver of three lethal cancers: pancreatic cancer (>90% of cases), colon cancer (~50%) and lung cancer (~25%). Within these cancers, specific KRAS mutations dominate. KRAS G12D and KRAS G12V are the first and second common mutations in both of the pancreatic and colorectal cancers, while KRAS G12C is most common in lung cancer.[1] Oncogenic KRAS is mutationally activated in >90% pancreatic ductal adenocarcinoma (PDAC) patients. Out of all of the KRAS mutations in PDAC, the predominant substitution is G12D (51%), followed by G12V (30%).[1] To date, accumulated in vitro and in vivo studies have firmly established that oncogenic mutant KRAS signaling is a driver of pancreatic cancer initiation, progression and maintenance, indicating KRAS mutants could be a critical drug target for PDAC.[2-6] However, there is no KRAS 12D or 12V-targeting therapeutics available in the clinics. The overall 5-year survival rate of PDAC is <5%.[7-9] This burning scenario, where KRAS mutant is an attractive drug target but there is no effective treatment available, is also played in colorectal cancer (CRC).[10,11] In the past three decades, tremendous efforts and resources have been directed towards development of inhibitors of oncogenic KRAS signaling, but only in recent years, a breakthrough was made for the inhibitors of KRAS G12C mutant (KRAS[12C]).[12,13] Phase I clinical trials of KRAS[12C]-specific inhibitor AMG-510 indicated that it has clinical efficacy in lung cancer patients with tumors that harbor KRAS[12C] mutant.[14] This has provided a proof of principle, demonstrating KRAS mutant is druggable after all. However, these KRAS[12C] mutant inhibitors are inactive against the KRAS 12D or 12V mutants as these compounds need to form a covalent bond with cysteine at residue 12. A current challenge in the field is how to develop selective inhibitors for the more prevalent KRAS G12D and G12V mutants.

Key molecular requirements for KRAS signaling include membrane-anchoring, GTP loading and engagement with effectors.[1] As the first major attempt to inhibit RAS, farnesyl protein transferase inhibitors were developed to alter RAS membrane localization, but failed in the treatment of RAS-dependent cancers in clinical trials because of a compensatory prenylation of RAS.[15] Engagement of KRAS with effector proteins that transmit signals downstream is another key requirement for KRAS signaling. Such engagement is done via protein-protein interactions that involve the switch I region (residues 30-38) and switch II region (residues 60-76) in the effector lobe of KRAS. At least six RAS effector families contribute to RAS-dependent cancer initiation and/or maintenance, including the RAF-MEK-ERK, PI3K-AKT-mTOR and RALGDS-RAL pathways.[1,5] After the failure of RAS membrane-anchoring inhibitors, effort to target KRAS signaling has shifted to development of the inhibitors of KRAS downstream effector pathways, especially the RAF-MEK-ERK and the PI3K-AKT pathways.[1,16] So far, these efforts have been generally disappointing due to the engagement of highly complex and dynamic signaling network downstream of oncogenic KRAS, which can adapt and rewire in response to these downstream inhibitors.[1] In addition, a RAS pan-inhibitor called BI-2852 was recently discovered.[17] BI-2852 inhibits all of the WT and mutants of KRAS, NRAS and HRAS, and shows antiproliferative effect in H358 lung cancer cells.[17] However, as accumulated studies indicated that wild-type (WT) KRAS could act as a tumor suppressor for mutant KRAS,[18,19] it is highly desirable to develop selective inhibitors of KRAS mutants that spare the WT KRAS.

Recent studies revealed that dimerization of KRAS/ KRAS, like the dimerization of its effector RAF, is another key molecular requirement for activation of KRAS signaling.[20] Existence and physiological relevance of KRAS dimers is a critical but previously unappreciated aspect of KRAS biology. To date, KRAS dimerization was detected by cell-based fluorescence resonance energy transfer (FRET)[21] and bioluminescence resonance energy transfer (BRET) experiments.[22] Furthermore, it was demonstrated that dimerization is critical for the oncogenic potential of the KRAS G12D, G12V and G12C mutants in vitro and in xenograft tumors.[21] These studies revealed that disruption of KRAS dimerization could be an effective approach to inhibit KRAS signaling.

Accordingly, as indicated above, there is a need to develop chemical compounds that selectively inhibit KRAS G12D and KRAS G12V mutants. Also, there is a need to develop compounds that disrupt KRAS dimerization.

SUMMARY OF THE INVENTION

The inventors have designed and prepared novel chemical compounds. The compounds according to the invention may be used in the treatment of KRAS-driven cancers such as pancreatic cancer, colorectal cancer and lung cancer. The compounds of the invention disrupt dimerization of KRAS and are inhibitors of KRAS, including KRAS G12D, KRAS G12V and KRAS 12C mutants. Embodiments of the compounds of the invention are selective inhibitors of KRAS mutants over the wild-type (WT) KRAS.

Other objects, advantages and features of the present invention will become more apparent upon reading of the following non-restrictive description of specific aspects and embodiments thereof, given by way of example only with reference to the accompanying drawings.

DESCRIPTION OF ILLUSTRATIVE EMBODIMENTS

Figure 1:
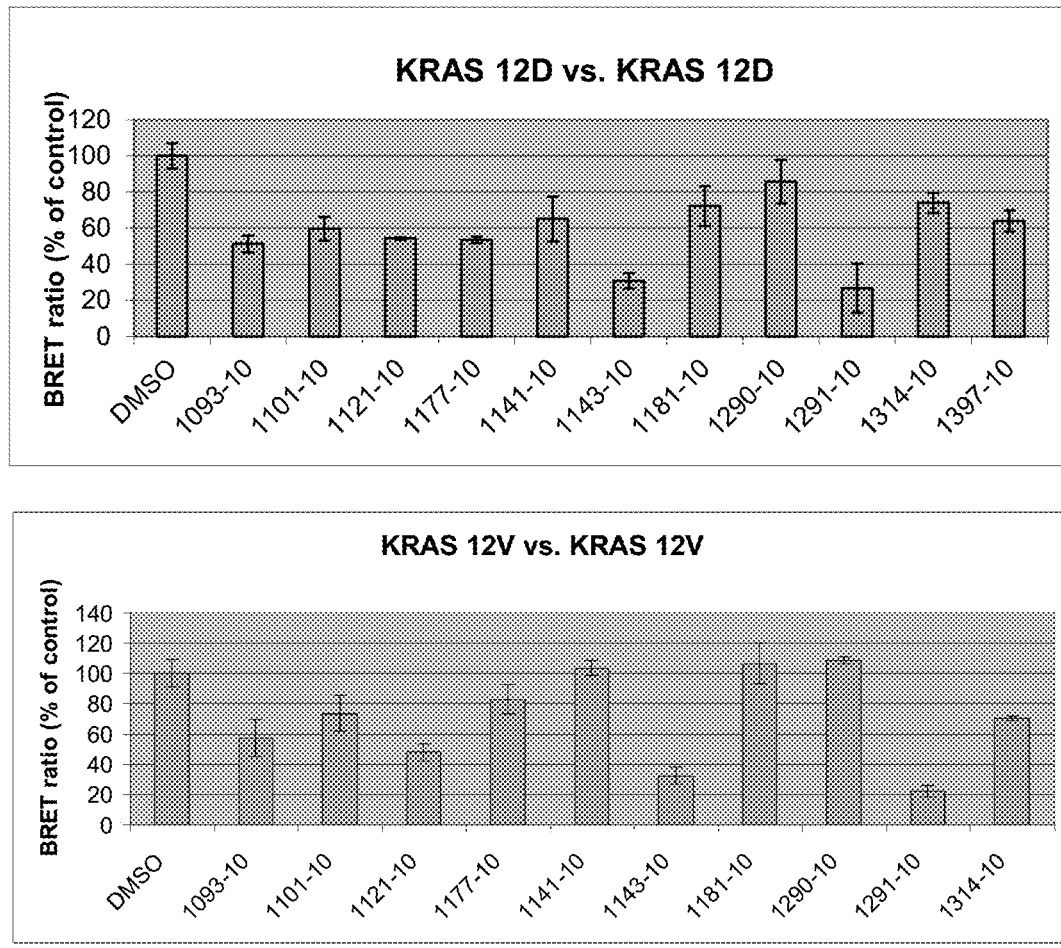
FIG. 1: Activity of compounds 1093, 1101, 1121, 1177, 1141, 1143, 1181, 1290, 1291, 1314 and 1397 on dimerization of KRAS 12D, KRAS 12V, KRAS wild-type (WT) or KRAS 12C, as assessed by BRET2 assays in HEK293 cells. Experimental details are described herein below. Cells were exposed to DMSO vehicle or the compound at designated doses (μM) for 24 hours. For WT KRAS assay, EGF (10 ng/mL) was added 30 minutes before adding DeepBlue C.
Figure 1:
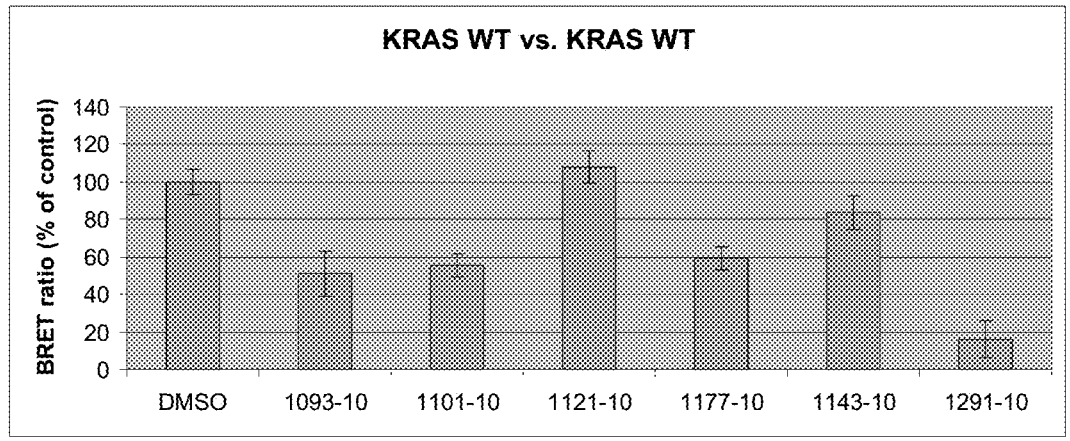
Figure 1:
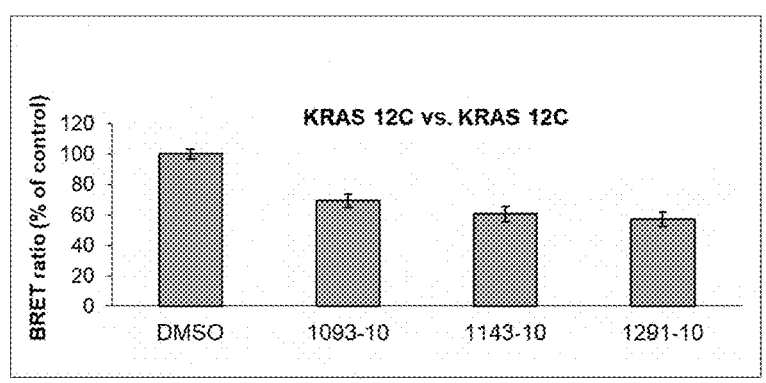

Before the present invention is further described, it is to be understood that the invention is not limited to the particular embodiments described below, as variations of these embodiments may be made and still fall within the scope of the appended claims. It is also to be understood that the terminology employed is for the purpose of describing particular embodiments; and is not intended to be limiting. Instead, the scope of the present invention will be established by the appended claims.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

As used herein, the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used herein, term "alkyl" or "alk" represents a monovalent group derived from a straight or branched chain saturated hydrocarbon comprising, unless otherwise specified, from 1 to 15 carbon atoms and is exemplified by methyl, ethyl, n- and iso-propyl, n-, sec-, iso- and tert-butyl, neopentyl and the like and may be optionally substituted with one, two, three or, in the case of alkyl groups comprising two carbons or more, four substituents independently selected from the group consisting of: (1) alkoxy of one to six carbon atoms; (2) alkylsulfinyl of one to six carbon atoms; (3) alkylsulfonyl of one to six carbon atoms; (4) alkynyl of two to six carbon atoms; (5) amino; (6) aryl; (7) arylalkoxy, where the alkylene group comprises one to six carbon atoms; (8) azido; (9) cycloalkyl of three to eight carbon atoms; (10) halo; (11) heterocyclyl; (12) (heterocycle)oxy; (13) (heterocycle)oyl; (14) hydroxyl; (15) hydroxyalkyl of one to six carbon atoms; (16) N-protected amino; (17) nitro; (18) oxo or thiooxo; (19) perfluoroalkyl of 1 to 4 carbon atoms; (20) perfluoroalkoxyl of 1 to 4 carbon atoms; (21) spiroalkyl of three to eight carbon atoms; (22) thioalkoxy of one to six carbon atoms; (23) thiol; (24) OC(O)$R^A$, where $R^A$ is selected from the group consisting of (a) substituted or unsubstituted $C_{1-6}$ alkyl, (b) substituted or unsubstituted $C_6$ or $C_{10}$ aryl, (c) substituted or unsubstituted $C_{7-16}$ arylalkyl, where the alkylene group comprises one to six carbon atoms, (d) substituted or unsubstituted $C_{1-9}$ heterocyclyl, and (e) substituted or unsubstituted $C_{2-15}$ heterocyclylalkyl, where the alkylene group comprises one to six carbon atoms; (25) $C(O)R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (26) $CO_2R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (27) $C(O)NR^CR^D$, where each of $R^C$ and $R^D$ is independently selected from the group consisting of (a) hydrogen, (b) alkyl, (c) aryl and (d) arylalkyl, where the alkylene group comprises one to six carbon atoms; (28) $S(O)R^E$, where $R^E$ is selected from the group consisting of (a) alkyl, (b) aryl, (c) arylalkyl, where the alkylene group comprises one to six carbon atoms, and (d) hydroxyl; (29) $S(O)_2R^E$, where $R^E$ is selected from the group consisting of (a) alkyl, (b) aryl, (c) arylalkyl, where the alkylene group comprises one to six carbon atoms, and (d) hydroxyl; (30) $S(O)_2NR^FR^G$, where each of $R^F$ and $R^G$ is independently selected from the group consisting of (a) hydrogen, (b) alkyl, (c) aryl and (d) arylalkyl, where the alkylene group comprises one to six carbon atoms; and (31) —$NR^HR^I$, where each of $R^H$ and $R^I$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, (i) alkcycloalkyl, where the cycloalkyl group comprises three to eight carbon atoms, and the alkylene group comprises one to ten carbon atoms, (j) alkanoyl of one to six carbon atoms, (k) aryloyl of 6 to 10 carbon atoms, (l) alkylsulfonyl of one to six carbon atoms, and (m) arylsulfonyl of 6 to 10 carbons atoms, with the proviso that no two groups are bound to the nitrogen atom through a carbonyl group or a sulfonyl group.

The terms "alkoxy" or "alkyloxy" as used interchangeably herein, represent an alkyl group attached to the parent molecular group through an oxygen atom.

The term "alkylthio" or "thioalkoxy" as used interchangeably herein, represents an alkyl group attached to the parent molecular group through a sulfur atom.

The term "alkylene" as used herein, represents a saturated divalent hydrocarbon group derived from a straight or branched chain saturated hydrocarbon by the removal of two hydrogen atoms, and is exemplified by methylene, ethylene, isopropylene and the like.

The term "alkenyl" as used herein, represents monovalent straight or branched chain groups of, unless otherwise specified, from 2 to 15 carbons, such as, for example, 2 to 6 carbon atoms or 2 to 4 carbon atoms, containing one or more carbon-carbon double bonds and is exemplified by ethenyl, 1-propenyl, 2-propenyl, 2-methyl-1-propenyl, 1-butenyl, 2-butenyl and the like and may be optionally substituted with one, two, three or four substituents independently selected from the group consisting of: (1) alkoxy of one to six carbon atoms; (2) alkylsulfinyl of one to six carbon atoms; (3) alkylsulfonyl of one to six carbon atoms; (4) alkynyl of two to six carbon atoms; (5) amino; (6) aryl; (7) arylalkoxy, where the alkylene group comprises one to six carbon atoms; (8) azido; (9) cycloalkyl of three to eight carbon atoms; (10) halo; (11) heterocyclyl; (12) (heterocycle)oxy; (13) (heterocycle)oyl; (14) hydroxyl; (15) hydroxyalkyl of one to six carbon atoms; (16) N-protected amino; (17) nitro; (18) oxo or thiooxo; (19) perfluoroalkyl of 1 to 4 carbon atoms; (20) perfluoroalkoxyl of 1 to 4 carbon atoms; (21) spiroalkyl of three to eight carbon atoms; (22) thioalkoxy of one to six carbon atoms; (23) thiol; (24) $OC(O)R^A$, where $R^A$ is selected from the group consisting of (a) substituted or unsubstituted $C_{1-6}$ alkyl, (b) substituted or unsubstituted $C_6$ or $C_{10}$ aryl, (c) substituted or unsubstituted $C_{7-16}$ arylalkyl, where the alkylene group comprises one to six carbon atoms, (d) substituted or unsubstituted $C_{1-9}$ heterocyclyl, and (e) substituted or unsubstituted $C_{2-15}$ heterocyclylalkyl, where the alkylene group comprises one to six carbon atoms; (25) $C(O)R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (26) $CO_2R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (27) $C(O)NR^CR^D$, where each of $R^C$ and $R^D$ is independently selected from the group consisting of (a) hydrogen, (b) alkyl, (c) aryl and (d) arylalkyl, where the alkylene group comprises one to six carbon atoms; (28) $S(O)R^E$, where $R^E$ is selected from the group consisting of (a) alkyl, (b) aryl, (c) arylalkyl, where the alkylene group comprises one to six carbon atoms, and (d) hydroxyl; (29) $S(O)2R^E$, where $R^E$ is selected from the group consisting of (a) alkyl, (b) aryl, (c) arylalkyl, where the alkylene group comprises one to six carbon atoms, and (d) hydroxyl; (30) $S(O)_2NR^FR^G$, where each of $R^F$ and $R^G$ is independently selected from the group consisting of (a) hydrogen, (b) alkyl, (c) aryl and (d) arylalkyl, where the alkylene group comprises one to six carbon atoms; and (31) —$NR^HR^I$, where each of $R^H$ and $R^I$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms; (i) alkcycloalkyl, where the cycloalkyl group comprises three to eight carbon atoms, and the alkylene group comprises one to ten carbon atoms, (j) alkanoyl of one to six carbon atoms, (k) aryloyl of 6 to 10 carbon atoms, (l) alkylsulfonyl of one to six carbon atoms, and (m) arylsulfonyl of 6 to 10 carbons atoms, with the proviso that no two groups are bound to the nitrogen atom through a carbonyl group or a sulfonyl group.

The term "alkynyl" as used herein, represents monovalent straight or branched chain groups of from two to six carbon atoms comprising a carbon-carbon triple bond and is exemplified by ethynyl, 1-propynyl, and the like and may be optionally substituted with one, two, three or four substituents independently selected from the group consisting of: (1) alkoxy of one to six carbon atoms; (2) alkylsulfinyl of one to six carbon atoms; (3) alkylsulfonyl of one to six carbon atoms; (4) alkynyl of two to six carbon atoms; (5) amino; (6) aryl; (7) arylalkoxy, where the alkylene group comprises one to six carbon atoms; (8) azido; (9) cycloalkyl of three to eight carbon atoms; (10) halo; (11) heterocyclyl; (12) (heterocycle)oxy; (13) (heterocycle)oyl; (14) hydroxyl; (15) hydroxyalkyl of one to six carbon atoms; (16) N-protected amino; (17) nitro; (18) oxo or thiooxo; (19) perfluoroalkyl of 1 to 4 carbon atoms; (20) perfluoroalkoxyl of 1 to 4 carbon atoms; (21) spiroalkyl of three to eight carbon atoms; (22) thioalkoxy of one to six carbon atoms; (23) thiol; (24) OC(O)R$^A$, where R$^A$ is selected from the group consisting of (a) substituted or unsubstituted C$_{1-6}$ alkyl, (b) substituted or unsubstituted C$_6$ or C$_{10}$ aryl, (c) substituted or unsubstituted C$_{7-16}$ arylalkyl, where the alkylene group comprises one to six carbon atoms, (d) substituted or unsubstituted C$_{1-9}$ heterocyclyl, and (e) substituted or unsubstituted C$_{2-15}$ heterocyclylalkyl, where the alkylene group comprises one to six carbon atoms; (25) C(O)R$^B$, where R$^B$ is selected from the group consisting of (a) hydrogen, (b) substituted or unsubstituted C$_{1-6}$ alkyl, (c) substituted or unsubstituted C$_6$ or C$_{10}$ aryl, (d) substituted or unsubstituted C$_{7-16}$ arylalkyl, where the alkylene group comprises one to six carbon atoms, (e) substituted or unsubstituted C$_{1-9}$ heterocyclyl, and (f) substituted or unsubstituted C$_{2-15}$ heterocyclylalkyl, where the alkylene group comprises one to six carbon atoms; (26) CO$_2$R$^B$, where R$^B$ is selected from the group consisting of (a) hydrogen, (b) substituted or unsubstituted C$_{1-6}$ alkyl, (c) substituted or unsubstituted C$_6$ or C$_{10}$ aryl, (d) substituted or unsubstituted C$_{7-16}$ arylalkyl, where the alkylene group comprises one to six carbon atoms, (e) substituted or unsubstituted C$_{1-9}$ heterocyclyl, and (f) substituted or unsubstituted C$_{2-15}$ heterocyclylalkyl, where the alkylene group comprises one to six carbon atoms; (27) C(O)NR$^C$R$^D$, where each of R$^C$ and R$^D$ is independently selected from the group consisting of (a) hydrogen, (b) alkyl, (c) aryl and (d) arylalkyl, where the alkylene group comprises one to six carbon atoms; (28) S(O)R$^E$, where R$^E$ is selected from the group consisting of (a) alkyl, (b) aryl, (c) arylalkyl, where the alkylene group comprises one to six carbon atoms, and (d) hydroxyl; (29) S(O)2R$^E$, where R$^E$ is selected from the group consisting of (a) alkyl, (b) aryl, (c) arylalkyl, where the alkylene group comprises one to six carbon atoms, and (d) hydroxyl; (30) S(O)$_2$NR$^F$R$^G$, where each of R$^F$ and R$^G$ is independently selected from the group consisting of (a) hydrogen, (b) alkyl, (c) aryl and (d) arylalkyl, where the alkylene group comprises one to six carbon atoms; and (31) —NR$^H$R$^I$, where each of R$^H$ and R$^I$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, (i) alkcycloalkyl, where the cycloalkyl group comprises three to eight carbon atoms, and the alkylene group comprises one to ten carbon atoms, (j) alkanoyl of one to six carbon atoms, (k) aryloyl of 6 to 10 carbon atoms, (l) alkylsulfonyl of one to six carbon atoms, and (m) arylsulfonyl of 6 to 10 carbons atoms, with the proviso that no two groups are bound to the nitrogen atom through a carbonyl group or a sulfonyl group.

The term "aryl" as used herein, represents mono- and/or bicyclic carbocyclic ring systems and/or multiple rings fused together and is exemplified by phenyl, naphthyl, 1,2-dihydronaphthyl, 1,2,3,4-tetrahydronaphthyl, fluorenyl, indanyl, indenyl and the like and may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups independently comprise from one to six carbon atoms; (5) alkylsulfinyl of one to six carbon atoms; (6) alkylsulfinylalkyl, where the alkyl and alkylene groups independently comprise from one to six carbon atoms; (7) alkylsulfonyl of one to six carbon atoms; (8) alkylsulfonylalkyl, where the alkyl and alkylene groups are independently comprised of one to six carbon atoms; (9) aryl; (10) arylalkyl, where the alkyl group comprises one to six carbon atoms; (11) amino; (12) aminoalkyl of one to six carbon atoms; (13) aryl; (14) arylalkyl, where the alkylene group comprises one to six carbon atoms; (15) aryloyl; (16) azido; (17) azidoalkyl of one to six carbon atoms; (18) carboxaldehyde; (19) (carboxaldehyde)alkyl, where the alkylene group comprises one to six carbon atoms; (20) cycloalkyl of three to eight carbon atoms; (21) alkcycloalkyl, where the cycloalkyl group comprises three to eight carbon atoms and the alkylene group comprises one to ten carbon atoms; (22) halo; (23) haloalkyl of one to six carbon atoms; (24) heterocyclyl; (25) (heterocyclyl)oxy; (26) (heterocyclyl)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, where the alkylene group comprises one to six carbon atoms; (33) oxo; (34) thioalkoxy of one to six carbon atoms; (35) thioalkoxyalkyl, where the alkyl and alkylene groups independently comprise from one to six carbon atoms; (36) (CH$_2$)$_q$CO$_2$R$^A$, where q is an integer ranging from zero to four and R$^A$ is selected from the group consisting of (a) alkyl, (b) aryl, and (c) arylalkyl, where the alkylene group comprises one to six carbon atoms; (37) (CH$_2$)$_q$C(O)NR$^B$R$^C$, where R$^B$ and R$^C$ are independently selected from the group consisting of (a) hydrogen, (b) alkyl, (c) aryl, and (d) arylalkyl, where the alkylene group comprises one to six carbon atoms; (38) (CH$_2$)$_q$S(O)$_2$R$^D$, where R$^D$ is selected from the group consisting of (a) alkyl, (b) aryl, and (c) arylalkyl, where the alkylene group comprises one to six carbon atoms; (39) (CH$_2$)$_q$S(O)$_2$NR$^E$R$^F$, where each of R$^E$ and R$^F$ is independently selected from the group consisting of (a) hydrogen, (b) alkyl, (c) aryl, and (d) arylalkyl, where the alkylene group comprises one to six carbon atoms; (40) (CH$_2$)$_q$NR$^G$R$^H$, where each of R$^G$ and R$^H$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, and (i) alkcycloalkyl, where the cycloalkyl group comprises three to eight carbon atoms, and the alkylene group comprises one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

As used herein, the term "alkylaryl" represents an aryl group attached to the parent molecular group through an alkyl group.

The term "cycloalkyl" as used herein, represents a monovalent saturated or unsaturated non-aromatic cyclic hydrocarbon group of three to eight carbon atoms, unless otherwise specified, and is exemplified by cyclopropyl, cyclobutyl, cyclopentyl, cyclohexyl, cycloheptyl, bicyclo [2.2.1]heptyl and the like. The cycloalkyl groups of the present disclosure can be optionally substituted with: (1) alkanoyl of one to six carbon atoms; (2) alkyl of one to six carbon atoms; (3) alkoxy of one to six carbon atoms; (4) alkoxyalkyl, where the alkyl and alkylene groups independently comprise from one to six carbon atoms; (5) alkylsulfinyl of one to six carbon atoms; (6) alkylsulfinylalkyl, where the alkyl and alkylene groups independently comprise from one to six carbon atoms; (7) alkylsulfonyl of one to six carbon atoms; (8) alkylsulfonylalkyl, where the alkyl and alkylene groups independently comprise from one to six carbon atoms; (9) aryl; (10) arylalkyl, where the alkyl group comprises one to six carbon atoms; (11) amino; (12) aminoalkyl of one to six carbon atoms; (13) aryl; (14) arylalkyl, where the alkylene group comprises one to six carbon atoms; (15) aryloyl; (16) azido; (17) azidoalkyl of one to six carbon atoms; (18) carboxaldehyde; (19) (carboxaldehyde)alkyl, where the alkylene group comprises one to six carbon atoms; (20) cycloalkyl of three to eight carbon atoms; (21) alkcycloalkyl, where the cycloalkyl group comprises three to eight carbon atoms and the alkylene group comprises one to ten carbon atoms; (22) halo; (23) haloalkyl of one to six carbon atoms; (24) heterocyclyl; (25) (heterocyclyl)oxy; (26) (heterocyclyl)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, where the alkylene group comprises one to six carbon atoms; (33) oxo; (34) thioalkoxy of one to six carbon atoms; (35) thioalkoxyalkyl, where the alkyl and alkylene groups independently comprise from one to six carbon atoms; (36) $(CH_2)_qCO_2R^A$, where q is an integer ranging from zero to four and $R^A$ is selected from the group consisting of (a) alkyl, (b) aryl, and (c) arylalkyl, where the alkylene group comprises one to six carbon atoms; (37) $(CH_2)_qC(O)NR^BR^C$, where each of $R^B$ and $R^C$ is independently selected from the group consisting of (a) hydrogen, (b) alkyl, (c) aryl, and (d) arylalkyl, where the alkylene group comprises one to six carbon atoms; (38) $(CH_2)_q S(O)_2R^D$, where $R^D$ is selected from the group consisting of (a) alkyl, (b) aryl, and (c) arylalkyl, where the alkylene group comprises one to six carbon atoms; (39) $(CH_2)_q S(O)_2NR^ER^F$, where each of $R^E$ and $R^F$ is independently, selected from the group consisting of (a) hydrogen, (b) alkyl, (c) aryl, and (d) arylalkyl, where the alkylene group comprises one to six carbon atoms; (40) $(CH_2)_q NR^GR^H$, where each of $R^G$ and $R^H$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms and (i) alkcycloalkyl, where the cycloalkyl group comprises three to eight carbon atoms, and the alkylene group comprises one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The term "halogen" or "halo" as used interchangeably herein, represents F, Cl, Br and I.

The term "heteroatom" as used herein, is understood as being oxygen, sulfur or nitrogen.

The term "carbonyl" as used herein, represents a C(O) group, which can also be represented as C=O.

The terms "acyl" or "alkanoyl" as used interchangeably herein, represent an alkyl group, as defined herein, or hydrogen attached to the parent molecular group through a carbonyl group, as defined herein, and is exemplified by formyl, acetyl, propionyl, butanoyl and the like. Exemplary unsubstituted acyl groups comprise from 2 to 10 carbons.

The term "analogue" as used herein, is understood as being a substance similar in structure to another compound but differing in some slight structural detail.

The term "salt(s)" as used herein, is understood as being acidic and/or basic salts formed with inorganic and/or organic acids or bases. Zwitterions (internal or inner salts) are understood as being included within the term "salt(s)" as used herein, as are quaternary ammonium salts such as alkylammonium salts. Nontoxic, pharmaceutically acceptable salts are preferred, although other salts may be useful, as for example in isolation or purification steps. Examples of acid addition salts include but are not limited to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, phosphoric, 2-hydroxyethanesulfonate, lactate, maleate, mandelate, methanesulfonate, 2-naphthalenesulfonate, nicotinate, oxalate, pectinate, persulfate, 3-phenylpropionate, picrate, pivalate, propionate, succinate, tartrate, thiocyanate, tosylate, and undecanoate. Examples of base addition salts include but are not limited to alkali metal salts and alkaline earth metal salts. Non limiting examples of alkali metal salts include lithium, sodium and potassium salts. Non-limiting examples of alkaline earth metal salts include magnesium and calcium salts.

The inventors have designed and prepared novel chemical compounds. The compounds according to the invention may be used in the treatment of KRAS-driven cancers such as pancreatic cancer, colorectal cancer and lung cancer. The compounds of the invention disrupt dimerization of KRAS and are inhibitors of KRAS, including KRAS G12D, KRAS G12V and KRAS 12C mutants. Embodiments of the compounds of the invention are selective inhibitors of KRAS mutants over the wild-type (WT) KRAS.

According to an aspect, the compounds of the invention may be used in a pharmaceutical composition which also comprises a pharmaceutically acceptable carrier.

According to yet another aspect, the invention provides for a method of treating a medical condition that involves a KRAS mutant. The method comprises administering to a subject a therapeutically effective amount of a compound of the invention or a therapeutically effective amount of a pharmaceutical composition of the invention.

Other aspects of the invention comprise treating the subject with a second cancer therapy. The compound or the pharmaceutical composition of the invention may be administered orally, intravenously, intra-arterially, subcutaneously, topically or intramuscularly, intraocularly, intranasaly or transdermaly. The subject may be human or a non-human animal.

The present invention is illustrated in further details below. It should be noted that the examples outlined are non-limiting examples.

Chemistry

Compounds according to embodiments of the invention have a general formula "Class III" illustrated below.

Class III

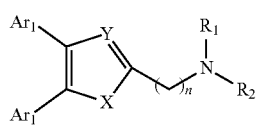

wherein:

Ar$_1$ and Ar$_2$ are each independently selected from a mono or bicyclic carbocyclic ring system or a multiple ring system wherein the rings are fused together, optionally, the ring comprises one or more heteroatom which are the same or different, also optionally, the ring is substituted with a substituent selected from alkyl, cycloalkyl alkoxy, alkoxy, thioalkoxy, aryl, aryloxy, thioaryloxy, alkyaryloxy, thioalkylaryloxy, OH, SH, NH$_2$, a halogen atom, a halogeno alkyl, a halogeno alkoxy, a halogeno thioalkoxy, CN, NO$_2$, S(=O)$_2$, S(=O)$_2$R$^1$, where R$^1$ is selected from alkyl, cycloalkyl and aryl;

X and Y are each independently selected from O, S, S(=O)$_2$, Se(=O)$_2$, C, N and NR wherein R is selected from H, S(=O)$_2$R$^1$, S(=O)$_2$NR$^1$R$^2$, COR$^1$, Se(=O)$_2$R$^1$, alkyl, cycloalkyl, alkene, alkyne, aryl, alkylaryl, a 5 to 8-member ring comprising one or more heteroatom which are the same or different; optionally, the ring comprises one or more heteroatom which are the same or different, also optionally, the ring is substituted with substituents selected from alkyl, alkene, alkyne, aryl, acyl, CF$_3$, CH$_2$CF$_3$, OH, OCH$_3$, OC$_2$H$_5$, OCF$_3$, SH, SCH$_3$, NH$_2$, a halogen atom, CN, CH$_2$CN, (CH$_2$)$_n$CN (n=1-15), NO$_2$, S(=O)$_2$, S(=O)$_2$R$^1$, Se(=O)$_2$ and Se(=O)$_2$R$^1$; wherein R$^1$ and R$^2$ are each independently selected from alkyl, cycloalkyl and aryl;

R$_1$ and R$_2$ are each independently selected from H, alkyl, cycloalkyl, alkene, alkyne, aryl and alkylaryl, a 5 to 12-member single or bicyclo ring; optionally, the ring comprises one or more heteroatom which are the same or different, also optionally, the ring is substituted with a substituent selected from alkyl, cycloalkyl alkoxy, alkoxy, thioalkoxy, aryl, aryloxy, thioaryloxy, alkyaryloxy, thioalkylaryloxy, OH, SH, NH$_2$, a halogen atom, a halogeno alkyl, a halogeno alkoxy, a halogeno thioalkoxy, CH$_2$CN, (CH$_2$)$_n$CN, CN, NO$_2$, S(=O)$_2$, S(=O)$_2$R$^1$, where R$^1$ is selected from alkyl, cycloalkyl and aryl; optionally R$_1$ and R$_2$ together form a ring which is as defined above for R$_1$ and R$_2$; and n is an integer from 0 to 12.

Embodiments of the compounds according to the invention have a general formula "Class IIIa" illustrated below.

Class IIIa

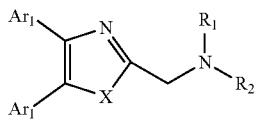

wherein: Ar$_1$, Ar$_2$, R$_1$ and R$_2$ are as defined above; and X is as defined above for X and Y.

Embodiments of the compounds according to the invention have a general formula "Class IIIa1", "Class IIIa2" or "Class IIIa3" illustrated below.

Class IIIa1

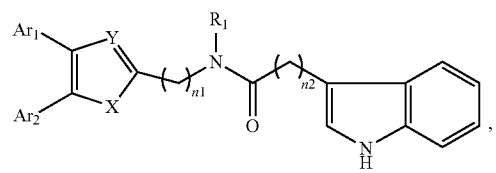

Class IIIa2

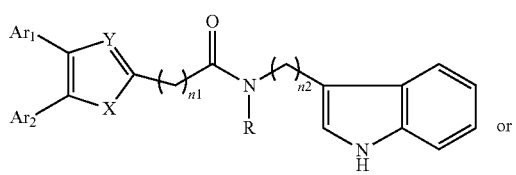

or

Class IIIa3

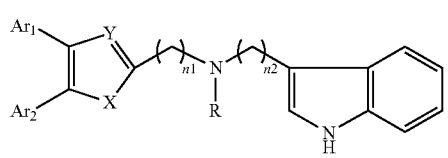

wherein:

Ar$_1$, X and Y are as defined above;

R is selected from H, alkyl, cycloalkyl, alkoxy, thioalkoxy, OH, SH, NH$_2$, a halogen atom, a halogeno alkyl, a halogeno alkoxy, a halogeno thioalkoxy, CH$_2$CN, (CH$_2$)$_n$CN, CN, NO$_2$, S(=O)$_2$, S(=O)$_2$R$^1$, where R$^1$ is selected from alkyl, cycloalkyl and aryl; and n1 and n2 are each independently an integer from 0 to 12.

Embodiments of the compounds according to the invention have a general formula "Class IIIb1", "Class IIIb2" or "Class IIIb3" illustrated in below.

Class IIIb1

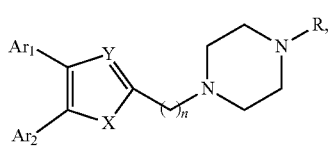

Class IIIb2

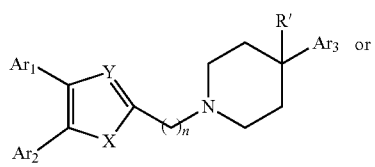

or

Class IIIb3

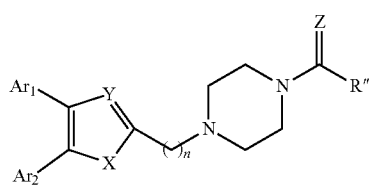

wherein:

Ar$_1$, Ar$_2$, X and Y and R are as defined above; Ar$_3$ is as defined above for Ar$_1$ and Ar$_2$;

Z is selected from O, S, N and C;

R and R' are each independently selected from H, alkyl, cycloalkyl, alkoxy, thioalkoxy, OH, SH, $NH_2$, a halogen atom, a halogeno alkyl, a halogeno alkoxy, a halogeno thioalkoxy, CN, $NO_2$, $S(=O)_2$, $S(=O)_2R^1$, where $R^1$ is selected from alkyl, cycloalkyl and aryl; and R" is selected from H, alkyl, cycloalkyl, alkene, alkyne, aryl and alkylaryl, a 5 to 12-member single or bicyclo ring; optionally, the ring comprises one or more heteroatom which are the same or different, also optionally, the ring is substituted with a substituent selected from alkyl, cycloalkyl alkoxy, alkoxy, thioalkoxy, aryl, aryloxy, thioaryloxy, alkyaryloxy, thioalkylaryloxy, OH, SH, $NH_2$, a halogen atom, a halogeno alkyl, a halogeno alkoxy, a halogeno thioalkoxy, CN, $NO_2$, $S(=O)_2$, $S(=O)_2R^1$, where $R^1$ is selected from alkyl, cycloalkyl and aryl.

Preparation of Compounds of Class IIIa and Class IIIb

Schemes 8-12 below outline the chemical synthesis of compounds identified as "Class IIIa". Examples of these compounds are outlined in Table 4 and Table 4A below.

Secondary amines of Class IIIa may be prepared according to the procedure described in Scheme 8. Bromides 32a and 32b were synthesized according to methods known in the art.[27,28] Secondary amines of Class IIIa were obtained by firstly protection of amine 33 with 2-nitrobenzenesulfonyl chloride to give 34, which then reacted with 32a (or 32b), intermediate compound 35 was obtained. Lastly, deprotection of 35 gave the desired secondary amines, compounds of Class IIIa: 795, 874, 1041, 1042, 1096, 1369.

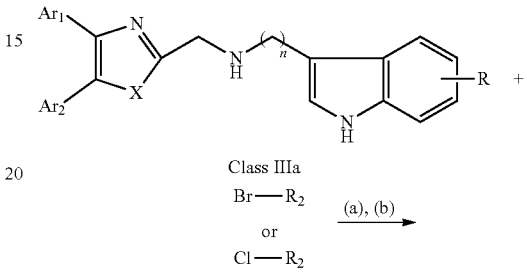

Scheme 9 - Preparation of compounds of Class IIIa.

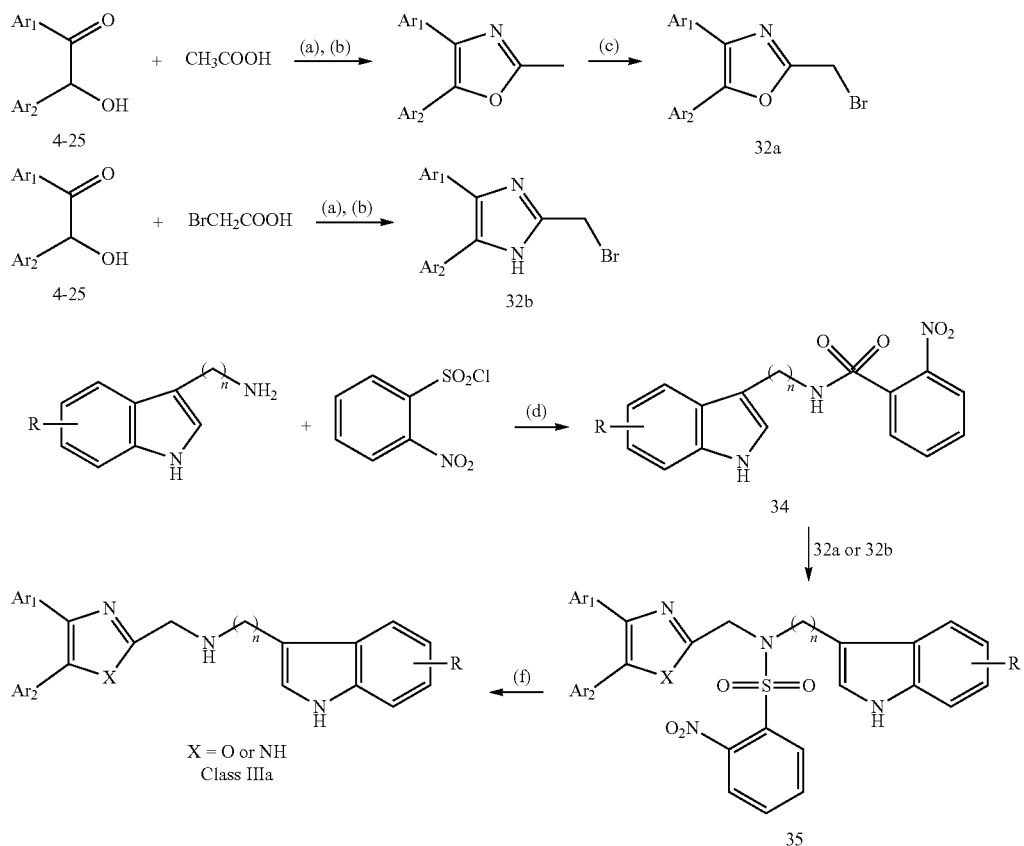

Scheme 8 - Preparation of compounds of Class IIIa.

(a) DCC, DMAP, $CH_2Cl_2$;
(b) $CH_3COONH_4$, aectic acid, reflux, 2 h;
(c) $(PhCO_2)_2$, bromosuccinimide, $CCl_4$, 6 h, rt - reflux;
(d) $Et_3N$, $CH_2Cl_2$, rt, 0.5 h;
(e) $K_2CO_3$, THF, 60° C., 2 h;
(f) PhSH, KOH, $CH_3CN$, 40 min.

-continued

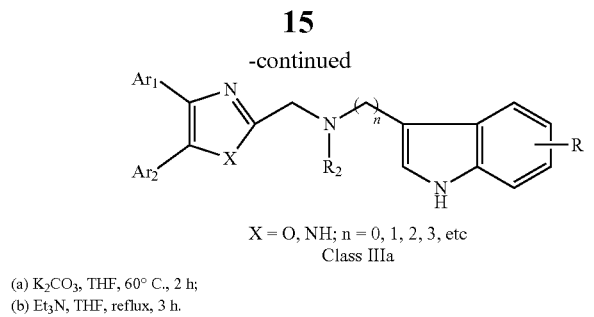

X = O, NH; n = 0, 1, 2, 3, etc
Class IIIa (a) K$_2$CO$_3$, THF, 60° C., 2 h;
(b) Et$_3$N, THF, reflux, 3 h.

Tertiary amines of Class IIIa were prepared by conventional methods as illustrated in Scheme 9. The Compounds of Class IIIa were reacted with bromide or acyl chloride in the presence of weak base such as K$_2$CO$_3$ or Et$_3$N to generate the desired tertiary amines, compounds of Class IIIa: 1186-1188.

Scheme 10 - Preparation of compounds of Class IIIa.

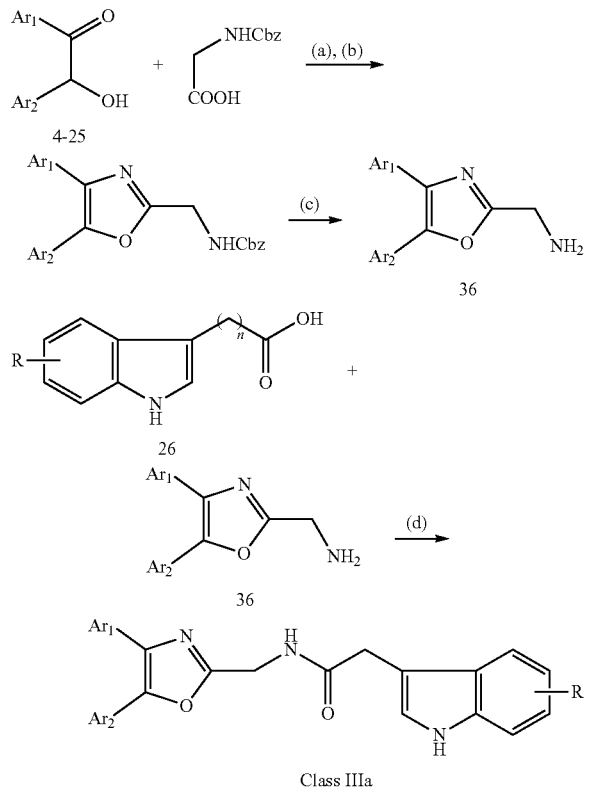

(a) DCC, DMAP, CH$_2$Cl$_2$;
(b) CH$_3$COONH$_4$, acetic acid, reflux, 2 h;
(c) Pd/C, H$_2$, 6 h, rt;
(d) Et$_3$N, HBTU, DMSO, rt, overnight.

Scheme 11 - Preparation of compounds Class IIIa

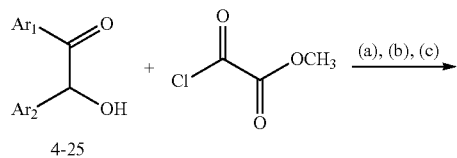

-continued

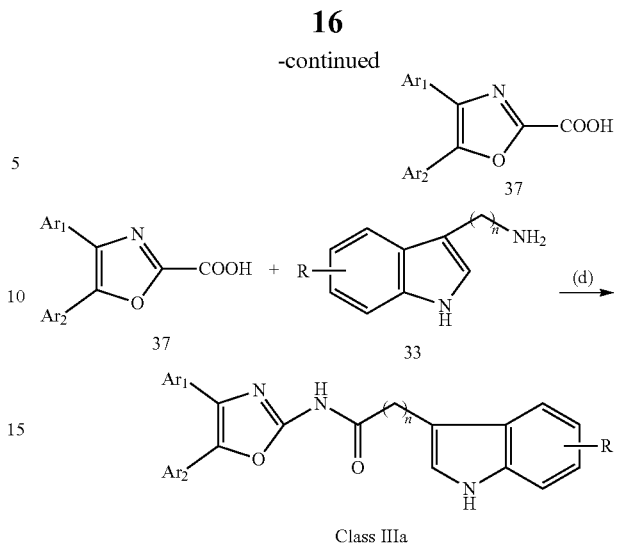

(a) n-Bu$_4$NH$_4$Br, DDQ, PPh$_3$, CH$_2$Cl$_2$;
(b) Urea, acetonitrile, reflux, overnight;
(c) Et$_3$N, THF, reflux, 2 h.

Scheme 12 - Preparation of compounds of Class IIIa.

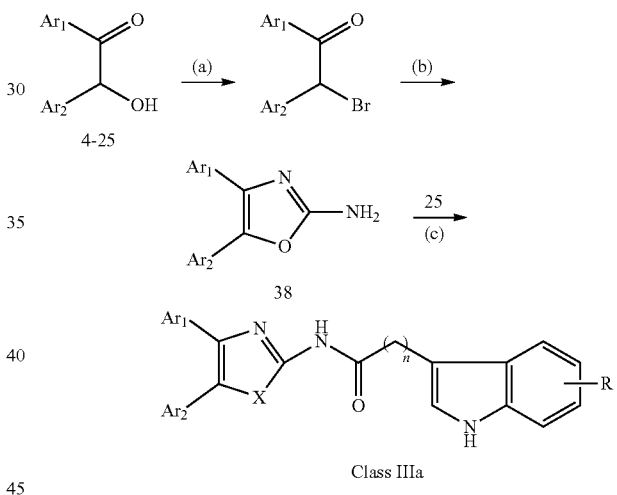

Class IIIa
(a) n-Bu$_4$NH$_4$ Br, DDQ, PPH$_3$, CH$_2$Cl$_2$;
(b) Urea, acetonitrile, reflux, overnight;
(c) Et$_3$N, HBTU, DMSO, rt, pvernight.

Intermediate compounds 36, 37 and 38 were synthesized according to methods known in the art.[27,28] By the condensation of 26 and 36 (Scheme 10), 33 and 37 (Scheme 11), 26 and 38 (Scheme 12), a series of amides, compounds of Class IIIa: 784, 853-856, 876, 1144, 1145 were obtained.

Scheme 13 and Scheme 14 below outline the chemical synthesis of compounds identified as "Class IIIb". These compounds are shown in Table 4 below.

Scheme 13 - Preparation of compounds of Class IIIb.

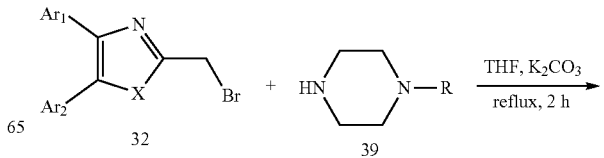

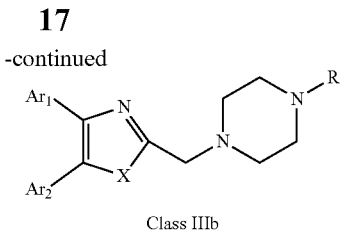

Class IIIb

Scheme 14 - Preparation of compounds of Class IIIb.

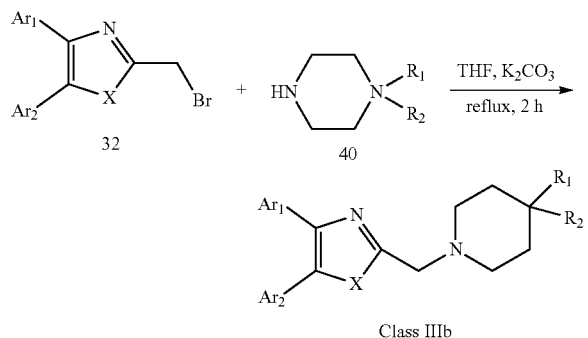

Class IIIb

Alternatively, as illustrated in Scheme 13 and Scheme 14, by the reaction of 32 with substituted piperazines 39 or substituted piperidines 40 in the presence of $K_2CO_3$, a series of compounds of Class IIIb were obtained.

General Procedure for the Preparation of Compound 34 (Scheme 8)

To a mixture of 33 (2 mmol) and trimethylamine (0.278 mL, 49.6 mmol) in 10 mL of dichloromethane cooled in an ice-water bath, 0.44 g (2 mmol) of 2-nitrobenzenesulfonyl chloride was added portionwise over a period of 5 minutes under $N_2$. Then the ice bath is removed and the reaction mixture is allowed to warm to room temperature and stirred for 30 minutes. Water was added to quench the reaction and extracted with $CH_2Cl_2$. The combined organic phase was washed with saturated $NaHCO_3$ and dried with $Na_2SO_4$, filtered, concentrated in vacuum. The crude residue was subjected to chromatography on silica gel to give 34.

General Procedure for the Preparation of Compound 35 (Scheme 8)

To a mixture of 35 (0.5 mmol), 0.21 g (1.5 mmol) of potassium carbonate, and 10 mL of anhydrous tetrahydrofuran, 32a (or 32b) (0.55 mmol) in 5 mL of anhydrous tetrahydrofuran was added dropwise under $N_2$. The resulting mixture was heated at 60° C. for 2 hours. The reaction mixture is allowed to cool to room temperature, diluted with 250 mL of water, and extracted with dichloromethane (3×15 mL). The combined organic extracts were washed with brine (10 mL), dried over $Na_2SO_4$, filtered, and concentrated in vacuum. The crude residue is purified by column chromatography on silica gel to give 35.

General Procedure for the Preparation of Compounds of Class IIIa as Illustrated in Scheme 8

To a solution of 0.11 mL (1 mmol) of thiophenol in 10 mL of acetonitrile, 0.1 mL 10.9 M aqueous potassium hydroxide solution (1 mmol) is added dropwise at 0° C. Then the reaction mixture is allowed to warm to room temperature and 0.24 g (0.42 mmol) of 35 in 5 mL of acetonitrile was added dropwise. The reaction mixture is heated in a 50° C. oil bath for 40 minutes. After cooling to room temperature, 10 mL water was added, and extracted with dichloromethane (3×15 mL). The combined organic extracts were washed with brine, dried over $Na_2SO_4$, filtered, and concentrated under reduced pressure. The residue is purified by column chromatography to give the desired products, compounds of class IIIa as illustrated in Scheme 8: 795, 874, 1041, 1042, 1096.

General Procedure for the Preparation of Compounds of Class IIIa as Illustrated in Scheme 9

Procedure (a): According to the same procedure outlined above for the preparation of 35. A series of compounds of class IIIa as illustrated in Scheme 9 were obtained: 1186-1188.

Procedure (b): To a mixture of Compounds of Class IIIa (1 mmol) and $NEt_3$ (0.83 mL, 6.0 mmol) in 10 mL of THF at 0° C. was added a solution of acyl chloride (1.1 mmol) in 4 mL of THF. The reaction mixture was heated under reflux for 2 hours. After cooling to room temperature, 10 mL water was added, and extracted with dichloromethane (3×15 mL). The combined organic extracts were washed with brine, dried over $Na_2SO_4$, filtered, and concentrated under reduced pressure. The residue is purified by column chromatography to give the desired products, compounds of Class IIIa as illustrated in Scheme 9.

General Procedure for the Preparation of Amides of Class IIIa as Illustrated in Scheme 10-12

To a suspension of acid 26 (or 37) (0.12 mmol) and 36 (or 33 or 38) (0.1 mmol) and $Et_3N$ (0.4 mmol) in DMSO (3 mL), HBTU (0.4 mmol) was added. The mixture was stirred at room temperature overnight. 10 mL water was added and extracted with dichloromethane (3×15 mL). The combined organic phases were washed with brine, dried over $Na_2SO_4$, filtered, and concentrated under reduced pressure. The crude residue was purified by column chromatography to give products of Class IIIa: 784, 853-856, 876, 1144 and 1145.

General Procedure for the Preparation of Compounds of Class IIIb as Illustrated in Scheme 13 and Scheme 14

A mixture of 32 (0.1 mmol), 39 or 40 (1 mmol) and 0.1 g (0.7 mmol) of potassium carbonate in 10 mL of anhydrous tetrahydrofuran was heated at 60° C. for 2 hours. The reaction mixture is allowed to cool to room temperature, diluted with 250 mL of water, and extracted with dichloromethane (3×15 mL). The combined organic extracts were washed with brine (10 mL), dried over $Na_2SO_4$, filtered, and concentrated in vacuum. The crude residue was purified by column chromatography on silica gel to give the desired products, compounds of Class IIIb.

Examples of compounds of Class IIIa and Class IIIb are outlined in Table 4 below, and preferred embodiments are further outlined in Table 4A.

TABLE 4
| ID | Structure |
|---|---|
| 795 | 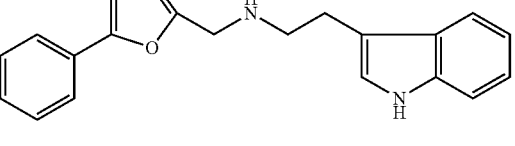 |
| 874 | 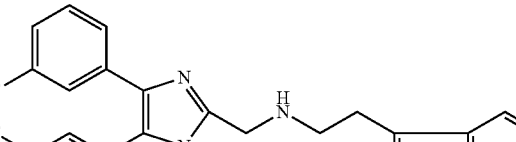 |
| 1041 | 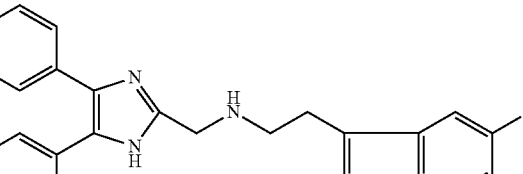 |
| 1042 | 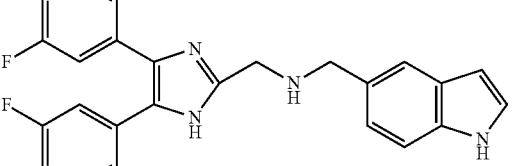 |
| 1096 | 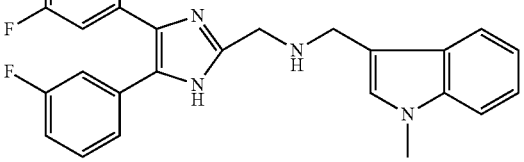 |
| 1369 | 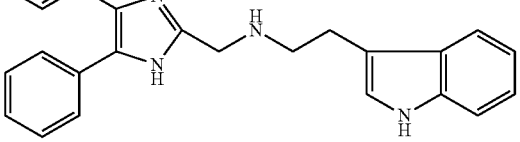 |

TABLE 4-continued

| ID | Structure |
|---|---|
| 1186 | 4,5-bis(3-fluorophenyl)-1H-imidazol-2-yl methyl-N-(cyanomethyl)-N-(2-(1H-indol-3-yl)ethyl)amine |
| 1187 | 4,5-diphenyl-1H-imidazol-2-yl methyl-N-(cyanomethyl)-N-(2-(1H-indol-3-yl)ethyl)amine |
| 1188 | 4,5-diphenyloxazol-2-yl methyl-N-(cyanomethyl)-N-(2-(1H-indol-3-yl)ethyl)amine |
| 784 | N-((4,5-diphenyloxazol-2-yl)methyl)-2-(1H-indol-3-yl)acetamide |
| 876 | N-((4,5-bis(3-fluorophenyl)oxazol-2-yl)methyl)-2-(1H-indol-3-yl)acetamide |
| 853 | N-(4,5-bis(3-fluorophenyl)oxazol-2-yl)-2-(1H-indol-3-yl)acetamide |

TABLE 4-continued

| ID | Structure |
|---|---|
| 854 | 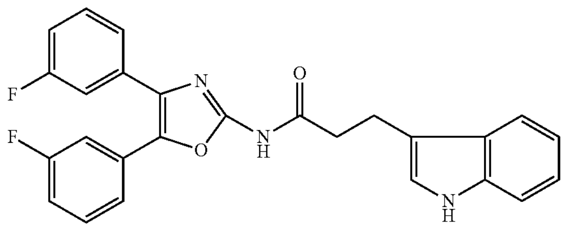 [SMILES: O=C(CCc1c[nH]c2ccccc12)Nc1nc(-c2cccc(F)c2)c(-c2cccc(F)c2)o1] |
| 855 | 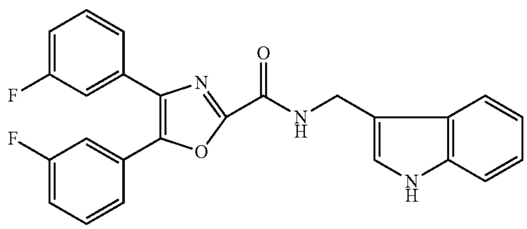 [SMILES: O=C(NCc1c[nH]c2ccccc12)c1nc(-c2cccc(F)c2)c(-c2cccc(F)c2)o1] |
| 856 | 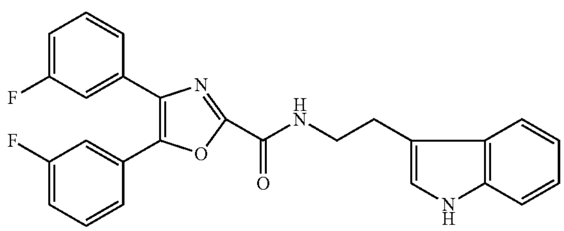 [SMILES: O=C(NCCc1c[nH]c2ccccc12)c1nc(-c2cccc(F)c2)c(-c2cccc(F)c2)o1] |
| 1144 | 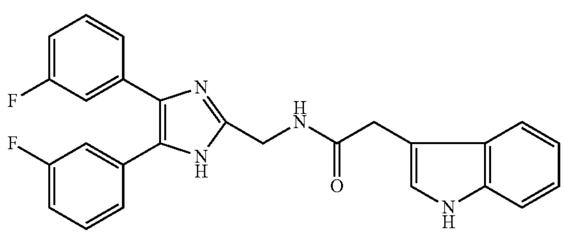 [SMILES: O=C(Cc1c[nH]c2ccccc12)NCc1nc(-c2cccc(F)c2)c(-c2cccc(F)c2)[nH]1] |
| 1145 | 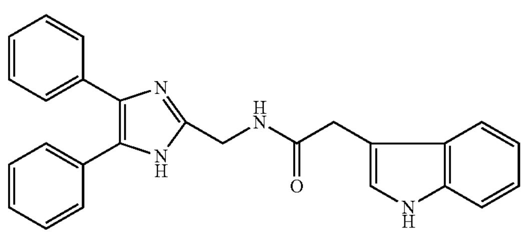 [SMILES: O=C(Cc1c[nH]c2ccccc12)NCc1nc(-c2ccccc2)c(-c2ccccc2)[nH]1] |
| 1076 | 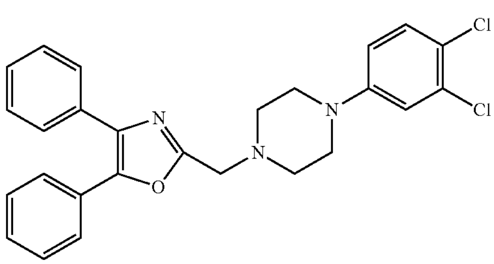 [SMILES: Clc1ccc(N2CCN(Cc3nc(-c4ccccc4)c(-c4ccccc4)o3)CC2)cc1Cl] |

TABLE 4-continued
| ID | Structure |
|---|---|
| 1077 | 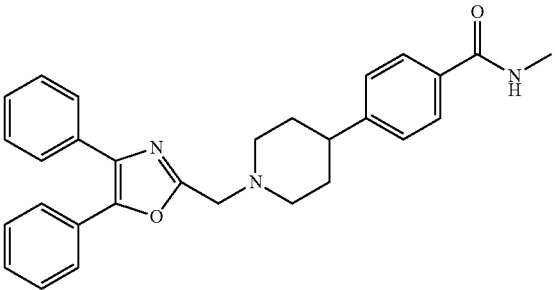 [SMILES: CNC(=O)c1ccc(C2CCN(Cc3nc(-c4ccccc4)c(-c4ccccc4)o3)CC2)cc1] |
| 1078 | 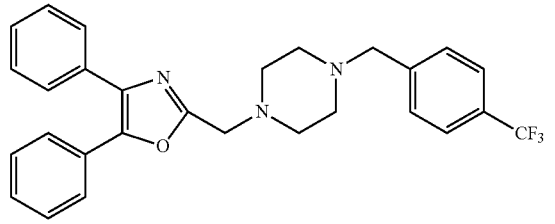 [SMILES: FC(F)(F)c1ccc(CN2CCN(Cc3nc(-c4ccccc4)c(-c4ccccc4)o3)CC2)cc1] |
| 1079 | 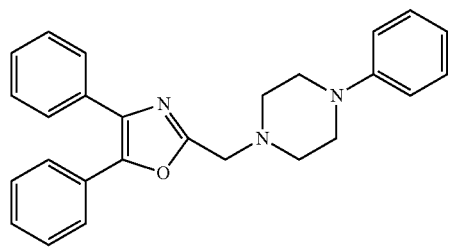 [SMILES: c1ccc(-c2nc(CN3CCN(c4ccccc4)CC3)oc2-c2ccccc2)cc1] |
| 1080 | 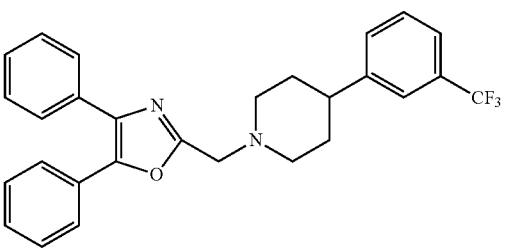 [SMILES: FC(F)(F)c1cccc(C2CCN(Cc3nc(-c4ccccc4)c(-c4ccccc4)o3)CC2)c1] |
| 1089 | 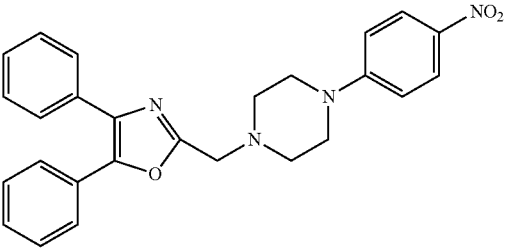 [SMILES: O=[N+]([O-])c1ccc(N2CCN(Cc3nc(-c4ccccc4)c(-c4ccccc4)o3)CC2)cc1] |
| 1090 | 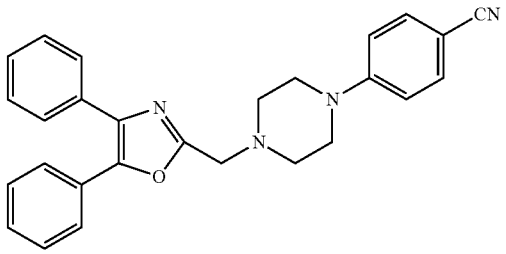 |

TABLE 4-continued
| ID | Structure |
|---|---|
| 1091 | 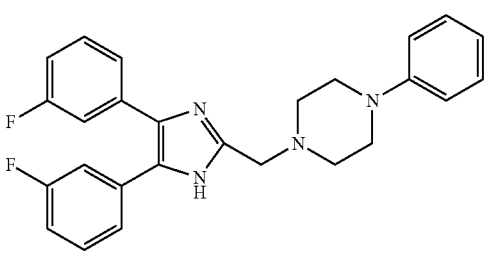 [SMILES: Fc1cccc(-c2nc(CN3CCN(c4ccccc4)CC3)[nH]c2-c2cccc(F)c2)c1] |
| 1092 | 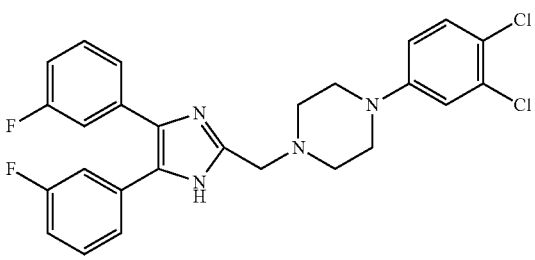 [SMILES: Fc1cccc(-c2nc(CN3CCN(c4ccc(Cl)c(Cl)c4)CC3)[nH]c2-c2cccc(F)c2)c1] |
| 1093 | 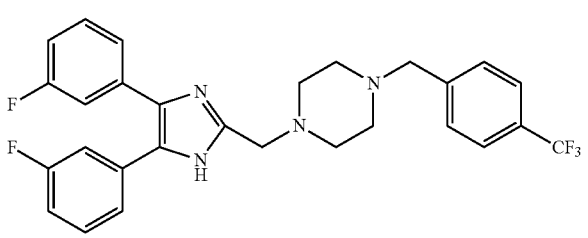 [SMILES: Fc1cccc(-c2nc(CN3CCN(Cc4ccc(C(F)(F)F)cc4)CC3)[nH]c2-c2cccc(F)c2)c1] |
| 1094 | 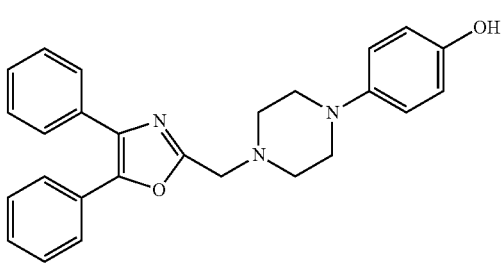 |
| 1097 | 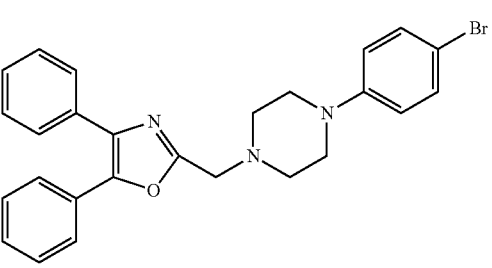 [SMILES: Brc1ccc(N2CCN(Cc3nc(-c4ccccc4)c(-c4ccccc4)o3)CC2)cc1] |
| 1098 | 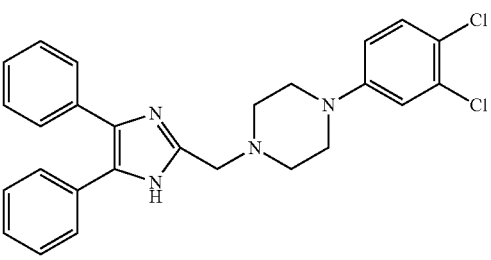 [SMILES: Clc1ccc(N2CCN(Cc3nc(-c4ccccc4)c(-c4ccccc4)[nH]3)CC2)cc1Cl] |

TABLE 4-continued

| ID | Structure |
|---|---|
| 1099 | (structure) |
| 1100 | (structure) |
| 1101 | (structure) |
| 1102 | (structure) |
| 1103 | (structure) |
| 1104 | (structure) |

TABLE 4-continued
| ID | Structure |
|---|---|
| 1120 | 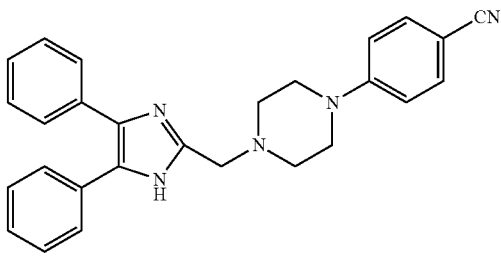 [SMILES: N#Cc1ccc(N2CCN(Cc3nc(-c4ccccc4)c(-c4ccccc4)[nH]3)CC2)cc1] |
| 1121 | 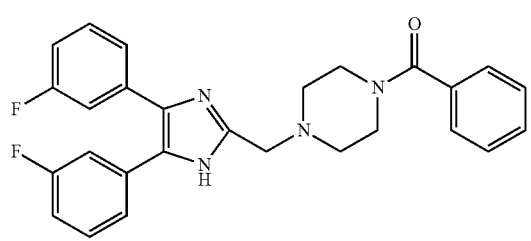 [SMILES: O=C(c1ccccc1)N1CCN(Cc2nc(-c3cccc(F)c3)c(-c3cccc(F)c3)[nH]2)CC1] |
| 1122 | 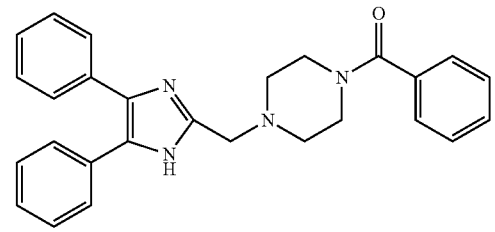 [SMILES: O=C(c1ccccc1)N1CCN(Cc2nc(-c3ccccc3)c(-c3ccccc3)[nH]2)CC1] |
| 1123 | 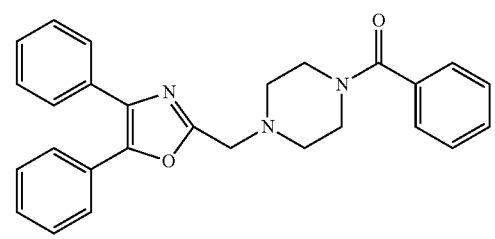 |
| 1124 | 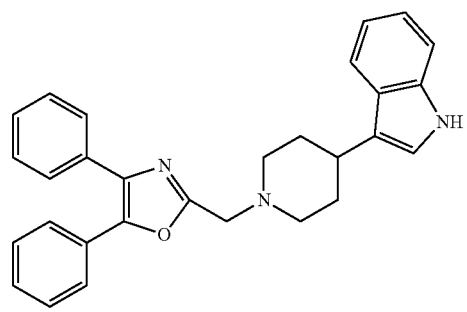 [SMILES: c1ccc(-c2nc(CN3CCC(c4c[nH]c5ccccc45)CC3)oc2-c2ccccc2)cc1] |
| 1125 | 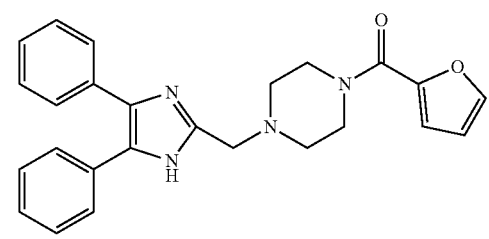 |

TABLE 4-continued
| ID | Structure |
|---|---|
| 1126 | 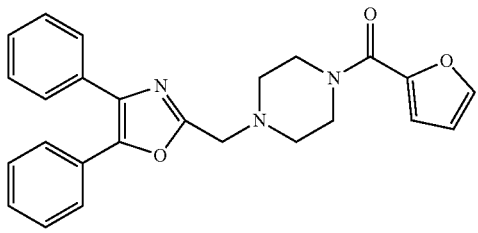 [SMILES: O=C(c1ccco1)N1CCN(Cc2nc(-c3ccccc3)c(-c3ccccc3)o2)CC1] |
| 1127 | 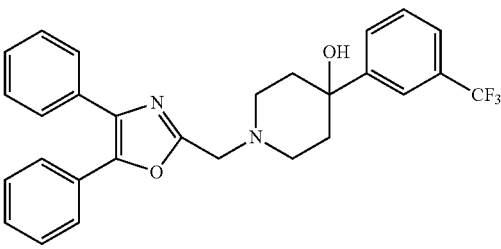 [SMILES: OC1(c2cccc(C(F)(F)F)c2)CCN(Cc2nc(-c3ccccc3)c(-c3ccccc3)o2)CC1] |
| 1129 | 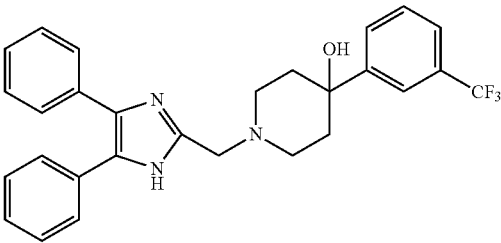 [SMILES: OC1(c2cccc(C(F)(F)F)c2)CCN(Cc2nc(-c3ccccc3)c(-c3ccccc3)[nH]2)CC1] |
| 1137 | 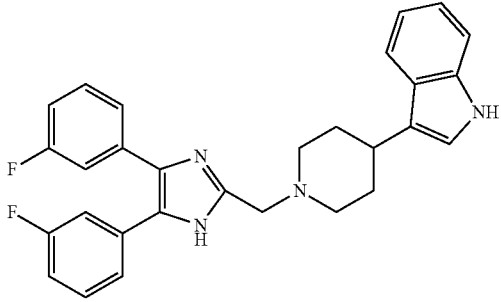 [SMILES: Fc1cccc(-c2nc(CN3CCC(c4c[nH]c5ccccc45)CC3)[nH]c2-c2cccc(F)c2)c1] |
| 1139 | 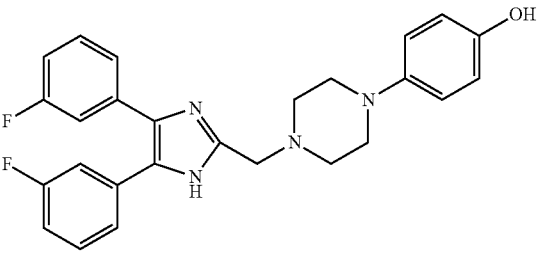 |

TABLE 4-continued

| ID | Structure |
|----|-----------|
| 1140 | 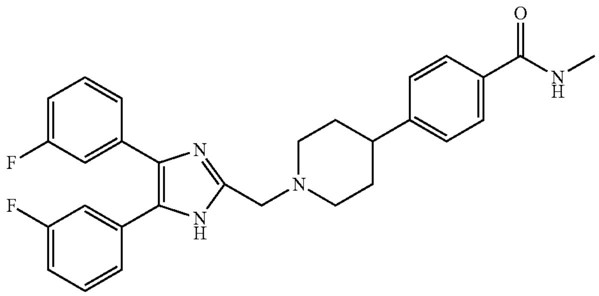 [SMILES: CNC(=O)c1ccc(C2CCN(Cc3nc(-c4cccc(F)c4)c(-c4cccc(F)c4)[nH]3)CC2)cc1] |
| 1141 | 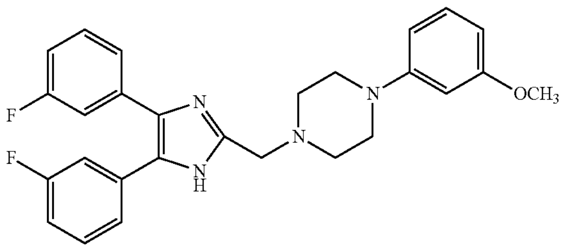 [SMILES: COc1cccc(N2CCN(Cc3nc(-c4cccc(F)c4)c(-c4cccc(F)c4)[nH]3)CC2)c1] |
| 1142 | 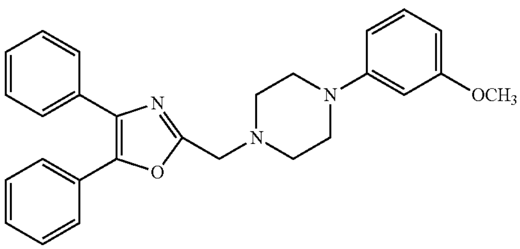 [SMILES: COc1cccc(N2CCN(Cc3nc(-c4ccccc4)c(-c4ccccc4)o3)CC2)c1] |
| 1143 | 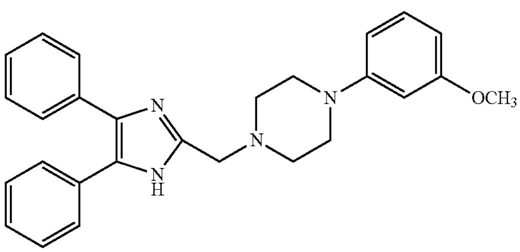 [SMILES: COc1cccc(N2CCN(Cc3nc(-c4ccccc4)c(-c4ccccc4)[nH]3)CC2)c1] |
| 1173 | 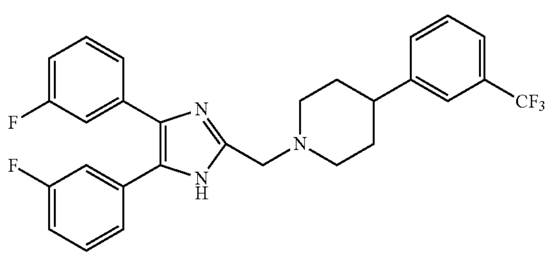 [SMILES: Fc1cccc(-c2nc(CN3CCC(c4cccc(C(F)(F)F)c4)CC3)[nH]c2-c2cccc(F)c2)c1] |
| 1174 | 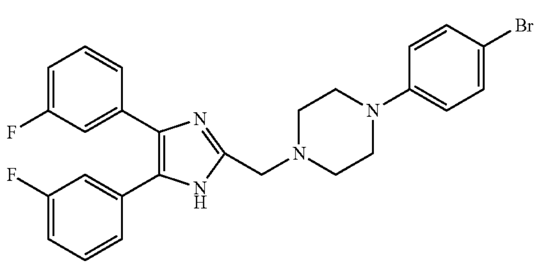 [SMILES: Fc1cccc(-c2nc(CN3CCN(c4ccc(Br)cc4)CC3)[nH]c2-c2cccc(F)c2)c1] |

TABLE 4-continued
| ID | Structure |
|---|---|
| 1175 | 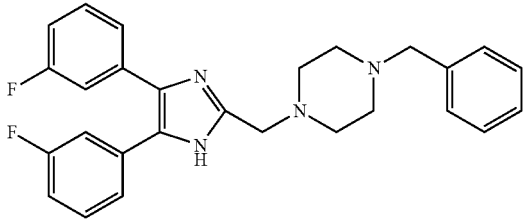 |
| 1176 | 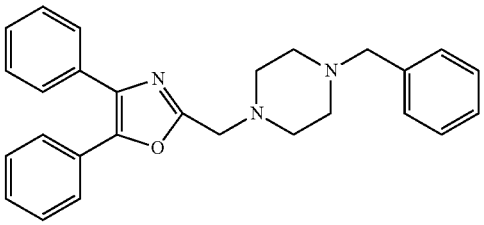 [SMILES: c1ccc(CN2CCN(Cc3nc(-c4ccccc4)c(-c4ccccc4)o3)CC2)cc1] |
| 1177 | 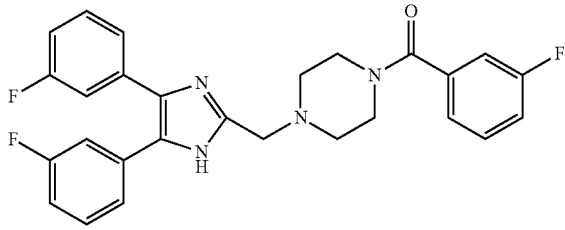 [SMILES: O=C(c1cccc(F)c1)N1CCN(Cc2nc(-c3cccc(F)c3)c(-c3cccc(F)c3)[nH]2)CC1] |
| 1178 | 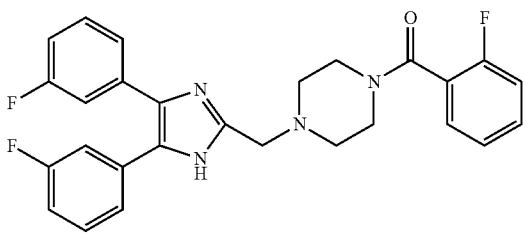 [SMILES: O=C(c1ccccc1F)N1CCN(Cc2nc(-c3cccc(F)c3)c(-c3cccc(F)c3)[nH]2)CC1] |
| 1179 | 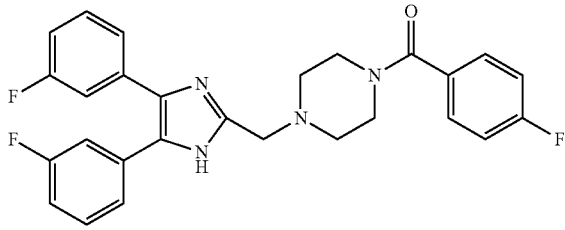 [SMILES: O=C(c1ccc(F)cc1)N1CCN(Cc2nc(-c3cccc(F)c3)c(-c3cccc(F)c3)[nH]2)CC1] |
| 1180 | 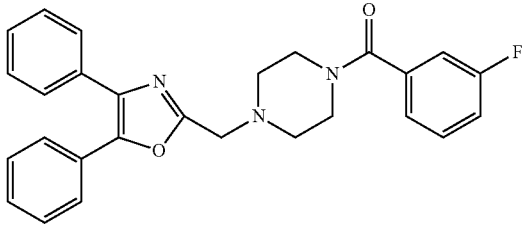 [SMILES: O=C(c1cccc(F)c1)N1CCN(Cc2nc(-c3ccccc3)c(-c3ccccc3)o2)CC1] |

TABLE 4-continued
| ID | Structure |
|---|---|
| 1181 | 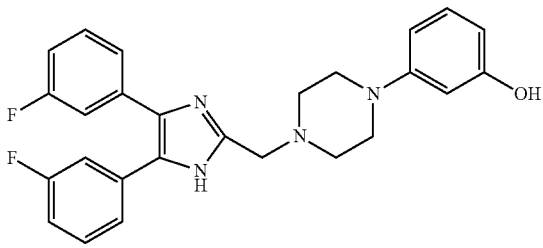 [SMILES: Oc1cccc(N2CCN(Cc3nc(-c4cccc(F)c4)c(-c4cccc(F)c4)[nH]3)CC2)c1] |
| 1182 | 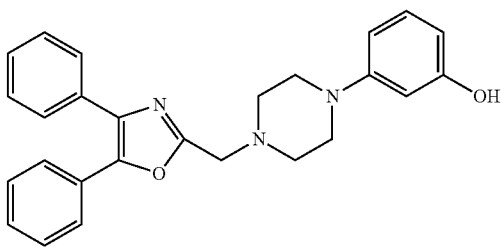 [SMILES: Oc1cccc(N2CCN(Cc3nc(-c4ccccc4)c(-c4ccccc4)o3)CC2)c1] |
| 1183 | 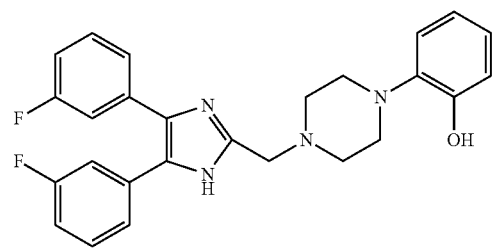 [SMILES: Oc1ccccc1N1CCN(Cc2nc(-c3cccc(F)c3)c(-c3cccc(F)c3)[nH]2)CC1] |
| 1184 | 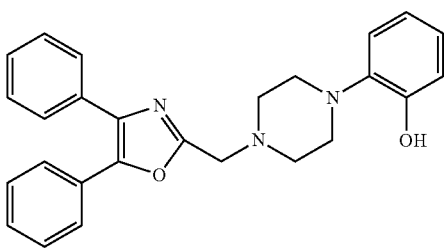 [SMILES: Oc1ccccc1N1CCN(Cc2nc(-c3ccccc3)c(-c3ccccc3)o2)CC1] |
| 1209 | 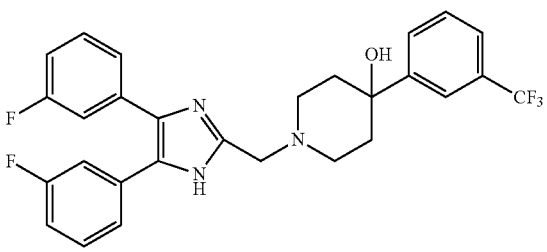 [SMILES: OC1(c2cccc(C(F)(F)F)c2)CCN(Cc2nc(-c3cccc(F)c3)c(-c3cccc(F)c3)[nH]2)CC1] |
| 1210 | 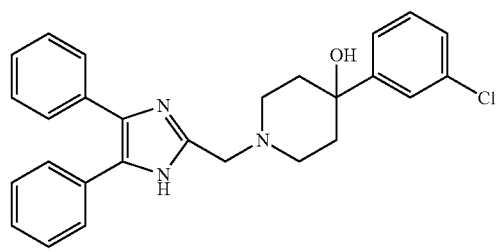 [SMILES: OC1(c2cccc(Cl)c2)CCN(Cc2nc(-c3ccccc3)c(-c3ccccc3)[nH]2)CC1] |

TABLE 4-continued

| ID | Structure |
|---|---|
| 1211 | 4-(4-(trifluoromethyl)phenyl)-1-((4,5-diphenyl-1H-imidazol-2-yl)methyl)piperidin-4-ol |
| 1212 | 4-(4-((4,5-bis(3-fluorophenyl)oxazol-2-yl)methyl)piperazin-1-yl)phenol |
| 1213 | 4,5-bis(3-fluorophenyl)-2-((4-phenylpiperazin-1-yl)methyl)oxazole |
| 1214 | 3-(1-((4,5-bis(3-fluorophenyl)oxazol-2-yl)methyl)piperidin-4-yl)-1H-indole |
| 1227 | 2-(4-((4,5-diphenyloxazol-2-yl)methyl)piperazin-1-yl)pyridine |
| 1229 | 4-(1-((4,5-diphenyloxazol-2-yl)methyl)piperidin-4-yl)pyrimidin-2-amine |

TABLE 4-continued
| ID | Structure |
|---|---|
| 1284 | 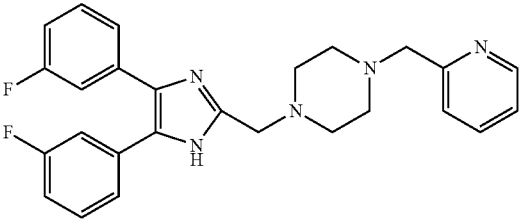 [SMILES: Fc1cccc(-c2nc(CN3CCN(Cc4ccccn4)CC3)[nH]c2-c2cccc(F)c2)c1] |
| 1285 | 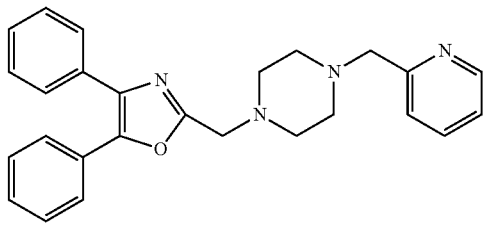 [SMILES: c1ccc(-c2nc(CN3CCN(Cc4ccccn4)CC3)oc2-c2ccccc2)cc1] |
| 1286 | 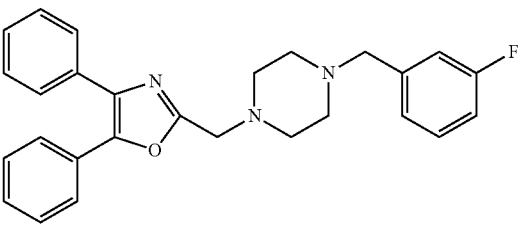 [SMILES: Fc1cccc(CN2CCN(Cc3nc(-c4ccccc4)c(-c4ccccc4)o3)CC2)c1] |
| 1287 | 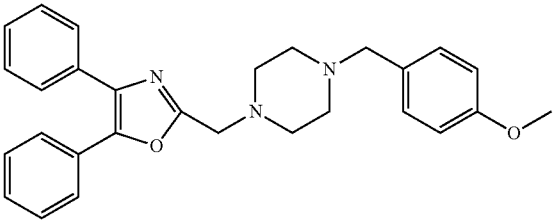 [SMILES: COc1ccc(CN2CCN(Cc3nc(-c4ccccc4)c(-c4ccccc4)o3)CC2)cc1] |
| 1288 | 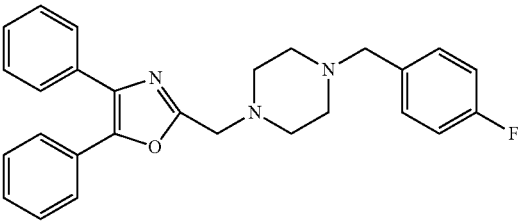 [SMILES: Fc1ccc(CN2CCN(Cc3nc(-c4ccccc4)c(-c4ccccc4)o3)CC2)cc1] |
| 1289 | 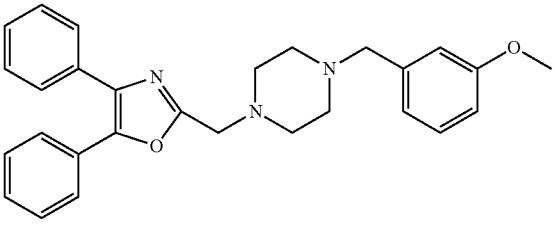 [SMILES: COc1cccc(CN2CCN(Cc3nc(-c4ccccc4)c(-c4ccccc4)o3)CC2)c1] |

TABLE 4-continued
| ID | Structure |
|---|---|
| 1290 | 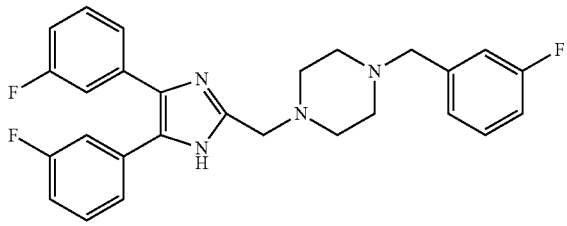 [SMILES: Fc1cccc(CN2CCN(Cc3nc(-c4cccc(F)c4)c(-c4cccc(F)c4)[nH]3)CC2)c1] |
| 1291 | 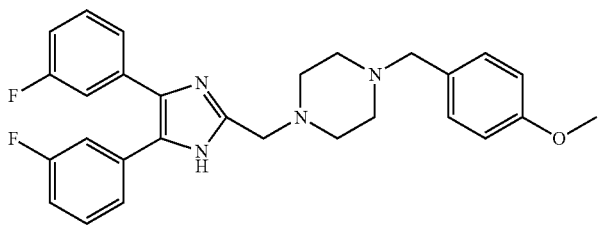 [SMILES: COc1ccc(CN2CCN(Cc3nc(-c4cccc(F)c4)c(-c4cccc(F)c4)[nH]3)CC2)cc1] |
| 1312 | 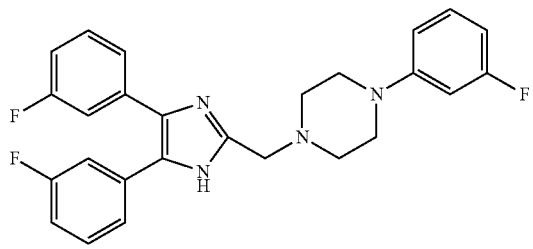
C$_{26}$H$_{23}$F$_3$N$_4$
448.49 |
| 1313 | 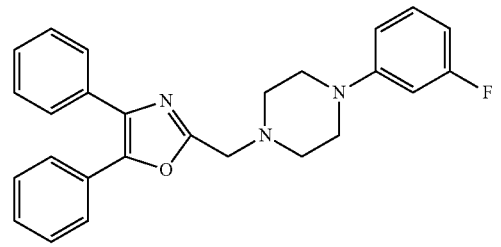 [SMILES: Fc1cccc(N2CCN(Cc3nc(-c4ccccc4)c(-c4ccccc4)o3)CC2)c1] |
| 1314 | 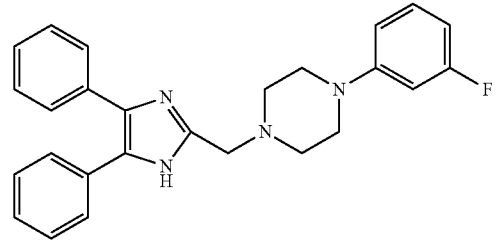 [SMILES: Fc1cccc(N2CCN(Cc3nc(-c4ccccc4)c(-c4ccccc4)[nH]3)CC2)c1] |
| 1315 | 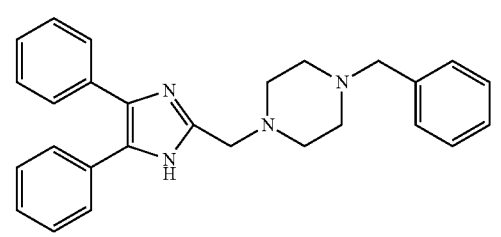 [SMILES: c1ccc(CN2CCN(Cc3nc(-c4ccccc4)c(-c4ccccc4)[nH]3)CC2)cc1] |

TABLE 4-continued
| ID | Structure |
|---|---|
| 1357 | 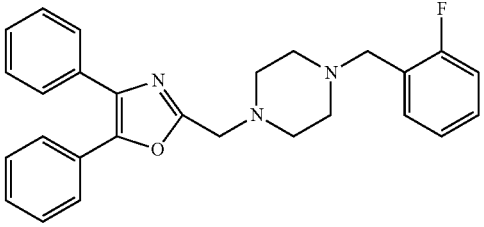 [SMILES: Fc1ccccc1CN1CCN(Cc2nc(-c3ccccc3)c(-c3ccccc3)o2)CC1] |
| 1358 | 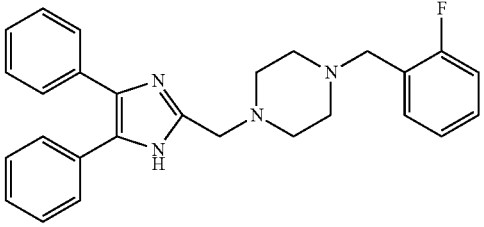 [SMILES: Fc1ccccc1CN1CCN(Cc2nc(-c3ccccc3)c(-c3ccccc3)[nH]2)CC1] |
| 1359 | 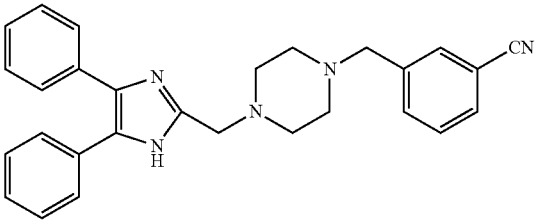 [SMILES: N#Cc1cccc(CN2CCN(Cc3nc(-c4ccccc4)c(-c4ccccc4)[nH]3)CC2)c1] |
| 1360 | 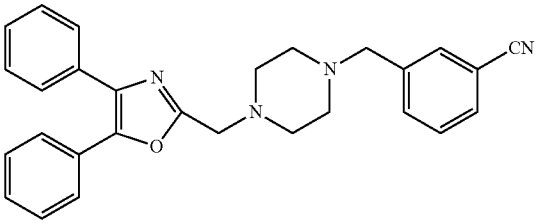 [SMILES: N#Cc1cccc(CN2CCN(Cc3nc(-c4ccccc4)c(-c4ccccc4)o3)CC2)c1] |
| 1361 | 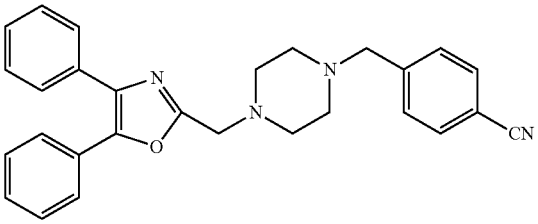 [SMILES: N#Cc1ccc(CN2CCN(Cc3nc(-c4ccccc4)c(-c4ccccc4)o3)CC2)cc1] |
| 1362 | 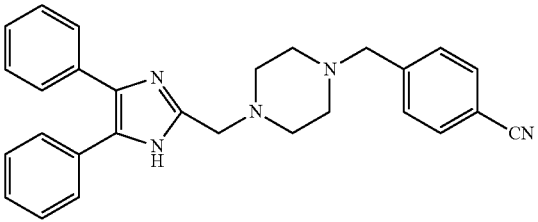 |

TABLE 4-continued
| ID | Structure |
|---|---|
| 1363 | 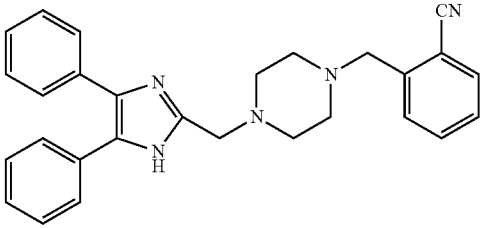 [SMILES: N#Cc1ccccc1CN1CCN(Cc2nc(-c3ccccc3)c(-c3ccccc3)[nH]2)CC1] |
| 1364 | 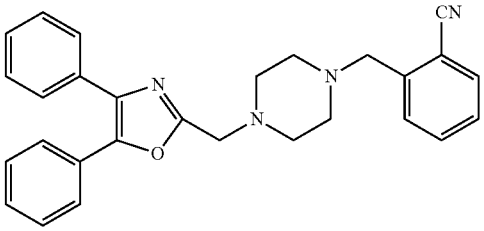 [SMILES: N#Cc1ccccc1CN1CCN(Cc2nc(-c3ccccc3)c(-c3ccccc3)o2)CC1] |
| 1366 | 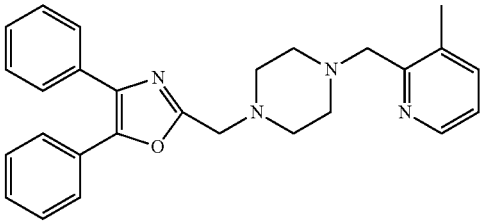 [SMILES: Cc1cccnc1CN1CCN(Cc2nc(-c3ccccc3)c(-c3ccccc3)o2)CC1] |
| 1367 | 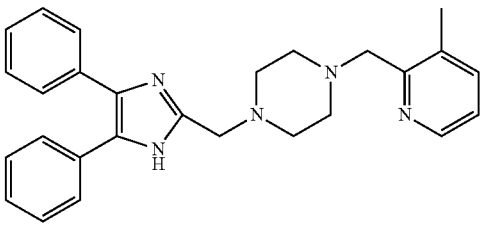 [SMILES: Cc1cccnc1CN1CCN(Cc2nc(-c3ccccc3)c(-c3ccccc3)[nH]2)CC1] |
| 1368 | 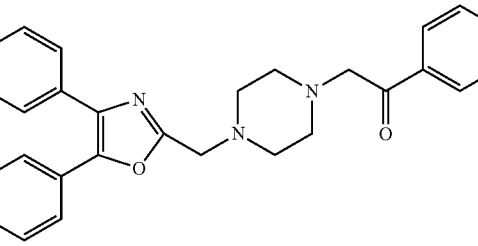 |
| 1369 | 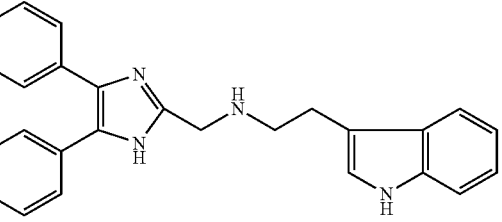 |

TABLE 4-continued
| ID | Structure |
|---|---|
| 1370 | 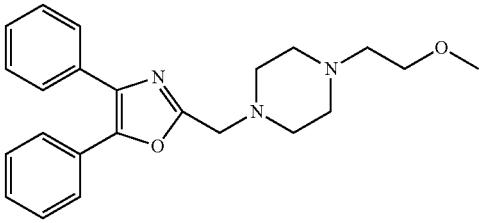 [SMILES: COCCN1CCN(Cc2nc(-c3ccccc3)c(-c3ccccc3)o2)CC1] |
| 1371 | 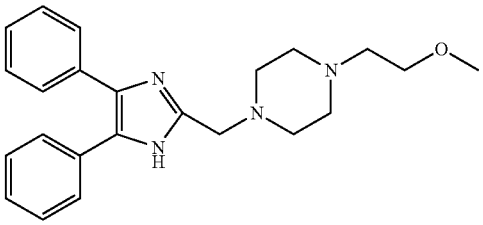 [SMILES: COCCN1CCN(Cc2nc(-c3ccccc3)c(-c3ccccc3)[nH]2)CC1] |
| 1372 | 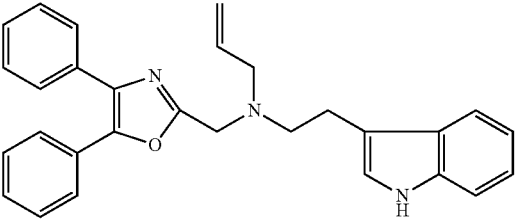 [SMILES: C=CCN(CCc1c[nH]c2ccccc12)Cc1nc(-c2ccccc2)c(-c2ccccc2)o1] |
| 1394 | 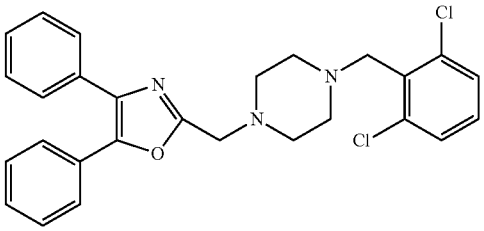 [SMILES: Clc1cccc(Cl)c1CN1CCN(Cc2nc(-c3ccccc3)c(-c3ccccc3)o2)CC1] |
| 1395 | 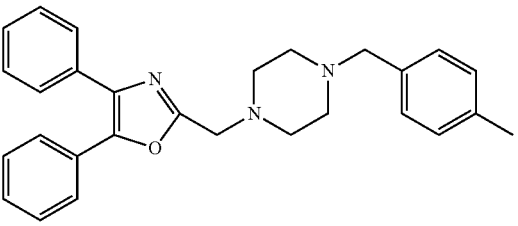 [SMILES: Cc1ccc(CN2CCN(Cc3nc(-c4ccccc4)c(-c4ccccc4)o3)CC2)cc1] |
| 1396 | 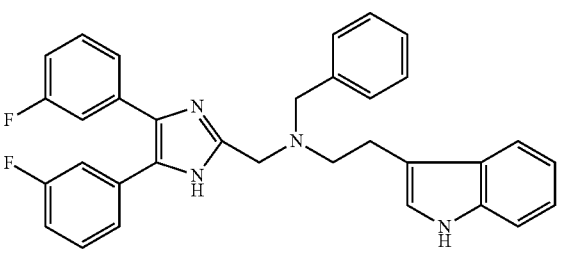 [SMILES: Fc1cccc(-c2nc(CN(CCc3c[nH]c4ccccc34)Cc3ccccc3)[nH]c2-c2cccc(F)c2)c1] |

TABLE 4-continued

| ID | Structure |
|---|---|
| 1397 | 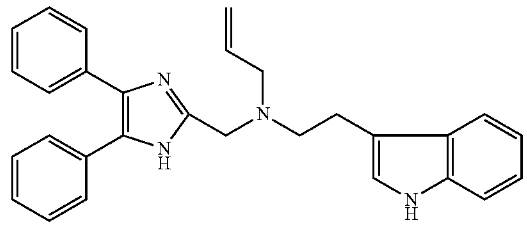 [SMILES: C=CCN(CCc1c[nH]c2ccccc12)Cc1nc(-c2ccccc2)c(-c2ccccc2)[nH]1] |
| 1400 | 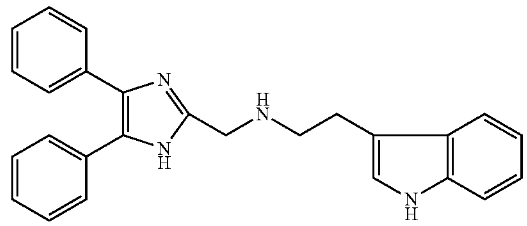 [SMILES: c1ccc(-c2nc(CNCCc3c[nH]c4ccccc34)[nH]c2-c2ccccc2)cc1] |
| 1401 | 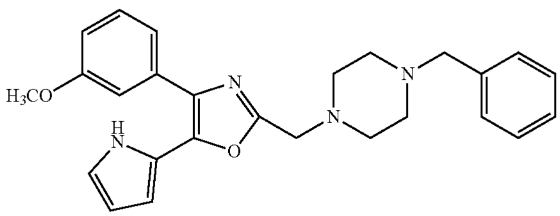 [SMILES: COc1cccc(-c2nc(CN3CCN(Cc4ccccc4)CC3)oc2-c2ccc[nH]2)c1] |
| 1402 | 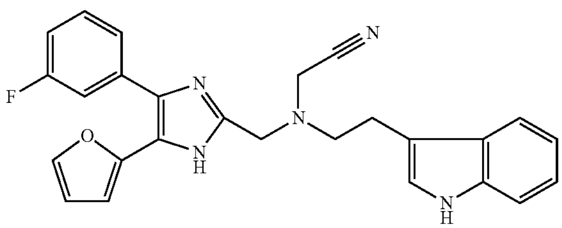 [SMILES: N#CCN(CCc1c[nH]c2ccccc12)Cc1nc(-c2cccc(F)c2)c(-c2ccco2)[nH]1] |
| 1403 | 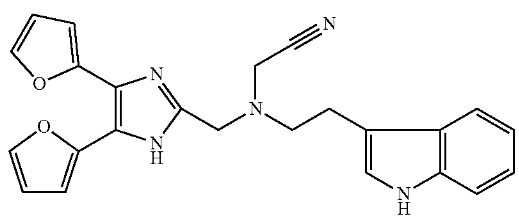 [SMILES: N#CCN(CCc1c[nH]c2ccccc12)Cc1nc(-c2ccco2)c(-c2ccco2)[nH]1] |
| 1404 | 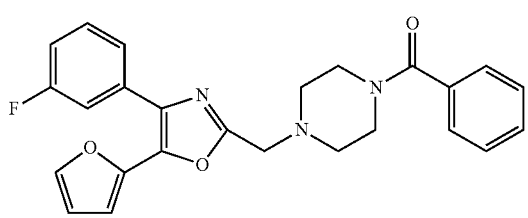 [SMILES: O=C(c1ccccc1)N1CCN(Cc2nc(-c3cccc(F)c3)c(-c3ccco3)o2)CC1] |
| 1405 | 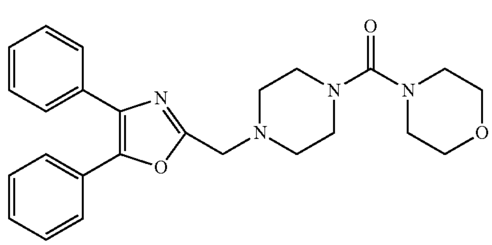 [SMILES: O=C(N1CCOCC1)N1CCN(Cc2nc(-c3ccccc3)c(-c3ccccc3)o2)CC1] |

TABLE 4-continued

| ID | Structure |
|---|---|
| 1039 | (3-fluorophenyl, 3-fluorophenyl)-imidazole-CH2-N(SO2-2-nitrophenyl)-CH2CH2-(5-methoxyindol-3-yl) |
| 1040 | (3-fluorophenyl, 3-fluorophenyl)-imidazole-CH2-N(SO2-2-nitrophenyl)-CH2-(indol-5-yl) |
| 1373 | (phenyl, phenyl)-imidazole-CH2-N(SO2-2-nitrophenyl)-CH2CH2-(indol-3-yl) |

TABLE 4A

| ID | Structure |
|---|---|
| 1141 | (3-fluorophenyl, 3-fluorophenyl)-imidazole-CH2-piperazine-N-(3-methoxyphenyl) |
| 1143 | (phenyl, phenyl)-imidazole-CH2-piperazine-N-(3-methoxyphenyl) |
| 1181 | (3-fluorophenyl, 3-fluorophenyl)-imidazole-CH2-piperazine-N-(3-fluorophenyl) |
| 1314 | (phenyl, phenyl)-imidazole-CH2-piperazine-N-(3-fluorophenyl) |

TABLE 4A-continued

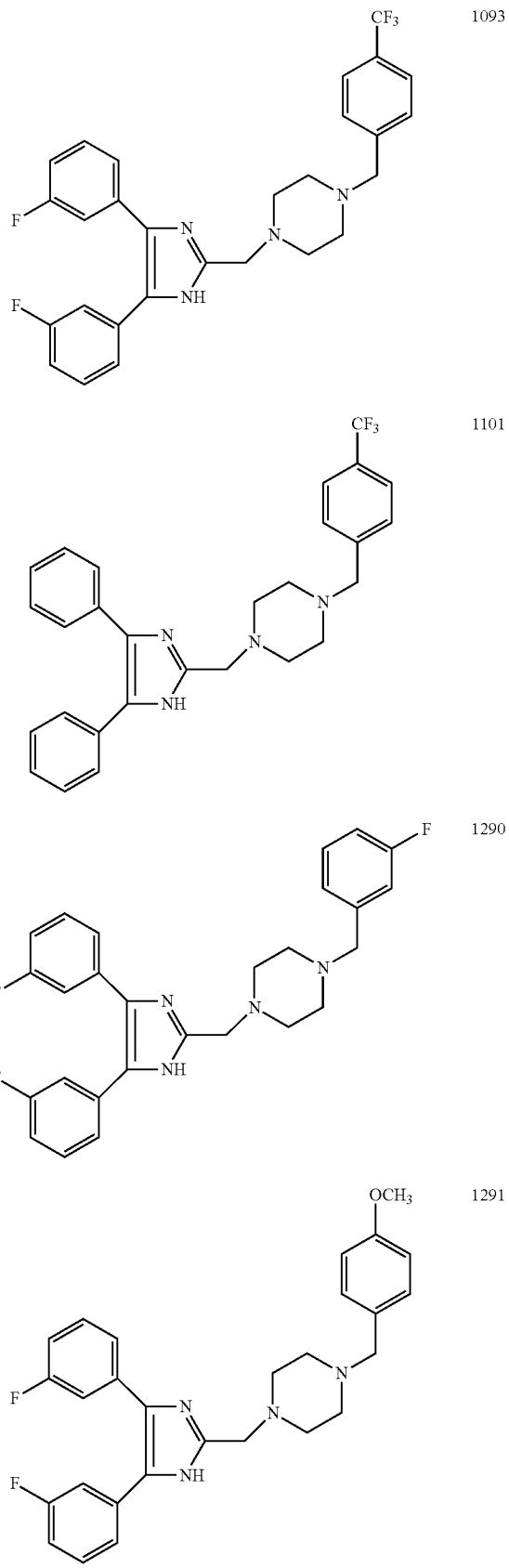

TABLE 4A-continued

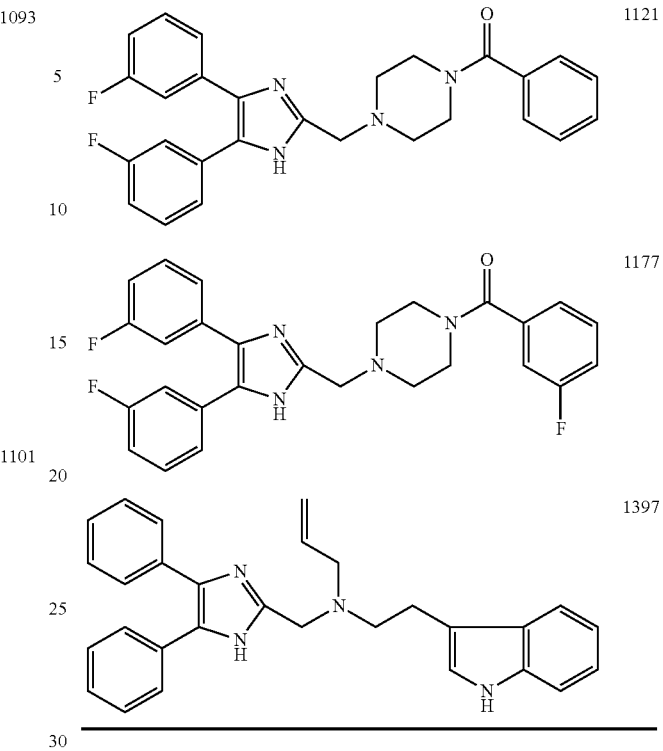

Characterization of Intermediate

35a: White solid. Yield: 82%. $^1$H NMR (500 MHz, CDCl$_3$) δ 8.04-7.94 (m, 2H), 7.59-7.52 (m, 3H), 7.51-7.49 (m, 2H), 7.47-7.41 (m, 3H), 7.40-7.31 (m, 6H), 7.28 (d, J=8.1 Hz, 1H), 7.16-7.11 (m, 1H), 7.07 (s, 1H), 7.03-6.99 (m, 1H), 4.89 (s, 2H), 3.80-3.77 (m, 2H), 3.18-3.10 (m, 2H).

Characterization of Compounds of Class IIIa and Class IIIb

784: White solid. Yield: 58%. $^1$H NMR (500 MHz, acetone-d$_6$) δ 10.15 (br, 1H), 7.65 (d, J=8.0 Hz, 1H), 7.61-7.57 (m, 3H), 7.51 (d, J=7.5 Hz, 2H), 7.45-7.32 (m, 7H), 7.11 (t, J=7.6 Hz, 1H), 6.99 (t, J=7.5 Hz, 1H), 4.58 (d, J=5.7 Hz, 2H), 3.75 (s, 2H). HRMS (ESI) m/z Found: 408.17033 [M+H]$^+$, Calcd: 408.17065 [M+H]$^+$.

795: Colorless syrup. Yield: 65%. $^1$H NMR (500 MHz, CDCl$_3$) δ 8.30 (s, 1H), 7.67-7.51 (m, 5H), 7.40-7.28 (m, 8H), 7.18-7.13 (m, 2H), 7.05-7.01 (m, 1H), 4.72 (d, J=17.4 Hz, 1H), 4.19 (s, 2H), 3.38-3.22 (m, 4H).

874: White solid. Yield: 49%. $^1$H NMR (500 MHz, CDCl$_3$) δ 8.00 (br, 1H), 7.61 (d, J=7.8 Hz, 1H), 7.34 (d, J=8.1 Hz, 1H), 7.29-7.22 (m, 3H), 7.20-7.08 (m, 5H), 7.03 (d, J=2.1 Hz, 1H), 6.98-6.94 (m, 2H), 3.97 (s, 2H), 3.03-3.06 (m, 2H), 3.02-2.99 (m, 2H). HRMS (ESI) m/z Found: 429.18897 [M+H]$^+$, Calcd: 429.18886 [M+H]$^+$.

876: White solid. Yield: 64%. $^1$H NMR (500 MHz, CDCl$_3$) δ 11.35 (br, 1H), 8.12 (br, 1H), 7.41 (d, J=7.8 Hz, 1H), 7.37 (d, J=8.1 Hz, 1H), 7.33-7.24 (m, 4H), 7.24-7.17 (m, 3H), 7.15-7.08 (m, 2H), 7.02-6.98 (m, 1H), 6.97-6.91 (m, 1H), 4.61-4.42 (m, 4H).

1096: White solid. Yield: 86.4%. $^1$H NMR (500 MHz, CDCl$_3$) δ 7.61 (d, J=7.9 Hz, 1H), 7.29-7.20 (m, 5H), 7.19-7.08 (m, 6H), 7.03-6.92 (m, 2H), 4.06 (s, 2H), 4.01 (s, 2H) 3.70 (s, 3H).

1144: white solid. Yield: 83.2%. $^1$H NMR (500 MHz, Acetone-d$_6$) δ 11.26 (br, 1H), 10.14 (br, J=5.0 Hz, 1H), 7.65-7.59 (m, 1H), 7.56 (br, 1H), 7.45-7.17 (m, 8H), 7.11-6.98 (m, 4H), 4.48-4.39 (m, 2H), 3.72 (s, 2H). HRMS (ESI) m/z Found: 443.16855 [M+H]$^+$, Calcd: 443.16779 [M+H]$^+$.

1145: white solid. Yield: 77.3%. $^1$H NMR (500 MHz, Acetone-d$_6$) δ 510.14 (br, 1H), 7.63-7.62 (m, 1H), 7.56 (br, 1H), 7.46-7.45 (m, 4H), 7.40-7.38 (m, 1H), 7.32-7.29 (m, 5H), 7.26-7.23 (m, 2H), 7.12-7.09 (m, 1H), 7.01-6.98 (m, 1H), 4.44 (d, J=5.5 Hz, 2H), 3.72 (s, 2H).

1369: White solid. Yield: 80.1%. $^1$H NMR (500 MHz, Acetone-d$_6$) δ 7.60 (d, J=7.8 Hz, 1H), 7.51 (d, J=7.5 Hz, 5H), 7.36 (d, J=8.2 Hz, 1H), 7.31 (t, J=7.5 Hz, 4H), 7.24 (t, J=7.3 Hz, 2H), 7.18 (s, 1H), 7.09-7.06 (m, 1H), 6.98 (t, J=7.5 Hz, 1H), 4.00 (s, 2H), 3.10-3.04 (m, 2H), 3.03-2.98 (m, 2H).

1186: White solid. Yield: 89.5%. $^1$H NMR (500 MHz, Acetone-d$_6$) δ 11.48 (br, 1H), 9.99 (br, 1H), 7.57-7.55 (m, 1H), 7.48-7.43 (m, 1H), 7.41-7.27 (m, 5H), 7.23-7.18 (m, 2H), 7.15-7.12 (m, 1H), 7.08-7.04 (m, 1H), 7.01-6.92 (m, 2H), 3.99 (s, 2H), 3.96 (s, 2H), 3.07-2.99 (m, 4H). HRMS (ESI) m/z Found: 468.20018 [M+H]$^+$, Calcd: 468.19943 [M+H]$^+$.

1187: White solid. Yield: 92.1%. $^1$H NMR (500 MHz, Acetone-d$_6$) δ 11.32 (br, 1H), 9.98 (br, 1H), 7.69-7.14 (m, 13H), 7.10-7.03 (m, 1H), 6.96-6.93 (m, 1H), 3.99 (s, 2H), 3.94 (s, 2H), 3.06-2.99 (m, 4H). HRMS (ESI) m/z Found: 432.21891 [M+H]$^+$, Calcd: 432.21827 [M+H]$^+$.

1188: colorless syrup. Yield: 88.5%. $^1$H NMR (500 MHz, CDCl$_3$) δ 7.96 (br, 1H), 7.67-7.64 (m, 2H), 7.64-7.56 (m, 3H), 7.41-7.31 (m, 7H), 7.22-7.14 (m, 1H), 7.12-7.03 (m, 2H), 4.03 (s, 2H), 3.86 (s, 2H), 3.15-3.09 (m, 2H), 3.08-3.04 (m, 2H).

1076: White solid. Yield: 88.5%. $^1$H NMR (500 MHz, CDCl$_3$) δ 7.68-7.63 (m, 2H), 7.63-7.58 (m, 2H), 7.41-7.31 (m, 6H), 7.26 (d, J=9.0 Hz, 1H), 6.95 (d, J=2.9 Hz, 1H), 6.74 (dd, J=9.0, 2.9 Hz, 1H), 3.87 (s, 2H), 3.28-3.18 (m, 4H), 2.87-2.80 (m, 4H).

1077: White solid. Yield: 92.1%. $^1$H NMR (500 MHz, CDCl$_3$) δ 7.73-7.64 (m, 4H), 7.64-7.59 (m, 2H), 7.41-7.30 (m, 6H), 7.30-7.25 (m, 2H), 6.14 (br, 1H), 3.85 (s, 2H), 3.20-3.18 (m, 2H), 3.00 (d, J=4.9 Hz, 3H), 2.60-2.53 (m, 1H), 2.45-2.30 (m, 2H), 1.89-1.85 (m, 4H).

1078: White solid. Yield: 89.4%. $^1$H NMR (500 MHz, CDCl$_3$) δ 7.66-7.61 (m, 2H), 7.60-7.55 (m, 4H), 7.44 (d, J=8.0 Hz, 2H), 7.40-7.30 (m, 6H), 3.84 (s, 2H), 3.61 (s, 2H), 2.75 (br, 4H), 2.59 (br, 4H).

1079: White solid. Yield: 92.3%. $^1$H NMR (500 MHz, CDCl$_3$) δ 7.68-7.64 (m, 2H), 7.63-7.59 (m, 2H), 7.40-7.31 (m, 6H), 7.29-7.23 (m, 2H), 6.94-6.92 (m, 2H), 6.88-6.84 (m, 1H), 3.88 (s, 2H), 3.31-3.23 (m, 4H), 2.89-2.82 (m, 4H).

1080: White solid. Yield: 92.6%.$^1$H NMR (500 MHz, CDCl$_3$) δ 7.69-7.65 (m, 2H), 7.64-7.60 (m, 2H), 7.50-7.31 (m, 10H), 3.86 (s, 2H), 3.21-3.19 (m, 2H), 2.62-2.56 (m, 1H), 2.42-2.35 (m, 2H), 1.91-1.87 (m, 4H).

1089: White solid. Yield: 83.1%. $^1$H NMR (500 MHz, CDCl$_3$) δ 8.14-8.10 (m, 2H), 7.67-7.63 (m, 2H), 7.63-7.58 (m, 2H), 7.42-7.31 (m, 6H), 6.85-6.79 (m, 2H), 3.88 (s, 2H), 3.52-3.46 (m, 4H), 2.86-2.81 (m, 4H).

1090: White solid. Yield: 87.6%. $^1$H NMR (500 MHz, CDCl$_3$) δ 7.68-7.63 (m, 2H), 7.63-7.58 (m, 2H), 7.52-7.47 (m, 2H), 7.40-7.33 (m, 6H), 6.89-6.83 (m, 2H), 3.87 (s, 2H), 3.44-3.34 (m, 4H), 2.84-2.79 (m, 4H).

1091: White solid. Yield: 85.4%. $^1$H NMR (500 MHz, CDCl$_3$) δ 9.47 (br, 1H), 7.41-7.17 (m, 7H), 7.13-7.11 (m, 1H), 7.07-7.00 (m, 1H), 6.97-6.91 (m, 3H), 6.90-6.85 (m, 1H), 3.78 (s, 2H), 3.36-3.17 (m, 4H), 2.89-2.70 (m, 4H).

1092: White solid. Yield: 88.2%. $^1$H NMR (500 MHz, CDCl$_3$) δ 9.38 (br, 1H), 7.43-7.16 (m, 6H), 7.13-7.10 (m, 1H), 7.06-7.03 (m, 1H), 6.96-6.93 (m, 2H), 6.76-6.74 (m, 1H), 3.78 (s, 2H), 3.33-3.13 (m, 4H), 2.83-2.66 (m, 4H).

1093: White solid. Yield: 92.2%. $^1$H NMR (500 MHz, CDCl$_3$) δ 9.53 (br, 1H), 7.57 (d, J=8.0 Hz, 2H), 7.44 (d, J=8.0 Hz, 2H), 7.36-7.29 (m, 3H), 7.25-7.20 (m, 1H), 7.19-7.17 (m, 1H), 7.11-7.09 (m, 1H), 7.05-7.01 (m, 1H), 6.94-6.91 (m, 1H), 3.72 (s, 2H), 3.57 (s, 2H), 2.62 (br, 4H), 2.51 (br, 4H).

1094: White solid. Yield: 91.7%. $^1$H NMR (500 MHz, CDCl$_3$) δ 7.67-7.63 (m, 2H), 7.63-7.58 (m, 2H), 7.40-7.30 (m, 6H), 6.86-6.84 (m, 2H), 6.79-6.72 (m, 2H), 4.59 (br, 1H), 3.88 (s, 2H), 3.18-3.09 (m, 4H), 2.89-2.80 (m, 4H).

1097: White solid. Yield: 90.2%. $^1$H NMR (500 MHz, CDCl$_3$) δ 7.69-7.64 (m, 2H), 7.64-7.58 (m, 2H), 7.42-7.30 (m, 8H), 6.84-6.74 (m, 2H), 3.87 (s, 2H), 3.25-3.17 (m, 4H), 2.89-2.78 (m, 4H).

1098: White solid. Yield: 93.1%. $^1$H NMR (500 MHz, CDCl$_3$) δ 9.42 (br, 1H), 7.71-7.21 (m, 11H), 6.97-6.96 (m, 1H), 6.75-6.73 (m, 1H), 3.78 (s, 2H), 3.26-3.15 (m, 4H), 2.80-2.65 (m, 4H).

1099: White solid. Yield: 92.8%. $^1$H NMR (500 MHz, CDCl$_3$) δ 9.47 (br, 1H), 7.70-7.16 (m, 12H), 6.94-6.92 (m, 2H), 6.88-6.85 (m, 1H), 3.79 (s, 2H), 3.31-3.15 (m, 4H), 2.85-2.66 (m, 4H).

1100: White solid. Yield: 91.6%. $^1$H NMR (500 MHz, CDCl$_3$) δ 9.57 (br, 1H), 7.69-7.66 (m, 1H), 7.35-7.31 (m, 3H), 7.28-7.18 (m, 4H), 7.15-7.00 (m, 2H), 6.94 (s, 1H), 3.78 (s, 2H), 3.13-3.11 (m, 3H), 2.42-2.38 (m, 2H), 2.19-2.07 (m, 4H).

1101: White solid. Yield: 83.6%. $^1$H NMR (500 MHz, CDCl$_3$) δ 9.50 (br, 1H), 7.59-7.56 (m, 4H), 7.47-7.27 (m, 9H), 7.23-7.20 (m, 1H), 3.73 (s, 2H), 3.56 (s, 2H), 2.62 (s, 4H), 2.49 (s, 4H).

1102: White solid. Yield: 87.1%. $^1$H NMR (500 MHz, CDCl$_3$) δ 7.51-7.49 (m, 2H), 7.41-7.35 (m, 2H), 7.33-7.23 (m, 6H), 7.23-7.17 (m, 2H), 6.98-6.94 (m, 2H), 4.16 (s, 2H), 3.23-3.09 (m, 4H), 2.47-2.40 (m, 2H), 2.13 (s, 1H), 1.91-1.88 (m, 2H).

1103: White solid. Yield: 89.4%. $^1$H NMR (500 MHz, CDCl$_3$) δ 7.69-7.65 (m, 2H), 7.63-7.60 (m, 2H), 7.53-7.50 (m, 2H), 7.40-7.30 (m, 8H), 7.29-7.24 (m, 1H), 3.90 (s, 2H), 3.01-2.99 (m, 2H), 2.82-2.77 (m, 2H), 2.31-2.25 (m, 2H), 1.82-1.78 (m, 2H).

1104: White solid. Yield: 80.6%. $^1$H NMR (500 MHz, CDCl$_3$) δ 9.40 (br, 1H), 7.52-7.49 (m, 2H), 7.40-7.18 (m, 5H), 7.13-7.11 (m, 1H), 7.08-7.03 (m, 1H), 6.96-6.93 (m, 1H), 6.90-6.85 (m, 2H), 3.78 (s, 2H), 3.41-3.33 (m, 4H), 2.78-2.70 (m, 4H).

1120: White solid. Yield: 81.7%. $^1$H NMR (500 MHz, Acetone-d$_6$) δ 11.91 (br, 1H), 7.17-7.10 (m, 2H), 7.10-6.69 (m, 10H), 6.60-6.53 (m, 2H), 3.17 (s, 2H), 2.94-2.89 (m, 4H), 2.23-2.12 (m, 4H).

1121: White solid. Yield: 82.9%. $^1$H NMR (500 MHz, CDCl$_3$) δ 9.37 (br, 1H), 7.48-7.38 (m, 5H), 7.38-7.27 (m, 3H), 7.26-6.94 (m, 5H), 3.84 (br, 2H), 3.75 (s, 2H), 3.49 (br, 2H), 2.66-2.56 (m, 4H).

1122: White solid. Yield: 88.6%. $^1$H NMR (500 MHz, CDCl$_3$) δ 7.51-7.48 (m, 4H), 7.43-7.38 (m, 5H), 7.34-7.31 (m, 4H), 7.29-7.27 (m, 2H), 3.86 (br, 2H), 3.78 (s, 2H), 3.49 (br, 2H), 2.70-2.55 (m, 4H).

1123: Colorless syrup. Yield: 90.1%. $^1$H NMR (500 MHz, CDCl$_3$) δ 7.66-7.62 (m, 2H), 7.62-7.57 (m, 2H), 7.44-7.31 (m, 11H), 3.90-3.87 (m, 4H), 3.53 (br, 2H), 2.81 (br, 2H), 2.67 (br, 2H), 2.50 (br, 1H).

1124: Colorless syrup. Yield: 91.2%. $^1$H NMR (500 MHz, CDCl$_3$) δ 7.70-7.66 (m, 2H), 7.66-7.62 (m, 2H), 7.42-7.32 (m, 7H), 7.18-7.15 (m, 1H), 7.09-7.06 (m, 1H), 6.98-6.96 (m, 1H), 4.01 (br, 2H), 3.26 (br, 2H), 2.88-2.82 (m, 1H), 2.55 (br, 2H), 2.05 (s, 2H), 1.99 (br, 2H).

1125: White solid. Yield: 81.3%. $^1$H NMR (500 MHz, CDCl$_3$) δ 9.43 (br, 1H), 7.59-7.27 (m, 11H), 7.01-7.00 (m, 1H), 6.48-6.47 (m, 1H), 3.84 (br, 4H), 3.76 (s, 2H), 2.68-2.62 (m, 4H).

1126: Colorless syrup. Yield: 87.5%. $^1$H NMR (500 MHz, CDCl$_3$) δ 7.67-7.63 (m, 2H), 7.63-7.57 (m, 2H), 7.47-7.46 (m, 1H), 7.41-7.29 (m, 6H), 7.00-6.99 (m, 1H), 6.47-6.46 (m, 1H), 3.88 (br, 4H), 3.85 (s, 2H), 2.78-2.71 (m, 4H).

1127: Colorless syrup. Yield: 91.6%. $^1$H NMR (500 MHz, CDCl$_3$) δ 7.78 (s, 1H), 7.71-7.70 (m, 1H), 7.62-7.51 (m, 4H), 7.51-7.43 (m, 2H), 7.40-7.35 (m, 2H), 7.33-7.31 (m, 2H), 7.22-7.06 (m, 2H), 3.91 (s, 1H), 3.82 (s, 2H), 2.94-2.83 (m, 4H), 2.74-2.70 (m, 2H), 2.20-2.16 (m, 2H).

1128: White solid. Yield: 85.9%. $^1$H NMR (500 MHz, CDCl$_3$) δ 8.24-8.09 (m, 2H), 7.81-7.63 (m, 3H), 7.34-7.20 (m, 1H), 7.15-6.98 (m, 1H), 3.89 (s, 2H), 3.18-3.09 (m, 3H), 2.47-2.42 (m, 2H), 2.23-2.02 (m, 5H).

1129: White solid. Yield: 83.3%. $^1$H NMR (500 MHz, CDCl$_3$) δ 7.81 (s, 1H), 7.72-7.65 (m, 3H), 7.64-7.60 (m, 2H), 7.53-7.52 (m, 1H), 7.49-7.45 (m, 1H), 7.40-7.31 (m, 6H), 3.88 (s, 2H), 3.02-3.0 (m, 2H), 2.77-2.73 (m, 2H), 2.29-2.23 (m, 2H), 2.17 (s, 1H), 1.83-1.73 (m, 2H).

1137: White solid. Yield: 83.8%. $^1$H NMR (500 MHz, Acetone-d$_6$) δ 10.11 (br, 1H), 7.75-7.73 (m, 1H), 7.43-7.34 (m, 10H), 7.10-7.07 (m, 3H), 7.02-6.98 (m, 1H), 4.62 (s, 2H), 3.75-3.63 (m, 2H), 3.45-3.40 (m, 2H), 2.48-2.29 (m, 5H).

1139: White solid. Yield: 88.1%. $^1$H NMR (500 MHz, Acetone-d$_6$) δ 11.52 (br, 1H), 7.78 (br, 1H), 7.49-7.21 (m, 5H), 7.14-7.11 (m, 1H), 6.99-6.96 (m, 1H), 6.89-6.79 (m, 2H), 6.79-6.66 (m, 2H), 3.70 (s, 2H), 3.10-2.98 (m, 4H), 2.84 (br, 1H), 2.73-2.63 (m, 4H).

1140: White solid. Yield: 86.5%. $^1$H NMR (500 MHz, CDCl$_3$) δ 12.99 (s, 1H), 7.63 (d, J=8.3 Hz, 2H), 7.47-7.44 (m, 1H), 7.24-7.19 (m, 3H), 7.17-7.09 (m, 5H), 6.85 (s, 2H), 3.88 (s, 2H), 3.35-3.33 (m, 2H), 3.04 (d, J=4.9 Hz, 3H), 2.55-2.51 (m, 1H), 2.45-2.40 (m, 2H), 1.84-1.81 (m, 2H), 1.35-1.21 (m, 2H).

1141: White solid. Yield: 87.6%. $^1$H NMR (500 MHz, CDCl$_3$) δ 9.51 (br, 1H), 7.37-7.30 (m, 3H), 7.28-7.22 (m, 1H), 7.22-7.14 (m, 2H), 7.12-7.10 (m, 1H), 7.06-7.02 (m, 1H), 6.95-6.92 (m, 1H), 6.55-6.53 (m, 1H), 6.48-6.40 (m, 2H), 3.79 (s, 3H), 3.77 (s, 2H), 3.29-3.19 (m, 4H), 2.79-2.69 (m, 4H).

1142: White solid. Yield: 91.4%. $^1$H NMR (500 MHz, CDCl$_3$) δ 7.69-7.63 (m, 2H), 7.63-7.58 (m, 2H), 7.40-7.30 (m, 6H), 7.20-7.14 (m, 1H), 6.56-6.52 (m, 1H), 6.47-6.46 (m, 1H), 6.44-6.39 (m, 1H), 3.87 (s, 2H), 3.78 (s, 3H), 3.29-3.21 (m, 4H), 2.87-2.79 (m, 4H).

1143: White solid. Yield: 82.6%. $^1$H NMR (500 MHz, CDCl$_3$) δ 9.48 (br, 1H), 7.51 (br, 4H), 7.39-7.23 (m, 6H), 7.19-7.16 (m, 1H), 6.55-6.53 (m, 1H), 6.52-6.40 (m, 2H), 3.79 (s, 2H), 3.79 (s, 3H), 3.32-3.18 (m, 4H), 2.81-2.71 (m, 4H).

1173: White solid. Yield: 77.4%. $^1$H NMR (500 MHz, Acetone-d$_6$) δ 11.51 (br, 1H), 7.47-7.43 (m, 1H), 7.41-7.28 (m, 6H), 7.26-7.23 (m, 1H), 7.15-7.11 (m, 1H), 7.00-6.96 (m, 1H), 6.92-6.88 (m, 2H), 3.71 (s, 2H), 3.22-3.16 (m, 4H), 2.82 (br, 1H), 2.73-2.67 (m, 4H).

1174: White solid. Yield: 88.2%. $^1$H NMR (500 MHz, Acetone-d$_6$) δ 11.57 (br, 1H), 7.69-7.21 (m, 8H), 7.17-6.75 (m, 4H), 3.73 (s, 2H), 3.29-3.14 (m, 4H), 2.77-2.66 (m, 4H).

1175: White solid. Yield: 80.5%. $^1$H NMR (500 MHz, Acetone-d$_6$) δ 11.46 (br, 1H), 7.46-7.42 (m, 1H), 7.40-7.27 (m, 8H), 7.26-7.20 (m, 2H), 7.14-7.10 (m, 1H), 6.98-6.95 (m, 1H), 3.64 (s, 2H), 3.48 (s, 2H), 2.56 (br, 4H), 2.44 (br, 4H).

1176: Colorless syrup. Yield: 92.5%. $^1$H NMR (500 MHz, CDCl$_3$) δ 7.66-7.61 (m, 2H), 7.61-7.57 (m, 2H), 7.40-7.29 (m, 10H), 7.25-7.22 (m, 1H), 3.82 (s, 2H), 3.52 (s, 2H), 2.71 (br, 4H), 2.54 (br, 4H). HRMS (ESI) m/z Found: 410.22416 [M+H]$^+$, Calcd: 410.22269 [M+H]$^+$.

1177: White solid. Yield: 79.3%. $^1$H NMR (500 MHz, Acetone-d$_6$) δ 11.47 (br, 1H), 7.57-7.19 (m, 10H), 7.12 (br, 1H), 6.96 (br, 1H), 3.64 (s, 2H), 3.48 (s, 2H), 2.56 (br, 4H), 2.44 (br, 4H).

1178: White solid. Yield: 82.4%. $^1$H NMR (500 MHz, Acetone-d$_6$) δ 11.55 (br, 1H), 7.57-6.96 (m, 12H), 3.76 (br, 2H), 3.73 (s, 2H), 3.36-3.34 (m, 2H), 2.67-2.65 (m, 2H), 2.57 (br, 2H).

1179: White solid. Yield: 86.9%. $^1$H NMR (500 MHz, Acetone-d$_6$) δ 11.52 (br, 1H), 7.56-6.92 (m, 12H), 3.71-3.62 (m, 4H), 3.45 (br, 2H), 2.60 (br, 4H).

1180: Colorless syrup. Yield: 91.3%. $^1$H NMR (500 MHz, CDCl$_3$) δ 7.67-7.63 (m, 2H), 7.61-7.59 (m, 2H), 7.47-7.30 (m, 8H), 7.11-7.05 (m, 2H), 3.86-3.75 (m, 4H), 3.51 (br, 2H), 2.75-2.65 (m, 4H).

1181: White solid. Yield: 86.2%. $^1$H NMR (500 MHz, Acetone-d$_6$) δ 11.51 (br, 1H), 8.04 (br, 1H), 7.51-7.21 (m, 6H), 7.18-7.10 (m, 1H), 7.06-6.94 (m, 2H), 6.46-6.38 (m, 2H), 6.29-6.27 (m, 1H), 3.70 (s, 2H), 3.17-3.12 (m, 4H), 2.71-2.65 (m, 4H).

1182: White solid. Yield: 88.1%. $^1$H NMR (500 MHz, CDCl$_3$) δ 7.69-7.62 (m, 2H), 7.60-7.58 (m, 2H), 7.39-7.28 (m, 6H), 7.10-7.06 (m, 1H), 6.50-6.48 (m, 1H), 6.38 (s, 1H), 6.31-6.29 (m, 1H), 5.55 (br, 1H), 3.86 (s, 2H), 3.25-3.18 (m, 4H), 2.85-2.78 (m, 4H).

1183: White solid. Yield: 85.4%. $^1$H NMR (500 MHz, Acetone-d$_6$) δ 11.51 (br, 1H), 7.53-7.22 (m, 7H), 7.18-7.09 (m, 2H), 6.99-6.95 (m, 2H), 6.87-6.75 (m, 2H), 3.73 (s, 2H), 2.94-2.93 (m, 4H), 2.76 (br, 4H).

1184: White solid. Yield: 87.9%. $^1$H NMR (500 MHz, CDCl$_3$) δ 7.69-7.60 (m, 4H), 7.42-7.31 (m, 7H), 7.19-7.17 (m, 1H), 7.08-7.06 (m, 1H), 6.95-6.93 (m, 1H), 6.88-6.85 (m, 1H), 3.90 (s, 2H), 2.98-2.97 (m, 4H), 2.87 (Br, 4H).

1209: White solid. Yield: 85.4. $^1$H NMR (500 MHz, Acetone-d$_6$) δ 11.48 (br, 1H), 7.88 (s, 1H), 7.81-7.79 (m, 1H), 7.57-7.56 (m, 2H), 7.44-6.97 (m, 8H), 4.19 (s, 1H), 3.74 (s, 2H), 2.87-2.85 (m, 2H), 2.75-2.70 (m, 2H), 2.17-2.11 (m, 2H), 1.75-1.72 (m, 2H).

1210: White solid. Yield: 87.9%. $^1$H NMR (500 MHz, Acetone-d$_6$) δ 11.34 (br, 1H), 7.65-7.44 (m, 6H), 7.42-7.11 (m, 8H), 3.99 (br, 1H), 3.70 (s, 2H), 2.85-2.81 (m, 4H), 2.71-2.66 (m, 2H), 1.70-1.68 (m, 2H).

1211: White solid. Yield: 91.8%. $^1$H NMR (500 MHz, Acetone-d$_6$) δ 12.16 (br, 1H), 7.52-7.47 (m, 8H), 7.45-7.44 (m, 3H), 7.18-7.15 (m, 2H), 7.11-7.08 (m, 1H), 3.93 (s, 2H), 3.01 (d, J=11.1 Hz, 2H), 2.74-2.69 (m, 2H), 1.84-1.78 (m, 2H), 1.71-1.60 (m, 2H).

1212: White solid. Yield: 88.7%. $^1$H NMR (500 MHz, Acetone-d$_6$) δ 7.45-7.29 (m, 6H), 7.08-7.01 (m, 2H), 6.87-6.82 (m, 2H), 6.79-6.72 (m, 2H), 4.65 (s, 1H), 3.87 (s, 2H), 3.17-3.10 (m, 4H), 2.85-2.81 (m, 4H).

1213: White solid. Yield: 91.2%. $^1$H NMR (500 MHz, CDCl$_3$) δ 7.45-7.22 (m, 8H), 7.10-7.01 (m, 2H), 6.94-6.93 (m, 2H), 6.88-6.85 (m, 1H), 3.87 (s, 2H), 3.32-3.21 (m, 4H), 2.91-2.80 (m, 4H).

1214 Colorless syrup. Yield: 77.4%. $^1$H NMR (500 MHz, CDCl$_3$) δ $^1$H NMR (500 MHz, CDCl$_3$) δ 7.98 (br, 1H), 7.67-7.65 (m, 1H), 7.47-7.33 (m, 7H), 7.21-7.18 (m, 1H), 7.13-7.04 (m, 3H), 7.00-6.98 (m, 1H), 3.89 (s, 2H), 3.21-3.18 (m, 2H), 2.91-2.82 (m, 1H), 2.48-2.44 (m, 2H), 2.12-2.10 (m, 2H), 1.97-1.92 (m, 2H).

1227: White solid. Yield: 86.4%. $^1$H NMR (500 MHz, CDCl$_3$) δ 8.20-8.18 (m, 1H), 7.70-7.58 (m, 4H), 7.50-7.44 (m, 1H), 7.42-7.29 (m, 6H), 6.69-6.58 (m, 2H), 3.87 (s, 2H), 3.66-3.55 (m, 4H), 2.81-2.78 (m, 4H).

1228: Colorless syrup. Yield: 89.7%. $^1$H NMR (500 MHz, CDCl$_3$) δ 8.00 (br, 1H), 7.68-7.64 (m, 1H), 7.62-7.59 (m, 2H), 7.45-7.39 (m, 1H), 7.38-7.33 (m, 1H), 7.31-7.28 (m, 1H), 7.24-7.17 (m, 1H), 7.15-7.10 (m, 2H), 4.08 (s, 2H), 3.88 (s, 2H), 3.20-2.94 (m, 4H).

1229: White solid. Yield: 89.1%. $^1$H NMR (500 MHz, CDCl$_3$) δ 8.20 (d, J=5.2 Hz, 1H), 7.69-7.58 (m, 4H), 7.44-7.30 (m, 6H), 6.52 (d, J=5.2 Hz, 1H), 3.84 (s, 2H), 3.19-3.16 (m, 2H), 2.53-2.42 (m, 1H), 2.38-2.32 (m, 2H), 1.94-1.81 (m, 4H), 1.65 (br, 2H).

1284: White solid. Yield: 81.2%. $^1$H NMR (500 MHz, CDCl$_3$) δ 9.70 (br, 1H), 8.56-8.55 (m, 1H), 7.67-7.63 (m, 1H), 7.58-7.42 (br, 3H), 7.40 (d, J=7.8 Hz, 1H), 7.39-7.20 (m, 6H), 7.18-7.15 (m, 1H), 3.73 (s, 2H), 3.67 (s, 2H), 2.65 (s, 4H), 2.56 (s, 4H).

1285: Colorless syrup. Yield: 82.5%. $^1$H NMR (500 MHz, CDCl$_3$) δ 8.56 (d, J=4.2 Hz, 1H), 7.68-7.56 (m, 5H), 7.42-7.30 (m, 7H), 7.17-7.14 (m, 1H), 3.83 (s, 2H), 3.69 (s, 2H), 2.75 (br, 4H), 2.62 (br, 4H).

1286: Colorless syrup. Yield: 87.5%. $^1$H NMR (500 MHz, CDCl$_3$) δ 7.71-7.62 (m, 2H), 7.62-7.56 (m, 2H), 7.41-7.29 (m, 6H), 7.29-7.20 (m, 1H), 7.13-7.04 (m, 2H), 6.95-6.91 (m, 1H), 3.82 (s, 2H), 3.51 (s, 2H), 2.72 (br, 4H), 2.54 (br, 4H).

1287: Colorless syrup. Yield: 84.3%. $^1$H NMR (500 MHz, CDCl$_3$) δ 7.66-7.62 (m, 2H), 7.62-7.57 (m, 2H), 7.41-7.30 (m, 6H), 7.24-7.18 (m, 2H), 6.87-6.82 (m, 2H), 3.81 (s, 2H), 3.79 (s, 3H), 3.46 (s, 2H), 2.70 (br, 4H), 2.52 (br, 4H).

1288: Colorless syrup. Yield: 91.2%. $^1$H NMR (500 MHz, CDCl$_3$) δ 7.65-7.63 (m, 2H), 7.62-7.57 (m, 2H), 7.42-7.29 (m, 6H), 7.29-7.22 (m, 1H), 7.08-7.05 (m, 2H), 6.98-6.89 (m, 1H), 3.82 (s, 2H), 3.52 (s, 2H), 2.72 (br, 4H), 2.54 (br, 4H).

1289: White solid. Yield: 88.5%. $^1$H NMR (500 MHz, CDCl$_3$) δ 7.67-7.62 (m, 2H), 7.62-7.57 (m, 2H), 7.41-7.30 (m, 6H), 7.21 (t, J=7.9 Hz, 1H), 6.90-6.89 (m, 2H), 6.81-6.76 (m, 1H), 3.81 (s, 2H), 3.80 (s, 3H), 3.50 (s, 2H), 2.71 (br, 4H), 2.54 (br, 4H).

1290: White solid. Yield: 91.0%. $^1$H NMR (500 MHz, CDCl$_3$) δ 9.58 (br, 1H), 7.39-7.22 (m, 5H), 7.16 (d, J=7.6 Hz, 1H), 7.11-6.99 (m, 4H), 6.96-6.92 (m, 2H), 3.71 (s, 2H), 3.51 (s, 2H), 2.62 (br, 4H), 2.49 (br, 4H).

1291: White solid. Yield: 88.2%. $^1$H NMR (500 MHz, CDCl$_3$) δ 9.61 (br, 1H), 7.32 (br, 3H), 7.24-6.90 (m, 7H), 6.89-6.82 (m, 2H), 3.80 (s, 3H), 3.70 (s, 2H), 3.46 (s, 2H), 2.60 (br, 4H), 2.47 (br, 4H).

1312: White solid. Yield: 91.5%. $^1$H NMR (500 MHz, Acetone-d$_6$) δ 11.56 (br, 1H), 7.52-6.92 (m, 9H), 6.76-6.74 (m, 1H), 6.68-6.64 (m, 1H), 6.55-6.46 (m, 1H), 3.72 (s, 2H), 3.27-3.20 (m, 4H), 2.77-2.65 (m, 4H).

1313: Colorless syrup. Yield: 87.5%. $^1$H NMR (500 MHz, CDCl$_3$) δ 7.70-7.57 (m, 4H), 7.47-7.31 (m, 6H), 7.22-7.15 (m, 1H), 6.68-6.66 (m, 1H), 6.64-6.47 (m, 2H), 3.87 (s, 2H), 3.31-3.20 (m, 4H), 2.87-2.78 (m, 4H).

1314: White solid. Yield: 89.3%. $^1$H NMR (500 MHz, Acetone-d$_6$) δ 11.36 (br, 1H), 7.69-7.12 (m, 11H), 6.76-6.74 (m, 1H), 6.68-6.65 (m, 1H), 6.51-6.47 (m, 1H), 3.70 (s, 2H), 3.29-3.21 (m, 4H), 2.75-2.67 (m, 4H).

1315: White solid. Yield: 87.6%. $^1$H NMR (500 MHz, Acetone-d$_6$) δ 11.30 (br, 1H), 7.82-7.09 (m, 15H), 3.63 (s, 2H), 3.48 (s, 2H), 2.56 (br, 4H), 2.44 (br, 4H).

1357: White solid. Yield: 92.1%. $^1$H NMR (500 MHz, CDCl$_3$) δ 7.65-7.61 (m, 2H), 7.61-7.56 (m, 2H), 7.39-7.30 (m, 7H), 7.25-7.20 (m, 1H), 7.11-7.07 (m, 1H), 7.05-6.99 (m, 1H), 3.81 (s, 2H), 3.62 (s, 2H), 2.72 (br, 4H), 2.59 (br, 4H).

1358: White solid. Yield: 88.5%. $^1$H NMR (500 MHz, Acetone-d$_6$) δ 11.28 (br, 1H), 7.60-7.58 (m, 2H), 7.48-7.41 (m, 3H), 7.39-7.21 (m, 6H), 7.20-7.14 (m, 2H), 7.10-7.05 (m, 1H), 3.62 (s, 2H), 3.55 (s, 2H), 2.56 (br, 4H), 2.48 (br, 4H).

1359: Colorless syrup. Yield: 77.3%. $^1$H NMR (500 MHz, CDCl$_3$) δ 7.63 (s, 1H), 7.57-7.55 (m, 2H), 7.51-7.47 (m, 4H), 7.45-7.42 (m, 1H), 7.35-7.29 (m, 4H), 7.29-7.24 (m, 3H), 3.97 (s, 2H), 3.57 (s, 2H), 2.82 (br, J=4.9 Hz, 4H), 2.59 (br, 4H).

1360: Colorless syrup. Yield: 91.5%. $^1$H NMR (500 MHz, CDCl$_3$) δ 7.67-7.63 (m, 3H), 7.62-7.58 (m, 2H), 7.58-7.52 (m, 2H), 7.43-7.30 (m, 7H), 3.82 (s, 2H), 3.54 (s, 2H), 2.71 (br, 4H), 2.53 (br, 4H).

1361: Colorless syrup. Yield: 82.1%. $^1$H NMR (500 MHz, CDCl$_3$) δ 7.66-7.62 (m, 2H), 7.62-7.58 (m, 4H), 7.45-7.44 (m, 2H), 7.39-7.31 (m, 6H), 3.82 (s, 2H), 3.56 (s, 2H), 2.71 (br, 4H), 2.53 (br, 4H).

1362: Colorless syrup. Yield: 85.2%. $^1$H NMR (500 MHz, CDCl$_3$) δ 7.64-7.60 (m, 2H), 7.51-7.42 (m, 6H), 7.35-7.29 (m, 4H), 7.29-7.24 (m, 3H), 3.97 (s, 2H), 3.60 (s, 2H), 2.81 (br, 4H), 2.59 (br, 4H).

1363: Colorless syrup. Yield: 89.5%. $^1$H NMR (500 MHz, CDCl$_3$) δ 9.49 (br, 1H), 7.65-7.63 (m, 1H), 7.56-7.55 (m, 3H), 7.51-7.27 (m, 8H), 3.71 (s, 4H), 2.63 (br, 4H), 2.57 (br, 4H).

1364: Colorless syrup. Yield: 77.3%. $^1$H NMR (500 MHz, CDCl$_3$) δ 7.67-7.62 (m, 3H), 7.62-7.58 (m, 2H), 7.54-7.53 (m, 2H), 7.39-7.30 (m, 7H), 3.81 (s, 2H), 3.73 (s, 2H), 2.71 (s, 4H), 2.61 (s, 4H).

1366: Colorless syrup. Yield: 82.8%. $^1$H NMR (500 MHz, CDCl$_3$) δ 8.39-8.38 (m, 1H), 7.66-7.62 (m, 2H), 7.61-7.57 (m, 2H), 7.43-7.42 (m, 1H), 7.40-7.29 (m, 6H), 7.10-7.07 (m, 1H), 3.80 (s, 2H), 3.66 (s, 2H), 2.69 (br, 4H), 2.60 (br, 4H).

1367: White solid. Yield: 73.5%. $^1$H NMR (500 MHz, CDCl$_3$) δ 9.68 (br, 1H), 8.39-8.38 (m, 1H), 7.62-7.40 (m, 5H), 7.39-7.22 (m, 6H), 7.10 (dd, J=7.6, 4.8 Hz, 1H), 3.73 (s, 2H), 3.66 (s, 2H), 2.61 (br, 4H), 2.56 (br, 4H).

1368: Colorless syrup. Yield: 81.2%. $^1$H NMR (500 MHz, CDCl$_3$) δ 8.01-7.99 (m, 2H), 7.60-7.54 (m, 4H), 7.50-7.43 (m, 3H), 7.40-7.29 (m, 6H) 3.86 (s, 2H), 3.81 (s, 2H), 2.73 (br, 4H), 2.64 (br, 4H).

1369: White solid. Yield: 80.1%. $^1$H NMR (500 MHz, Acetone-d$_6$) δ 7.60 (d, J=7.8 Hz, 1H), 7.51 (d, J=7.5 Hz, 5H), 7.36 (d, J=8.2 Hz, 1H), 7.31 (t, J=7.5 Hz, 4H), 7.24 (t, J=7.3 Hz, 2H), 7.18 (s, 1H), 7.09-7.06 (m, 1H), 6.98 (t, J=7.5 Hz, 1H), 4.00 (s, 2H), 3.10-3.04 (m, 2H), 3.03-2.98 (m, 2H).

1370: Colorless syrup. Yield: 86.0%. $^1$H NMR (500 MHz, CDCl$_3$) δ 7.66-7.62 (m, 2H), 7.61-7.57 (m, 2H), 7.39-7.29 (m, 6H), 3.82 (s, 2H), 3.50 (t, J=5.6 Hz, 2H), 3.33 (s, 3H), 2.74 (s, 4H), 2.65-2.55 (m, 6H).

1371: Colorless syrup. Yield: 89.3%. $^1$H NMR (500 MHz, CDCl$_3$) δ 9.66 (br, 1H), 7.66-7.19 (m, 10H), 3.73 (s, 2H), 3.54-3.46 (m, 2H), 3.35 (t, J=3.3 Hz, 3H), 2.66 (s, 4H), 2.60-2.50 (m, 6H).

1372: White solid. Yield: 83.5%. $^1$H NMR (500 MHz, CDCl$_3$) δ 7.93 (br, 1H), 7.69-7.65 (m, 2H), 7.64-7.57 (m, 3H), 7.40-7.30 (m, 7H), 7.16-7.13 (m, 1H), 7.05-7.03 (m, 1H), 7.02-6.98 (m, 1H), 6.01-5.93 (m, 1H), 5.36-5.17 (m, 2H), 4.04 (s, 2H), 3.41 (d, J=6.5 Hz, 2H), 3.11-2.92 (m, 4H).

1394: White solid. Yield: 81.0%. $^1$H NMR (500 MHz, CDCl$_3$) δ 7.67-7.61 (m, 2H), 7.60-7.58 (m, 2H), 7.39-7.27 (m, 8H), 7.12 (t, J=8.0 Hz, 1H), 3.79 (s, 2H), 3.78 (s, 2H), 2.68 (br, 8H).

1395: White solid. Yield: 83.7%. $^1$H NMR (500 MHz, CDCl$_3$) δ 7.66-7.61 (m, 2H), 7.60-7.58 (m, 2H), 7.41-7.29 (m, 6H), 7.19 (d, J=7.9 Hz, 2H), 7.11 (d, J=7.9 Hz, 2H), 3.81 (s, 2H), 3.50 (s, 2H), 2.71 (br, 4H), 2.54 (br, 4H), 2.32 (s, 3H).

1396: Colorless syrup. Yield: 82.1%. $^1$H NMR (500 MHz, CDCl$_3$) δ 8.72 (br, 1H), 7.85 (br, 1H), 7.51-7.48 (m, 1H), 7.35-7.16 (m, 11H), 7.16-7.09 (m, 1H), 7.02-6.99 (m, 2H), 6.92-6.66 (m, 3H), 3.83 (s, 2H), 3.82 (s, 2H), 3.04-3.02 (m, 2H), 2.99-2.96 (m, 2H).

1397: Colorless syrup. Yield: 77.2%. $^1$H NMR (500 MHz, CDCl$_3$) δ 13.32 (br, 1H), 7.52-7.43 (m, 9H), 7.37-7.28 (m, 5H), 7.21-7.03 (m, 3H), 5.81-5.73 (m, 1H), 5.34-5.17 (m, 2H), 4.06 (s, 2H), 3.47 (d, J=7.0 Hz, 2H), 3.09-3.06 (m, 2H), 2.92-2.89 (m, 2H).

1039: Yellow syrup. Yield: 91.5%. $^1$H NMR (500 MHz, CDCl$_3$) δ 9.71 (br, 1H), 7.89-7.84 (m, 2H), 7.70-7.61 (m, 2H), 7.61-7.50 (m, 1H), 7.37-7.24 (m, 4H), 7.17 (d, J=8.8 Hz, 1H), 7.13-6.93 (m, 5H), 6.81 (dd, J=8.8, 2.4 Hz, 1H), 4.69 (s, 2H), 3.81-3.77 (m, 2H), 3.77 (s, 3H), 3.09-3.02 (m, 2H).

1040: Yellow syrup. Yield: 93.1%. $^1$H NMR (500 MHz, CDCl$_3$) δ 8.14 (s, 1H), 8.00 (d, J=7.7 Hz, 1H), 7.77-7.61 (m, 3H), 7.57 (s, 1H), 7.25-7.10 (m, 6H), 7.03-6.90 (m, 6H), 6.46 (s, 1H), 4.76 (s, 2H), 4.60 (s, 2H).

Other preferred embodiments of the compounds of the invention have a general formula A or B illustrated below.

A

B

Other preferred embodiments of the compounds of the invention have a general formula A1 or B1 illustrated below.

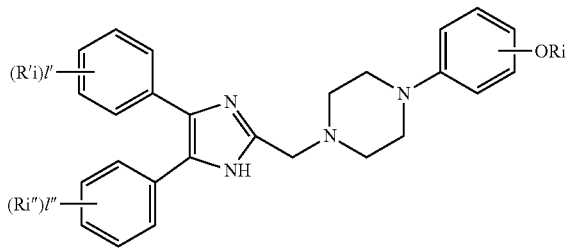

A1

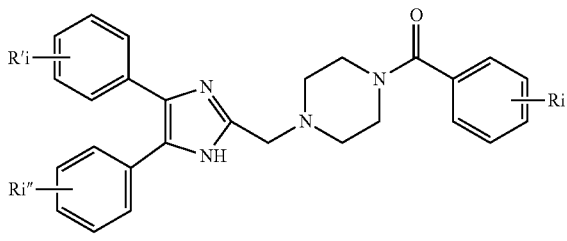

B1

Examples of such compounds are outlined in Table 5 below.

The general chemical syntheses are as follows:

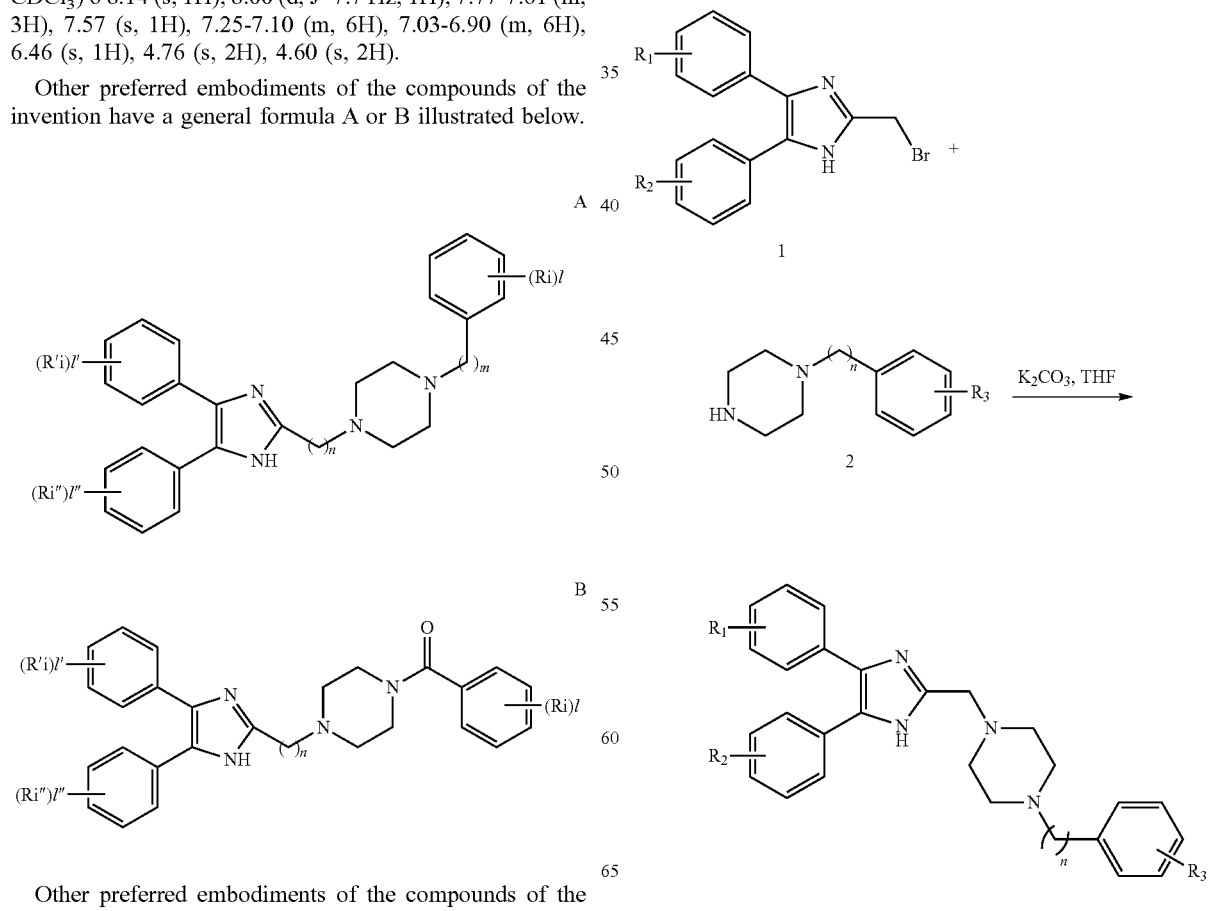

Scheme 1 Synthesis of compounds 1924, 1926 and 1928.

Scheme 2 Synthesis of compounds 1931-1934, 1937-1940, 1946 and 1949.

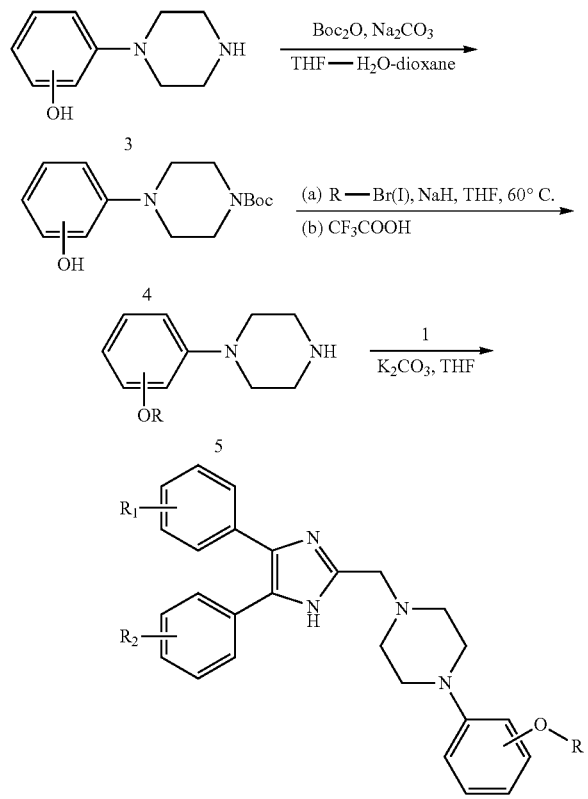

General procedure for the preparation of intermediate 4: To a mixture of N-hydroxyphenylpiperazine (2 mmol) and $NaHCO_3$ in 50 mL $THF/H_2O$/dioxane (1:1:1), $Boc_2O$ (2.4 mmol) was added and stirred at room temperature overnight. The reaction mixture was extracted with $CH_2Cl_2$. The organic layer was washed with brine, dried over $Na_2SO_4$ and concentrated in vacuo. The residue was purified by flash column chromatography on silica gel to afford the desired product 4.

General procedure for the preparation of intermediate 5: To a solution of Boc-protected intermediate 4 (1 mmol) in anhydrous THF, NaH (1.4 mmol) was added slowly at 0° C. and stirred for 30 minutes. Then bromide or iodide (2 mmol) was added and the resulting mixture was stirred at 60° C. overnight. The reaction mixture was extracted with $CH_2Cl_2$. The organic layer was washed with brine, dried over $Na_2SO_4$ and concentrated in vacuo. The residue was then dissolved in $CF_3COOH$ and stirred at room temperature for 1 hour. The reaction mixture was diluted with ethyl acetate. Washed with saturated $NaHCO_3$ solution and brine, dried over $Na_2SO_4$ and concentrated in vacuo. The residue was purified by flash column chromatography on silica gel to afford the desired product 5.

General procedure for the preparation of compounds 1924, 1926, 1928, 1931-1940, 1946 and 1949: A mixture of piperazine 2 or 5 (1.3 mmol), anhydrous $K_2CO_3$ (3 mmol) and bromide 1 (1 mmol) in anhydrous THF was stirred at 60° C. overnight. The reaction mixture was extracted with $CH_2Cl_2$. The organic layer was washed with brine, dried over $Na_2SO_4$ and concentrated in vacuo. The residue was purified by flash column chromatography on silica gel to afford the desired product 1924, 1926, 1928 and 1931-1949.

TABLE 5

1924

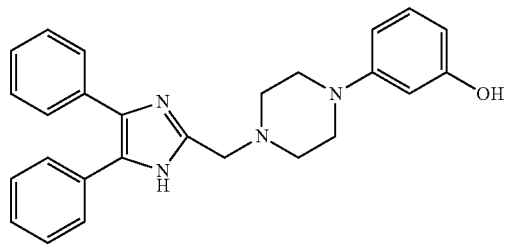 [SMILES: Oc1cccc(N2CCN(Cc3nc(-c4ccccc4)c(-c4ccccc4)[nH]3)CC2)c1]

1926

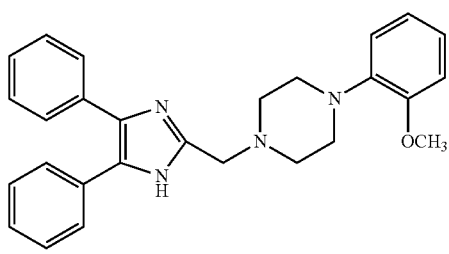 [SMILES: COc1ccccc1N1CCN(Cc2nc(-c3ccccc3)c(-c3ccccc3)[nH]2)CC1]

TABLE 5-continued
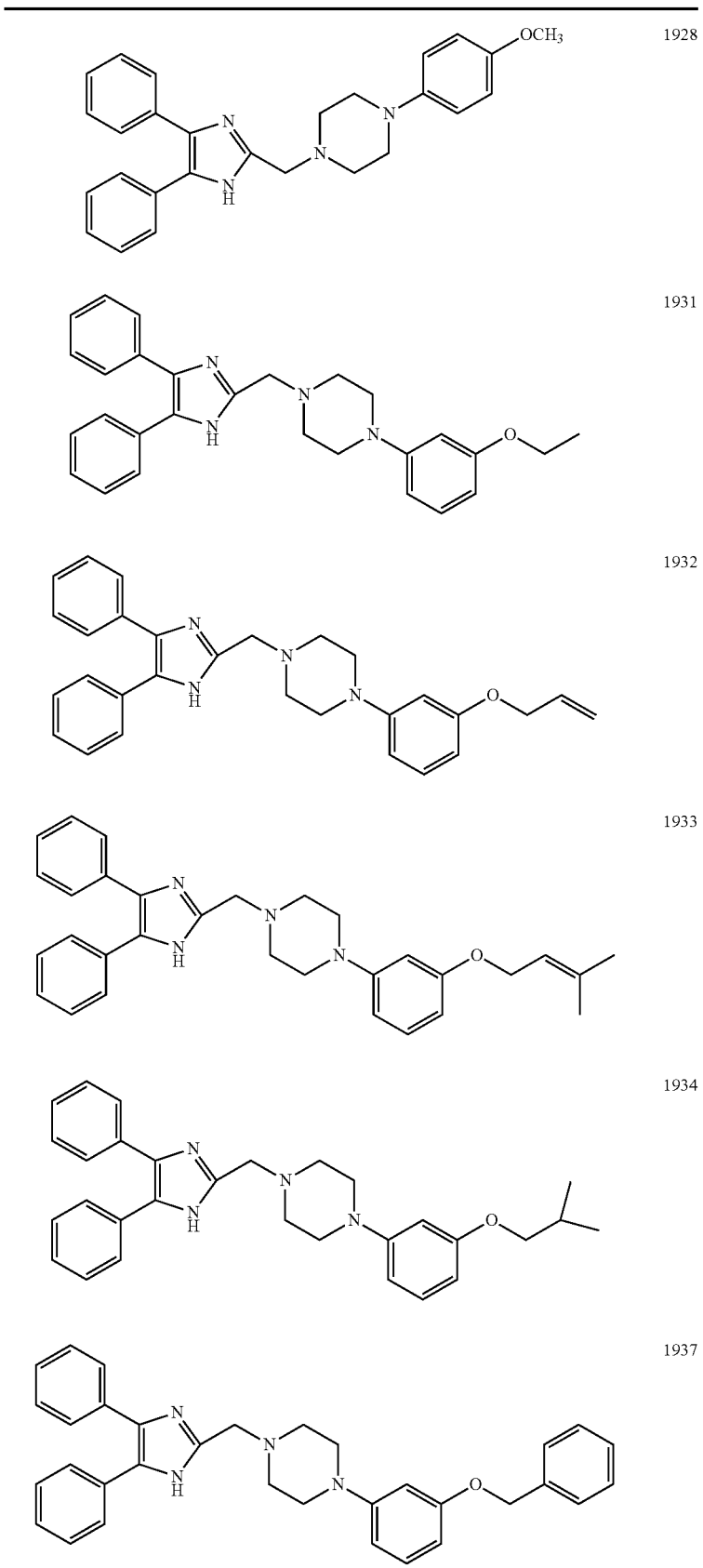

TABLE 5-continued
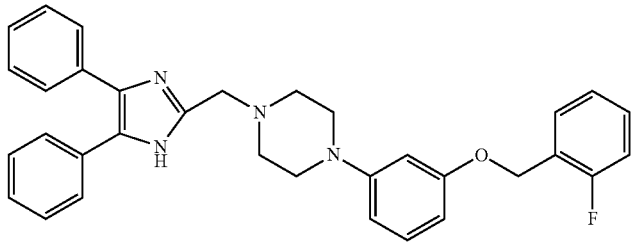 [SMILES: c1ccc(COc2cccc(N3CCN(Cc4nc(-c5ccccc5)c(-c5ccccc5)[nH]4)CC3)c2)cc1]
1938
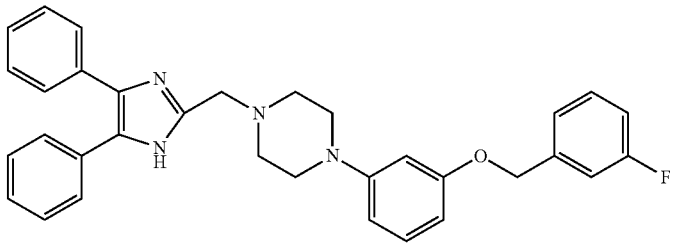 [SMILES: Fc1cccc(COc2cccc(N3CCN(Cc4nc(-c5ccccc5)c(-c5ccccc5)[nH]4)CC3)c2)c1]
1939
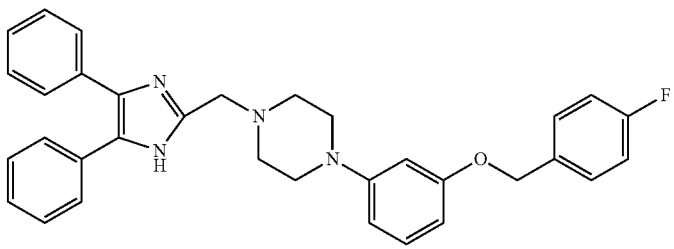 [SMILES: Fc1ccc(COc2cccc(N3CCN(Cc4nc(-c5ccccc5)c(-c5ccccc5)[nH]4)CC3)c2)cc1]
1940
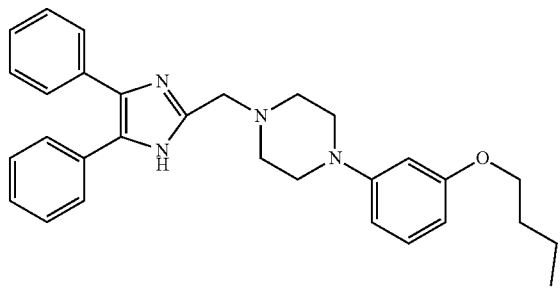 [SMILES: CCCCOc1cccc(N2CCN(Cc3nc(-c4ccccc4)c(-c4ccccc4)[nH]3)CC2)c1]
1946
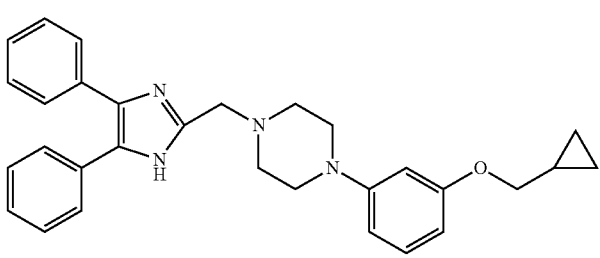 [SMILES: c1ccc(-c2nc(CN3CCN(c4cccc(OCC5CC5)c4)CC3)[nH]c2-c2ccccc2)cc1]
1949
Characterization of Compounds 1924, 1926, 1928, 1931-1934, 1937-1940, 1946 and 1949
1924: White solid, yield: 82.4%. $^1$H NMR (400 MHz, CDCl$_3$) δ 10.11 (br, 1H), 7.50-7.26 (m, 7H), 7.11-6.97 (m, 12H), 6.44-6.23 (m, 3H), 3.71 (s, 2H), 3.12-3.03 (m, 4H), 2.66-2.62 (m, 4H).
1926: White solid, yield: 82.4%. $^1$H NMR (400 MHz, CDCl$_3$) δ 9.75 (br, 1H), 7.72-7.17 (m, 10H), 7.05-6.84 (m, 4H), 3.86 (s, 3H), 3.80 (s, 2H), 3.14-3.07 (m, 4H), 2.87-2.75 (m, 4H).
1928: White solid, yield: 87.3%. $^1$H NMR (400 MHz, CDCl$_3$) δ 9.50 (br, 1H), 7.70-7.17 (m, 10H), 6.98-6.79 (m, 4H), 3.78 (s, 2H), 3.77 (s, 3H), 3.17-3.07 (m, 4H), 2.82-2.71 (m, 4H).
1931: White solid, yield: 79.5%. $^1$H NMR (400 MHz, CDCl$_3$) δ 9.65 (br, 1H), 7.71-7.22 (m, 9H), 7.16 (t, J=8.2 Hz, 1H), 6.66-6.23 (m, 3H), 4.02 (q, J=7.0 Hz, 2H), 3.77 (s, 2H), 3.27-3.16 (m, 4H), 2.81-2.67 (m, 4H), 1.47-1.36 (t, J=7.0 Hz, 3H).
1932: White solid, yield: 83.4%. $^1$H NMR (400 MHz, CDCl$_3$) δ 9.59 (br, 1H), 7.64-7.09 (m, 11H), 6.56-6.39 (m, 3H), 6.12-5.98 (m, 1H), 5.46-5.37 (m, 1H), 5.29-5.22 (m, 1H), 4.55-4.47 (m, 2H), 3.81-3.75 (m, 2H), 3.21 (m, 4H), 2.77-2.70 (m, 4H).

1933: Color syrup, yield: 67.5%. $^1$H NMR (400 MHz, CDCl$_3$) δ 9.47 (br, 1H), 7.68-7.12 (m, 11H), 6.95-6.83 (m, 1H), 6.62-6.29 (m, 3H), 3.79-3.77 (m, 2H), 3.70 (s, 2H), 3.22-3.16 (m, 4H), 2.78-2.70 (m, 4H), 1.60-1.52 (m, 6H).

1934: Color syrup, yield: 67.5%. $^1$H NMR (400 MHz, CDCl$_3$) δ 9.62 (br, 1H), 8.06-7.31 (m, 10H), 7.24-7.16 (m, 1H), 6.62-6.36 (m, 3H), 4.62-4.45 (m, 2H), 3.90-3.76 (m, 2H), 3.30-3.13 (m, 4H), 2.86-2.67 (m, 4H), 1.84-1.80 (m, 1H), 0.92-0.88 (m, 6H).

1937: White solid, yield: 83.9%. $^1$H NMR (400 MHz, CDCl$_3$) δ 9.64 (br, 1H), 7.75-7.08 (m, 16H), 6.63-6.45 (m, 3H), 5.06 (s, 2H), 3.79 (s, 2H), 3.28-3.19 (m, 4H), 2.81-2.73 (m, 4H).

1938: White solid, yield: 88.5%. $^1$H NMR (400 MHz, CDCl$_3$) δ 9.74 (br, 1H), 7.75-7.00 (m, 15H), 6.60-6.43 (m, 3H), 5.10 (s, 2H), 3.74 (s, 2H), 3.30-3.05 (m, 4H), 2.81-2.61 (m, 4H).

1939: White solid, yield: 85.6%. $^1$H NMR (400 MHz, CDCl$_3$) δ 9.79 (br, 1H), 7.74-7.12 (m, 14H), 7.05-7.02 (m, 1H), 6.60-6.45 (m, 3H), 5.06 (s, 2H), 3.78 (s, 2H), 3.24-3.17 (m, 4H), 2.78-2.73 (m, 4H).

1940: White solid, yield: 86.5%. $^1$H NMR (400 MHz, CDCl$_3$) δ 9.54 (br, 1H), 7.66-7.58 (m, 2H), 7.52-6.89 (m, 13H), 6.61-6.41 (m, 3H), 5.02 (s, 2H), 3.79 (d, J=5.6 Hz, 2H), 3.32-3.21 (m, 4H), 2.83-2.72 (m, 4H).

1946: White solid, yield: 81.5%. $^1$H NMR (400 MHz, CDCl$_3$) δ 9.67 (br, 1H), 7.69-7.19 (m, 10H), 7.19-7.08 (m, 1H), 6.56-6.34 (m, 3H), 3.94 (t, J=6.5 Hz, 2H), 3.26-3.13 (m, 4H), 2.82-2.65 (m, 4H), 1.88-1.71 (m, 2H), 1.54-1.41 (m, 2H), 0.97 (t, J=7.4 Hz, 3H).

1949: White solid, yield: 66.7%. $^1$H NMR (400 MHz, CDCl$_3$) δ 9.70 (br, 1H), 7.69-7.19 (m, 10H), 7.17-7.12 (m, 1H), 6.54-6.37 (m, 3H), 3.82-3.72 (m, 4H), 3.25-3.12 (m, 4H), 2.76-2.66 (m, 4H), 1.32-1.19 (m, 1H), 0.73-0.58 (m, 2H), 0.37-0.30 (m, 2H).

Biological Results

To date, a series of crystal structures of KRAS mutants in complex with inhibitors revealed two binding pockets, which exist only when the inhibitors bind with KRAS: i) the switch II pocket for KRAS$^{12C}$-specific inhibitors, and ii) the allosteric site between the switch I and switch II that tends to produce pan-inhibitors of all RAS, such as BI-2852. We believe a novel binding-pocket is needed to identify selective inhibitors of the KRAS$^{12D}$ and KRAS$^{12V}$ mutants. As described herein above, dimerization of oncogenic KRAS mutants is essential for activation of KRAS signaling.[21] We thus hypothesized that therapeutic targeting of KRAS mutants in cancers could be achieved by compound-mediated disruption of KRAS dimer formations.

Example 1—Construction of the structural model of a novel binding-site at the dimerization interface of KRAS$^{12D}$: By computational simulations and homology modeling based on the crystal structure of KRAS$^{12D}$ (PDB: 4usj), we have constructed a structural model of a novel binding-site at the KRAS$^{12D}$ dimer interface (referred to as KRAS dimer-site).

Example 2—Development of BRET-based KRAS biosensor pairs for the measurement of KRAS dimerization and effector interaction: Based on recent work of Bery et al.,[23] we have generated BRET2 plasmid constructs for detecting dimerization of KRAS WT and mutants. pCMV-Rluc8 and pCMV-GFP2 were individually fused to the N-terminus of the KRAS WT, KRAS$^{12D}$, KRAS$^{12V}$ and c-RAF to generate biosensor pairs for detecting KRAS/KRAS dimerization or KRAS/cRAF interaction. For example, pCMV-Rluc8-KRAS$^{12D}$ and pCMV-GFP2-KRAS$^{12D}$ biosensor pair is for measurement of KRAS$^{12D}$ dimerization, whereas pCMV-Rluc8-KRAS$^{12D}$ and pCMV-GFP2-cRAF is for KRAS$^{12D}$/cRAF interaction. All constructs were verified by sequencing and Western blot analysis. BRET2 experiments were performed in HEK293 cells by transient transfection of Rluc8-KRAS plasmid together with GFP2-KRAS plasmid into cells, with a donor-only Rluc8-KRAS was used as the negative control. By increasing the ratio between Rluc8-KRAS construct and GFP2-KRAS construct, we have observed saturation of BRET signal for each KRAS sensor pairs, indicating the interactions are specific.

Example 3—Experimental details of BRET2 assays: For all BRET experiments in this work, HEK293 cells in one six-well plate were transiently transfected with KRAS biosensor pairs. 24 hours later, the cells were seeded in 96-well plates and exposed to vehicle control or compound for 24 hours. BRET signal was read immediately after adding DeepBlueC (Biotium). For WT KRAS, EGF (10 ng/mL) was added 30 minutes before adding DeepBlue C. The BRET ratio corresponds to the light emitted by the GFP2 acceptor constructs (510 nm) upon addition of DeepBlue C (5 µM) divided by the light emitted by the RLuc8 donor constructs (395 nm). The background signal was subtracted from that BRET ratio using the donor-only negative control, where only the RLuc8 plasmid plus the empty vector pCMV was transfected into the cells. Each experiment was performed in quadruplets and repeated at least twice.

Figure 2:
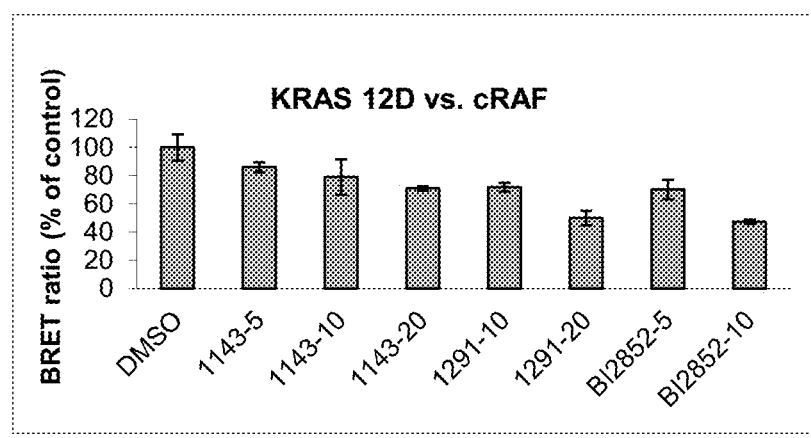
FIG. 2: BRET2 assays using KRAS biosensor pairs in HEK293 cells revealed that compounds 1143, 1291 and BI-2852 inhibit interaction of KRAS 12D with cRAF in a dose-dependent manner. Experimental details are described herein below. Cells were exposed to compound 1143 at 5, 10 or 20 μM or compound 1291 at 10, 20 μM for 24 hours. BI2852 (BI-2852) is a pan-inhibitor of RAS and was included as a positive control.

Example 4—Discovery of novel selective inhibitors of KRAS mutants: We have performed virtual screening of the chemical database of all chemical compounds that we have made in our laboratory against the KRAS dimer-site. The top-ranking compounds were then verified by BRET2 assays in HEK293 cells using KRAS biosensor pairs, as described above. We discovered that compounds 1093, 1101, 1121, 1177, 1141, 1143, 1181, 1291 and 1397 at 10 µM inhibit dimerization of KRAS 12D, 12V or 12C (FIG. 1). Importantly, 1121 and 1143 at 10 µM potently inhibited dimerization of KRAS$^{12D}$ and KRAS$^{12V}$, but were inactive against the WT KRAS dimerization (FIG. 1), indicating 1121 and 1143 are selective inhibitor of KRAS mutants. In contrast, 1093 and 1291 at 10 µM potently inhibited dimerization of the KRAS mutants and WT (FIG. 1). As BI-2852 is so far the most potent inhibitor of RAS/effector interaction,[17] BI-2852 was used as a reference compound in this work. Using Rluc8-KRAS$^{12D}$ and GFP2-cRAF biosensor pair, we demonstrated that 1143 and 1291 as well as BI-2852 inhibit KRAS$^{12D}$/cRAF interaction in a dose-dependent manner (FIG. 2).

Figure 3:
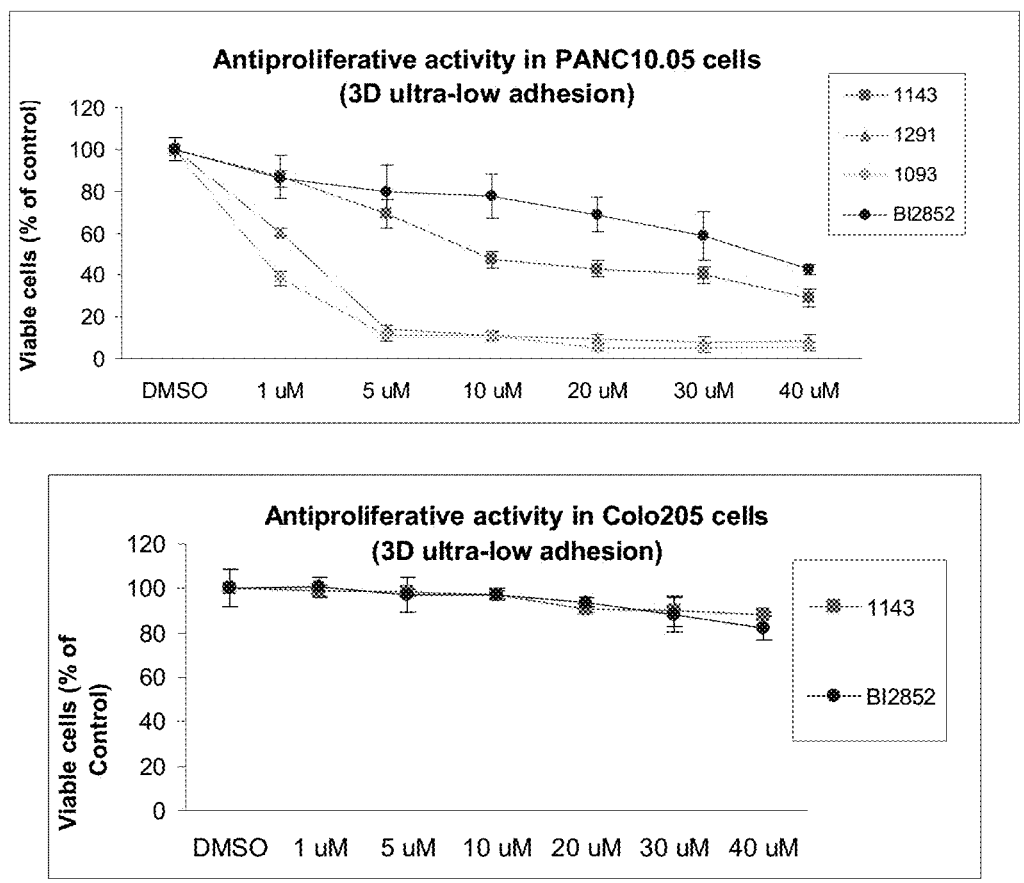
FIG. 3: Compounds 1093, 1143, 1291 and BI2852 show dose-dependent anti-proliferative effect in PANC 10.05 cells that express endogenous KRAS 12D. In particular, 1143 and BI2852 are inactive in BRAF V600E mutant Colo205 cells. Cells were seeded in ultra-low adhesion plates in medium with 2% FBS. Cells were exposed to compound at designated doses for 3 days. Viable cells were evaluated by CellTiter-Glo 3D assay (Promega). Experiments were in triplicate and repeated at least twice. Bars, standard deviation. BI2852 (BI-2852) is a pan-inhibitor of RAS and was included as a positive control.
Figure 4:
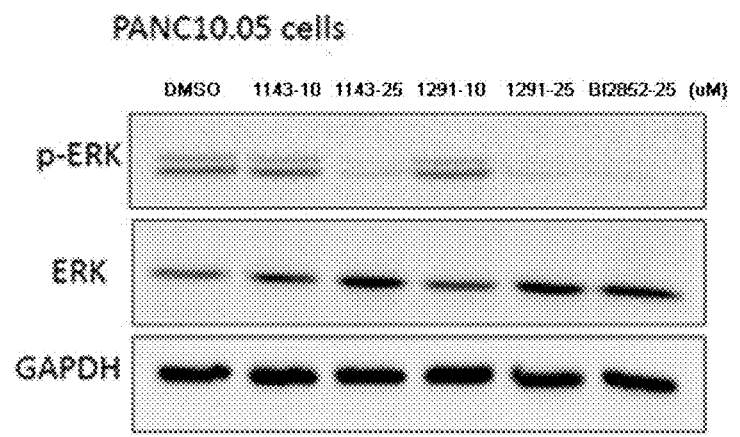
FIG. 4: Dose-dependent inhibition of compounds 1143 and 1291 on phosphorylation of ERK in PANC10.05 cells, as assessed by WB analysis. PANC10.05 cells in ultra-low adhesion 6-well plates in medium with 2% FBS were exposed to compounds for 18 hours. BI2852 (BI-2852) is a pan-inhibitor of RAS and was included as a positive control.

Example 5—Work done by others discovered that culture of KRAS mutant cells in the ultra-low adhesion plates could provide a model of 3-dimensional (3D) culture that reflects the KRAS dependency of cancer cells[24,25]. With this 3D culture system, we found that compounds 1093, 1143, 1291 and BI-2852 inhibit proliferation of PANC10.05 pancreatic cancer cell line that endogenously express the KRAS 12D mutant (FIG. 3). Importantly, compound 1143, like BI-2852, shows dose-dependent anti-proliferative effect in PANC10.05 cells, but not in the BRAF (V600E mutated) Colo205 cells that signal in KRAS-independent manner (FIG. 3).[17] The results suggest that 1143 is targeting KRAS itself. By Western blot analysis, we showed that 1143 and 1291 inhibit KRAS signaling in PANC10.05 cells (using CellTiter-Glo 3D assay) (FIG. 4).

Figure 5:
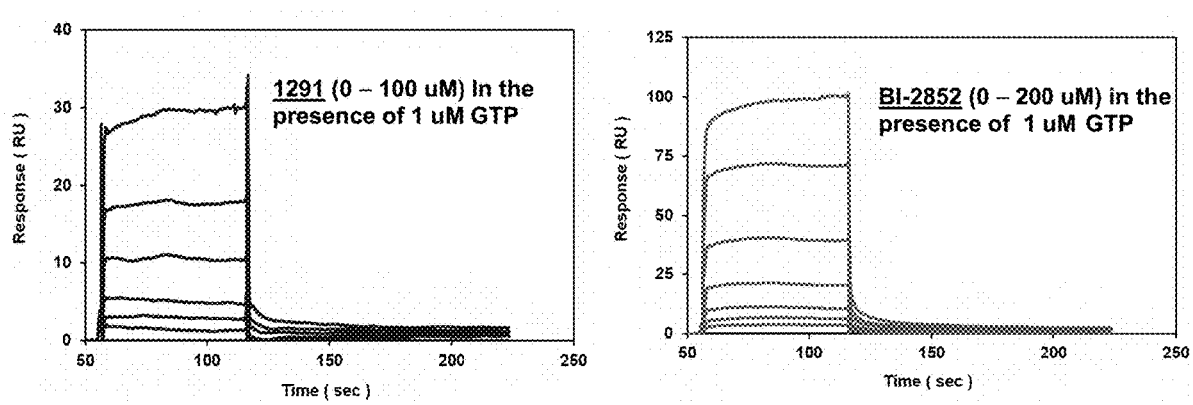
FIG. 5: Surface Plasmon Resonance (SPR) analysis (using Biacore T200) indicated direct and dose-dependent binding of compound 1291 (0-100 μM; 2-fold serial) or BI-2852 (0-200 μM; 2-fold serial) binding to 3500 RU amine-coupled KRAS(G12D) in the presence of 1 μM GTP. BI2852 (BI-2852) is a pan-inhibitor of RAS and was included as a positive control.

Example 6—To further verify direct binding of our compounds with KRAS mutant, we have performed Surface Plasmon Resonance (SPR) analysis, using recombinant KRAS$^{12D}$ mutant protein (TP700052, ORIGENE). With BI-2852 as a positive control, direct binding of 1291 with KRAS$^{12D}$ mutant was confirmed by our SPR analysis (FIG. 5).

Figure 6:
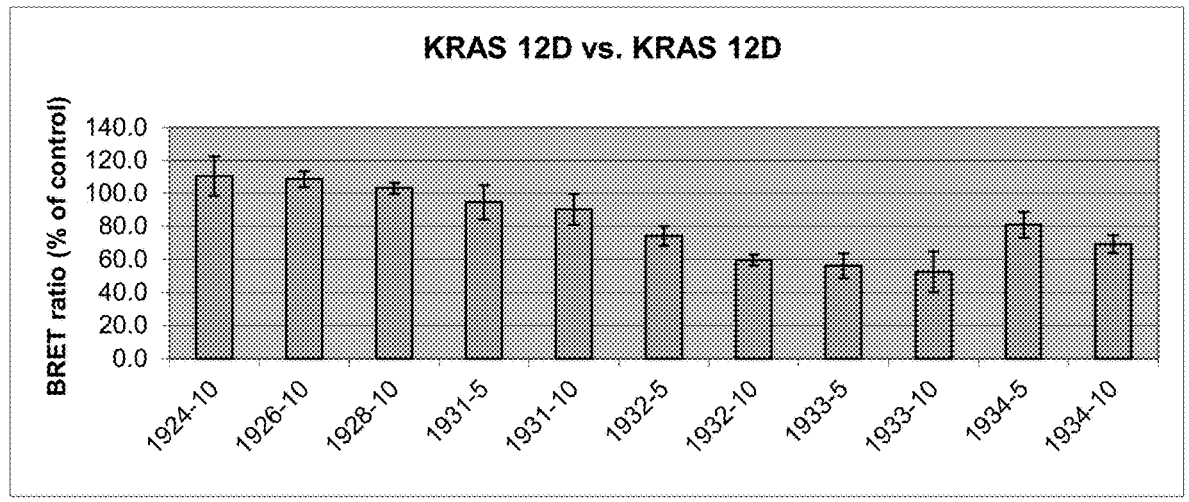
FIG. 6: Effect of compounds 1924, 1926, 1928, 1931, 1932, 1933 and 1934 on dimerization of KRAS 12D mutant, as assessed by BRET2 assays in HEK293 cells. Experimental details are described herein below. Cells were exposed to DMSO vehicle or the compound at designated doses (μM) for 24 hours.
Figure 7:
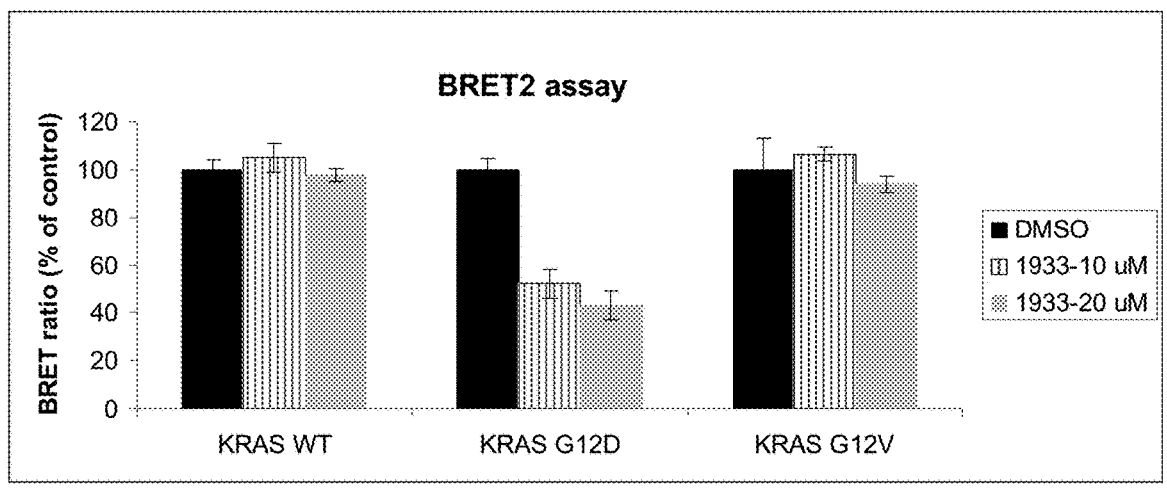
FIG. 7: BRET2 assays using KRAS biosensor pairs (KRAS 12D vs. 12D, KRAS 12V vs. 12V or KRAS WT vs. WT) revealed that compound 1933 is a selective inhibitor of KRAS 12D, which is inactive against the KRAS WT and KRAS 12V mutant. Experimental details are described herein below. Cells were exposed to DMSO vehicle or compound at designated doses (uM) for 24 hours.
Figure 8:
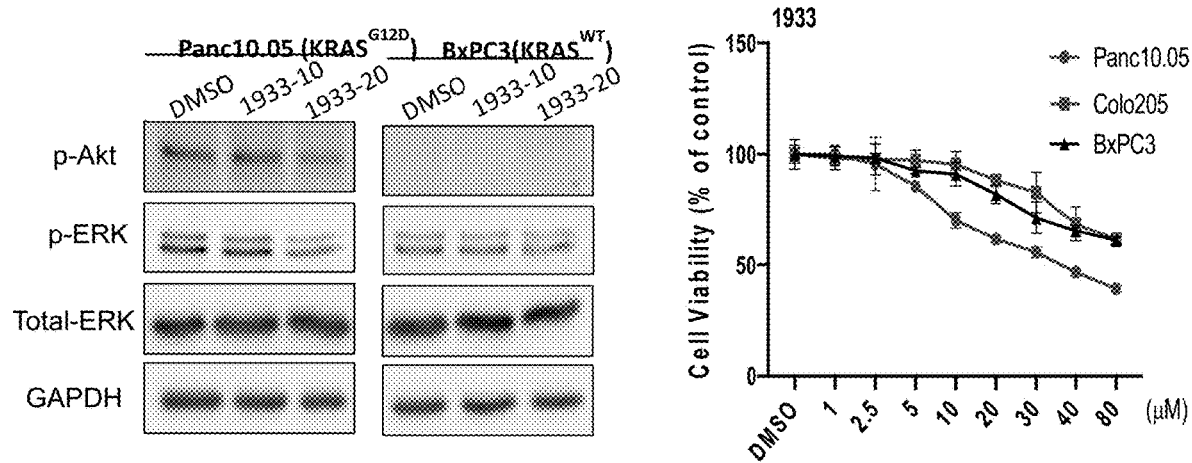
FIG. 8: Left) WB analysis: Compound 1933 dose-dependently inhibits phosphorylation of AKT and ERK in PANC10.05 cells that endogenously express KRAS 12D mutant. In contrast, 1933 is inactive against phosphorylation of ERK in BxPC3 cells that endogenously express WT KRAS. Cells in ultra-low adhesion 6-well plates in medium with 2% FBS were exposed to compounds for 6 hours; Right) Compound 1933 shows dose-dependent anti-proliferative effect in PANC 10.05 cells, and much less effect in Colo205 and BxPC3 cells. Cells were seeded in ultra-low adhesion plates in medium with 2% FBS and exposed to compound at designated doses for 5 days. Viable cells were evaluated by CellTiter-Glo 3D assay (Promega). Experiments were in triplicate and repeated at least twice. Bars, standard deviation.

Example 7—To further explore structure-activity relationship (SAR) and optimize activity of compound 1143, we have synthesized a series of novel 1143 analogues, as listed in Table 5. By BRET2 assay using KRAS 12D biosensor pair (FIG. 6), we showed that i) compounds 1924, 1926 and 1928 are inactive, indicating —$OCH_3$ substitution at the meta position of phenyl ring may be important for the activity of compound 1143; ii) Among these 1143 derivatives (compounds 1931-1934), compound 1933 with a bulky group at the meta position of phenyl ring is most potent in disrupting KRAS 12D dimerization (FIG. 6). We next showed that compound 1933 is a selective inhibitor of KRAS 12D that is inactive against the KRAS 12V or KRAS WT (FIG. 7). Compound 1933 inhibits KRAS signaling in PANC10.05 cells, but not in the BxPC3 cells that endogenously express WT KRAS (FIG. 8). By CellTiter-Glo 3D assay, we demonstrated that 1933 substantially inhibit proliferation of PANC10.05 cells in a dose-dependent manner. In contrast, 1933 is inactive against Colo205 and BxPC3 cells at 20 µM and showed minor activity at higher doses (FIG. 8).

Figure 9:
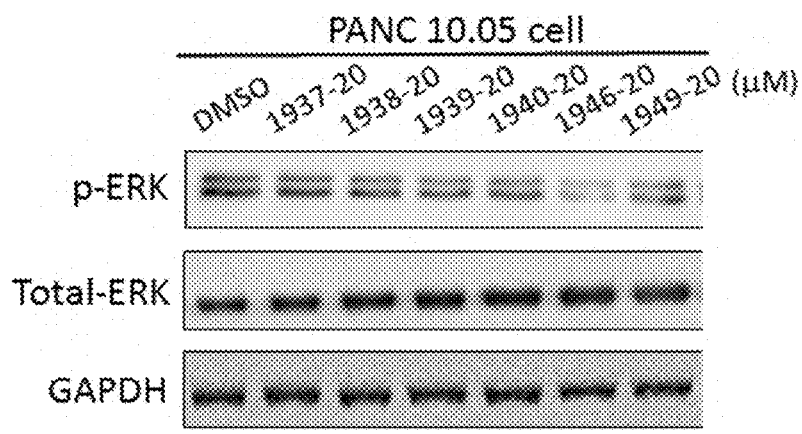
FIG. 9: Effect of compounds 1937, 1938, 1939, 1940, 1946 and 1949 at 20 μM on phosphorylation of ERK in PANC10.05 cells. Cells in ultra-low adhesion 6-well plates in medium with 2% FBS were exposed to compounds at designated doses for 6 hours.
Figure 10:
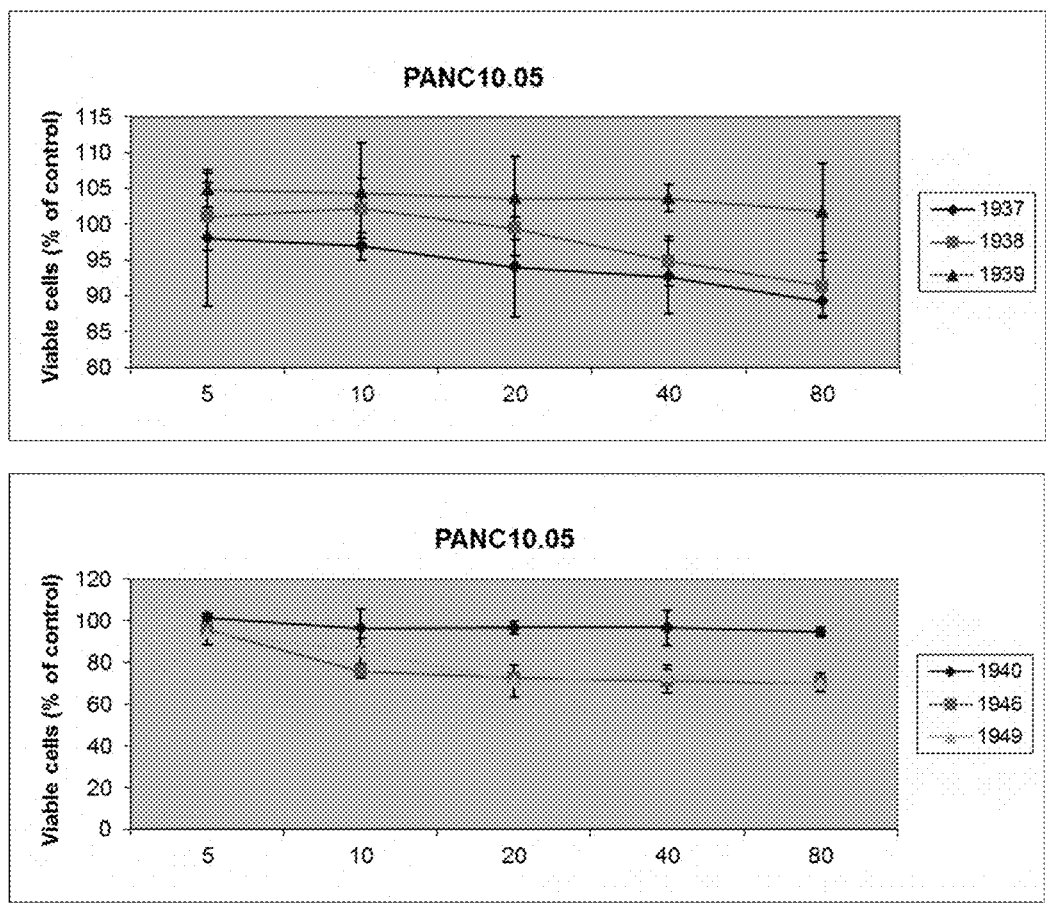
FIG. 10: Anti-proliferative effect of compounds 1937, 1938, 1939, 1940, 1946 and 1949 in PANC10.05 cells. Cells were seeded in ultra-low adhesion plates in medium with 2% FBS and exposed to compound at designated doses for 3 days. Viable cells were evaluated by resaruzin reduction assay.

Example 8—To explore effect of a bulky sidechain at the meta-position of phenyl, we have synthesized a series of 1933 analogues (1937-1940, 1946 and 1949), as listed in Table 5. Effect of these 1933 analogues against the KRAS signaling in PANC10.05 cells was shown in FIG. 9, as assessed by WB analysis. Effect of these 1933 analogues on the proliferation of PANC10.05, as assessed by resaruzin assay, was shown in FIG. 10.

Impact and novelty: To avoid the complex effector network downstream of the KRAS signaling[1,26], the best strategy is to attack the central hub, the KRAS itself. Discovery of potent KRAS$^{12C}$-specific inhibitors is a major step toward this direction, but these KRAS$^{12C}$-specific inhibitors are inactive against the KRAS$^{12D}$ and KRAS$^{12V}$ as they do not have cysteine in residue 12 to form a covalent bond. The promising Phase I clinical trial of AMG-510, a KRAS$^{12C}$-specific inhibitor, indicated that KRAS mutant is druggable after all.[14] The major challenge in the field is how to discover selective inhibitors of the KRAS$^{12D}$ and KRAS$^{12V}$. The novelty of our work may be described as being threefold: i) We have discovered an entirely new binding-site at the KRAS dimer interface that could be used for identification of selective inhibitors of the KRAS$^{12D}$ and KRAS$^{12V}$; ii) We demonstrated that it is possible to disrupt KRAS dimerization by chemical compounds and inhibit KRAS signaling; and iii) We demonstrated that it is feasible to selectively inhibit KRAS$^{12D}$ and KRAS$^{12V}$ mutants vs. the WT KRAS. The compounds of the invention may be used as therapeutics for KRAS-driven cancers, such as pancreatic cancer, colorectal cancer and lung cancer.

Although the present invention has been described hereinabove by way of specific embodiments thereof, it may be modified, without departing from the spirit and nature of the subject invention as defined in the appended claims.

The present description refers to a number of documents, the content of which is herein incorporated by reference in their entirety.

REFERENCES

1. Cox A D, Fesik S W, Kimmelman A C, Luo J, Der C J. Drugging the undruggable RAS: Mission possible? Nat Rev Drug Discov 2014; 13:828-51.
2. Collins M A, Bednar F, Zhang Y, et al. Oncogenic Kras is required for both the initiation and maintenance of pancreatic cancer in mice. J Clin Invest 2012; 122:639-53.
3. Kanda M, Matthaei H, Wu J, et al. Presence of somatic mutations in most early-stage pancreatic intraepithelial neoplasia. Gastroenterology 2012; 142:730-3 e9.
4. Zorde Khvalevsky E, Gabai R, Rachmut I H, et al. Mutant KRAS is a druggable target for pancreatic cancer. Proc Natl Acad Sci USA 2013; 110:20723-8.
5. McCormick F. KRAS as a Therapeutic Target. Clin Cancer Res 2015; 21:1797-801.
6. Collins M A, Pasca di Magliano M. Kras as a key oncogene and therapeutic target in pancreatic cancer. Front Physiol 2013; 4:407.
7. Ryan D P, Hong T S, Bardeesy N. Pancreatic adenocarcinoma. N Engl J Med 2014; 371:1039-49.
8. Garrido-Laguna I, Hidalgo M. Pancreatic cancer: from state-of-the-art treatments to promising novel therapies. Nat Rev Clin Oncol 2015; 12:319-34.
9. Eser S, Schnieke A, Schneider G, Saur D. Oncogenic KRAS signalling in pancreatic cancer. Br J Cancer 2014; 111:817-22.
10. Jones R P, Sutton P A, Evans J P, et al. Specific mutations in KRAS codon 12 are associated with worse overall survival in patients with advanced and recurrent colorectal cancer. Br J Cancer 2017; 116:923-9.
11. Boutin A T, Liao W T, Wang M, et al. Oncogenic Kras drives invasion and maintains metastases in colorectal cancer. Genes Dev 2017; 31:370-82.
12. Ostrem J M, Peters U, Sos M L, Wells J A, Shokat K M. K-Ras(G12C) inhibitors allosterically control GTP affinity and effector interactions. Nature 2013; 503:548-51.
13. Lito P, Solomon M, Li LS, Hansen R, Rosen N. Allele-specific inhibitors inactivate mutant KRAS G12C by a trapping mechanism. Science 2016; 351:604-8.
14. AMG 510 First to Inhibit "Undruggable" KRAS. Cancer Discov 2019; 9:988-9.
15. Cox A D, Der C J, Philips M R. Targeting RAS Membrane Association: Back to the Future for Anti-RAS Drug Discovery? Clin Cancer Res 2015; 21:1819-27.
16. Samatar A A, Poulikakos P I. Targeting RAS-ERK signalling in cancer: promises and challenges. Nat Rev Drug Discov 2014; 13:928-42.
17. Kessler D, Gmachl M, Mantoulidis A, et al. Drugging an undruggable pocket on KRAS. Proc Natl Acad Sci USA 2019; 116:15823-9.
18. Zhou B, Der C J, Cox A D. The role of wild type RAS isoforms in cancer. Semin Cell Dev Biol 2016; 58:60-9.
19. Nussinov R, Tsai C J, Jang H. Is Nanoclustering essential for all oncogenic KRas pathways? Can it explain why wild-type KRas can inhibit its oncogenic variant? Semin Cancer Biol 2019; 54:114-20.
20. Chen M, Peters A, Huang T, Nan X. Ras Dimer Formation as a New Signaling Mechanism and Potential Cancer Therapeutic Target. Mini Rev Med Chem 2016; 16:391-403.
21. Ambrogio C, Kohler J, Zhou Z W, et al. KRAS Dimerization Impacts MEK Inhibitor Sensitivity and Oncogenic Activity of Mutant KRAS. Cell 2018; 172:857-68 e15.

22. Spencer-Smith R, Koide A, Zhou Y, et al. Inhibition of RAS function through targeting an allosteric regulatory site. Nat Chem Biol 2017; 13:62-8.
23. Bery N, Cruz-Migoni A, Bataille C J, et al. BRET-based RAS biosensors that show a novel small molecule is an inhibitor of RAS-effector protein-protein interactions. Elife 2018; 7.
24. Janes M R, Zhang J, Li L S, et al. Targeting KRAS Mutant Cancers with a Covalent G12C-Specific Inhibitor. Cell 2018; 172:578-89 e17.
25. Patricelli M P, Janes M R, Li L S, et al. Selective Inhibition of Oncogenic KRAS Output with Small Molecules Targeting the Inactive State. Cancer Discov 2016; 6:316-29.
26. Morkel M, Riemer P, Blaker H, Sers C. Similar but different: distinct roles for KRAS and BRAF oncogenes in colorectal cancer development and therapy resistance. Oncotarget 2015; 6:20785-800.
27. Meanwell, N. A. et al. J. Med. Chem. 1993, 36, 3884-3903.
28. Meanwell, N. A.; Rosenfeld, M. J.; Trehan, A. K. Wright, J. J. K.; Brassard, C. L.; Buchanan, J.; Federici, M. E.; Fleming, J. S.; Gamberdella, M.; Zavoico, G. B.; Seiler, S. M. J. Med. Chem. 1992, 35, 3483-3497.

The invention claimed is:

1. A compound of formula A:

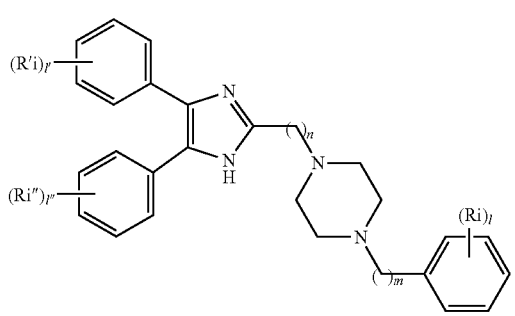

or a pharmaceutically acceptable salt thereof,
wherein:
Ri is halogen, CN, $NO_2$, alkyl, haloalkyl, $NH_2$, OH, O(alkyl), O(haloalkyl), O(alkylaryl), O(aryl), O(thioaryl), O(thioalkylaryl), SH, S(alkyl), S(haloalkyl), cycloalkyl, or aryl;
Ri' is halogen, CN, $NO_2$, alkyl, haloalkyl, $NH_2$, OH, O(alkyl), O(haloalkyl), O(alkylaryl), O(aryl), O(thioaryl), O(thioalkylaryl), SH, S(alkyl), S(haloalkyl), cycloalkyl, or aryl;
Ri" is halogen, CN, $NO_2$, alkyl, haloalkyl, $NH_2$, OH, O(alkyl), O(haloalkyl), O(alkylaryl), O(aryl), O(thioaryl), O(thioalkylaryl), SH, S(alkyl), S(haloalkyl), cycloalkyl, or aryl;
l is 0 or 1;
l' is 0 or 1;
l" is 0 or 1;
m is 0 or 1; and
n is 1, 2, 3, 4, 5, or 6.

2. The compound according to claim 1, wherein the compound is of formula A1:

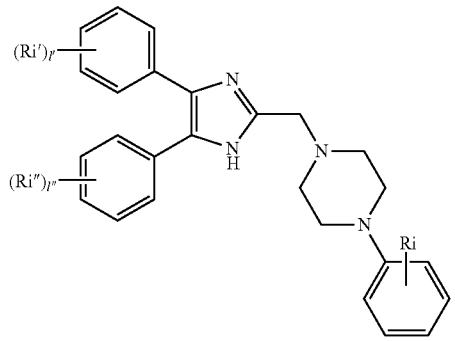

or a pharmaceutically acceptable salt thereof,
wherein:
Ri' is halogen;
Ri" is halogen;
l' is 0 or 1; and
l" is 0 or 1.

3. The compound according to claim 1, wherein the compound is selected from the group consisting of:

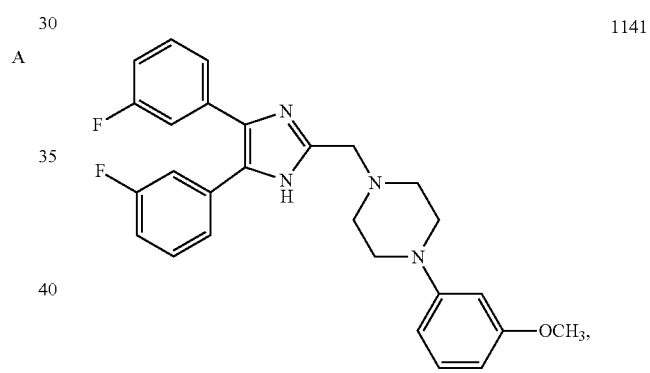

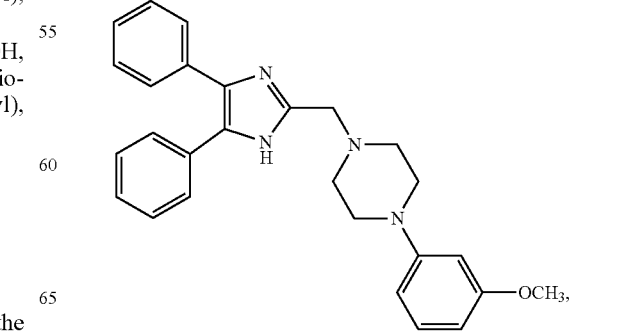

1181
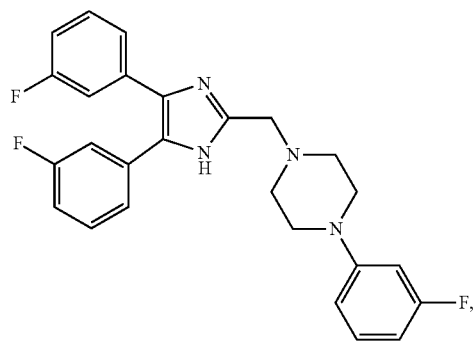
1314
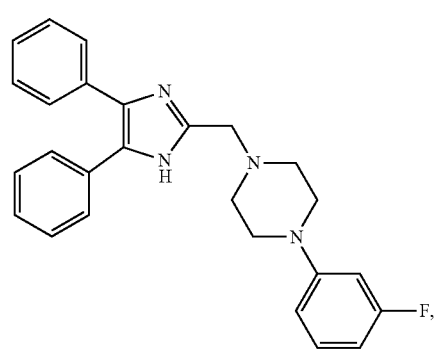
1924
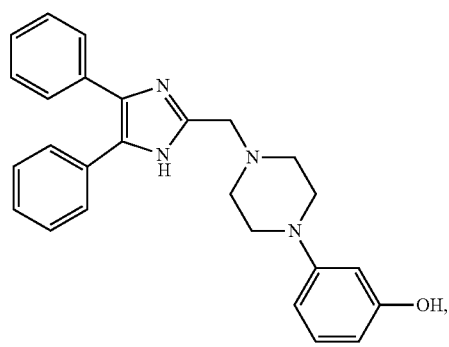
1926
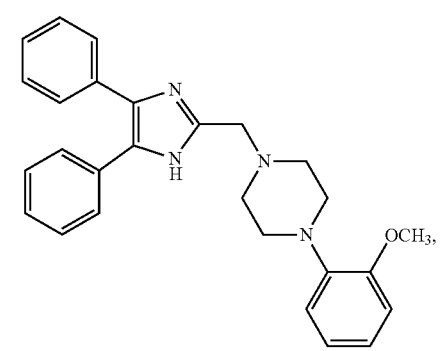
1928
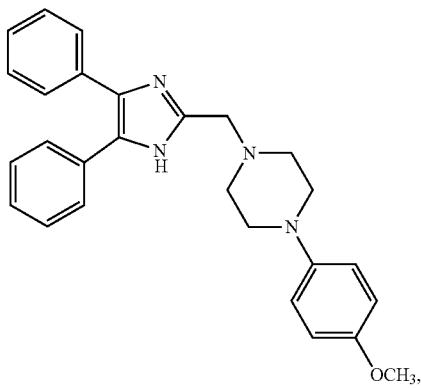
1931
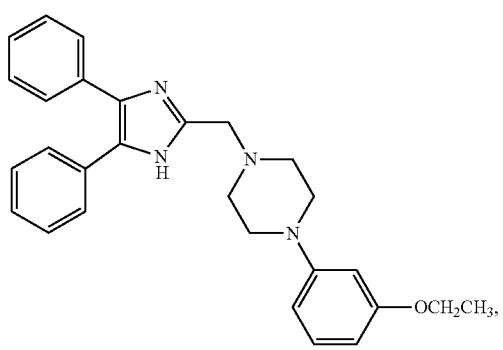
1934
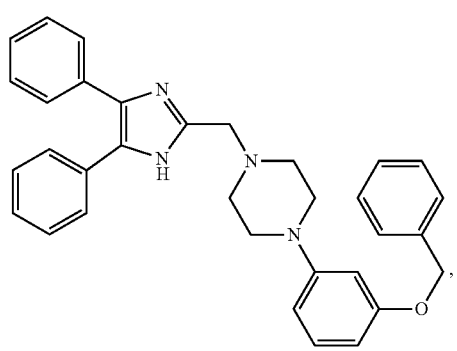
1937
, and -continued

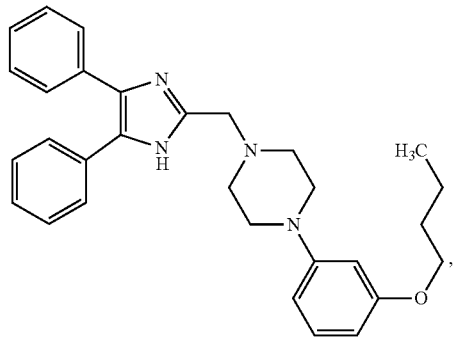
1946

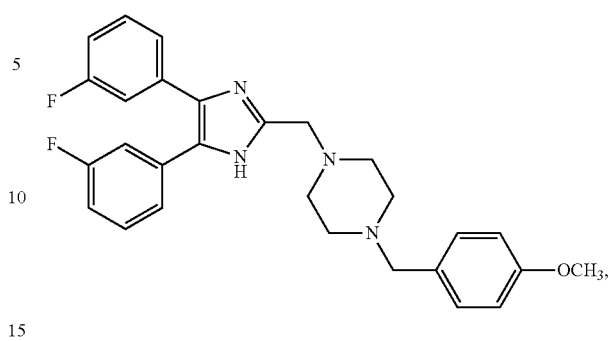
1291 or a pharmaceutically acceptable salt thereof.

4. The compound according to claim 1, wherein the compound is selected from the group consisting of:

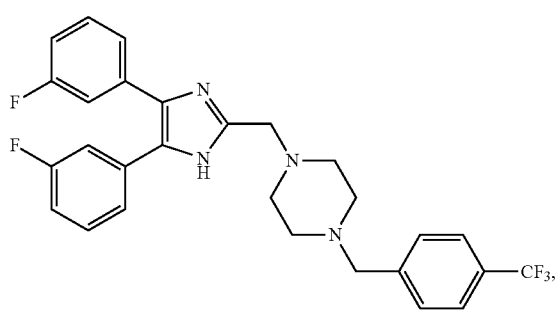
1093

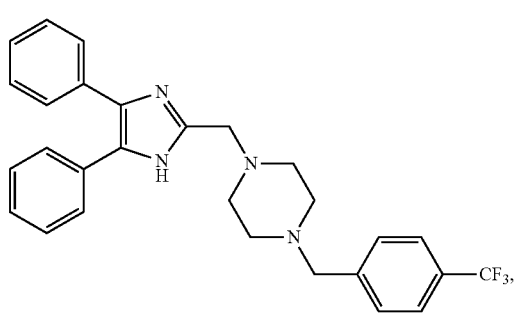
1101

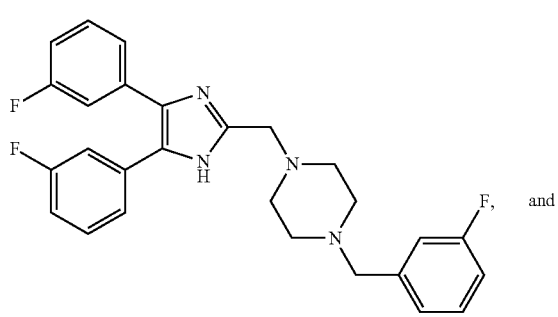
1290 or a pharmaceutically acceptable salt thereof.

5. A pharmaceutical composition comprising a compound according to claim 1, or a pharmaceutically acceptable salt thereof, and a pharmaceutically acceptable carrier.

6. A method for inhibiting a KRAS mutant in a subject, wherein the method comprises administering to the subject in need thereof a therapeutically effective amount of a compound according to claim 1, or a pharmaceutically acceptable salt thereof, or the pharmaceutical composition according to claim 5.

7. The method according to claim 6, wherein the KRAS mutant is selected from the group consisting of G12C, G12D, and G12V, or a combination thereof.

8. The method according to claim 6, wherein the subject is an animal.

9. The method according to claim 8, wherein the animal is a human.

10. The method according to claim 6, wherein the subject has a KRAS-driven cancer.

11. The method according to claim 10, wherein the KRAS-driven cancer is selected from the group consisting of a metastatic KRAS-driven cancer, a multi-drug resistant KRAS-driven cancer, a primary KRAS-driven cancer, a recurrent KRAS-driven cancer, or a combination thereof.

12. The method according to claim 10, wherein the KRAS-driven cancer is selected from the group consisting of colorectal cancer, lung cancer, and pancreatic cancer.

13. The method according to claim 10, wherein the method further comprises administering to the subject in need thereof a therapeutically effective amount of a second cancer therapy.

14. The method according to claim 6, wherein the therapeutically effective amount of the compound, or a pharmaceutically acceptable salt thereof, or the therapeutically effective amount of the pharmaceutical composition, is administered to the subject in need thereof intraarterially, intramuscularly, intranasally, intraocularly, intravenously, orally, subcutaneously, topically, and transdermally.

15. A method for selectively inhibiting KRAS G12D and/or KRAS G12V over wild-type KRAS in a subject, wherein the method comprises administering to a subject in need thereof a therapeutically effective amount of a compound according to claim 1, or a pharmaceutically acceptable salt thereof, or the pharmaceutical composition according to claim 5.

16. A compound of formula B:

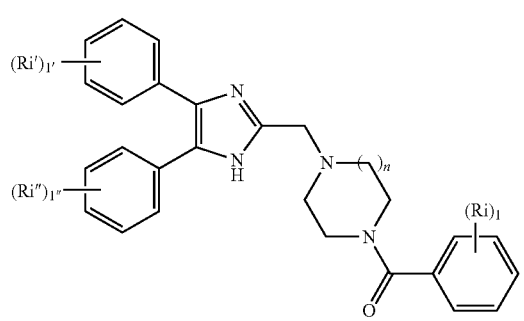

or a pharmaceutically acceptable salt thereof,
wherein:
Ri is halogen, CN, NO$_2$, alkyl, haloalkyl, NH$_2$, OH, O(alkyl), O(haloalkyl), O(alkylaryl), O(aryl), O(thioaryl), O(thioalkylaryl), SH, S(alkyl), S(haloalkyl), cycloalkyl, or aryl;

Ri' is halogen, CN, NO$_2$, alkyl, haloalkyl, NH$_2$, OH, O(alkyl), O(haloalkyl), O(alkylaryl), O(aryl), O(thioaryl), O(thioalkylaryl), SH, S(alkyl), S(haloalkyl), cycloalkyl, or aryl;

Ri" is halogen, CN, NO$_2$, alkyl, haloalkyl, NH$_2$, OH, O(alkyl), O(haloalkyl), O(alkylaryl), O(aryl), O(thioaryl), O(thioalkylaryl), SH, S(alkyl), S(haloalkyl), cycloalkyl, or aryl;

l is 0 or 1;
l' is 0 or 1;
l" is 0 or 1;
m is 0 or 1; and
n is 1, 2, 3, 4, 5, or 6.

17. The compound according to claim 16, wherein the compound is of formula B1:

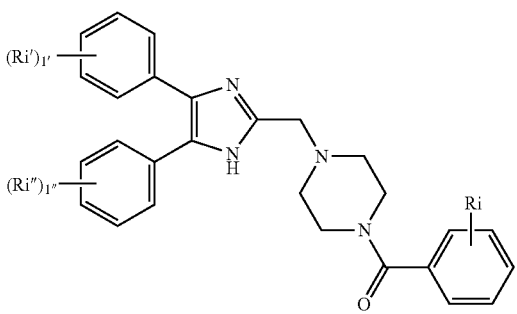

or a pharmaceutically acceptable salt thereof,
wherein:
Ri' is halogen;
Ri" is halogen;
l' is 0 or 1; and
l" is 0 or 1.

18. The compound according to claim 16, wherein the compound is selected from the group consisting of:

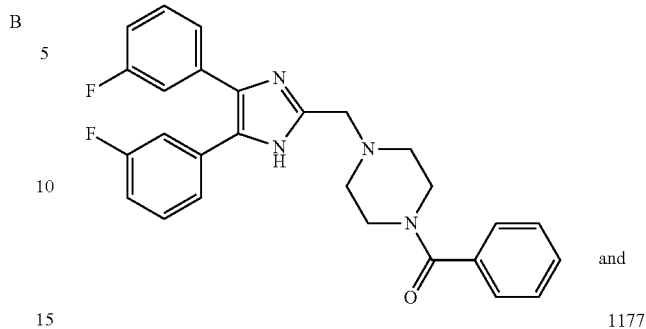

or a pharmaceutically acceptable salt thereof.

19. A pharmaceutical composition comprising a compound according to claim 16, or a pharmaceutically acceptable salt thereof, and a pharmaceutically acceptable carrier.

20. A method for inhibiting a KRAS mutant in a subject, wherein the method comprises administering to the subject in need thereof a therapeutically effective amount of a compound according to claim 16, or a pharmaceutically acceptable salt thereof, or the pharmaceutical composition according to claim 19.

21. The method according to claim 20, wherein the KRAS mutant is selected from the group consisting of G12C, G12D, and G12V, or a combination thereof.

22. The method according to claim 20, wherein the subject is an animal.

23. The method according to claim 22, wherein the animal is a human.

24. The method according to claim 20, wherein the subject has a KRAS-driven cancer.

25. The method according to claim 24, wherein the KRAS-driven cancer is selected from the group consisting of a metastatic KRAS-driven cancer, a multi-drug resistant KRAS-driven cancer, a primary KRAS-driven cancer, a recurrent KRAS-driven cancer, or a combination thereof.

26. The method according to claim 24, wherein the KRAS-driven cancer is selected from the group consisting of colorectal cancer, lung cancer, and pancreatic cancer.

27. The method according to claim 24, wherein the method further comprises administering to the subject in need thereof a therapeutically effective amount of a second cancer therapy.

28. The method according to claim 20, wherein the therapeutically effective amount of the compound, or a pharmaceutically acceptable salt thereof, or the therapeutically effective amount of the pharmaceutical composition, is administered to the subject in need thereof intraarterially, intramuscularly, intranasally, intraocularly, intravenously, orally, subcutaneously, topically, and transdermally.

29. A method for selectively inhibiting KRAS G12D and/or KRAS G12V over wild-type KRAS in a subject, wherein the method comprises administering to a subject in need thereof a therapeutically effective amount of a compound according to claim 16, or a pharmaceutically acceptable salt thereof, or the pharmaceutical composition according to claim 19.

30. A compound selected from the group consisting of:

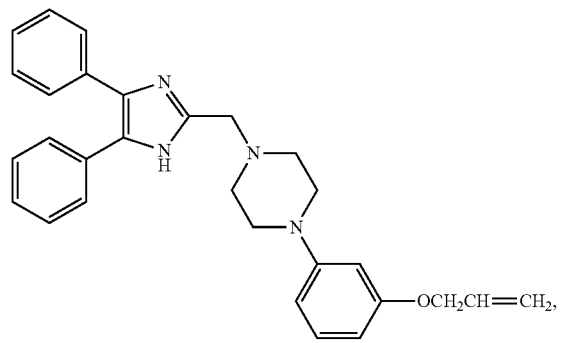

1932

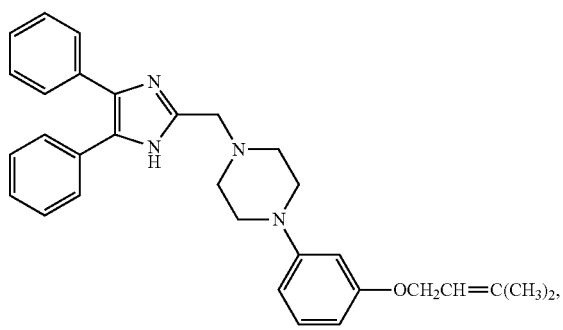

1933

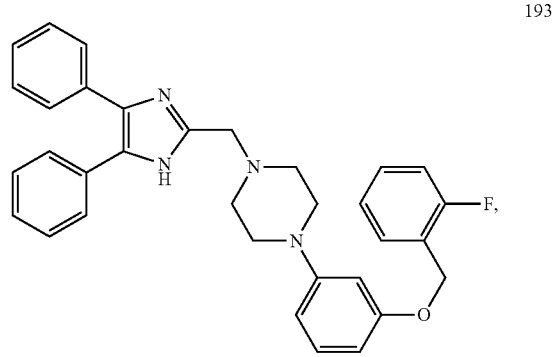

1938

-continued

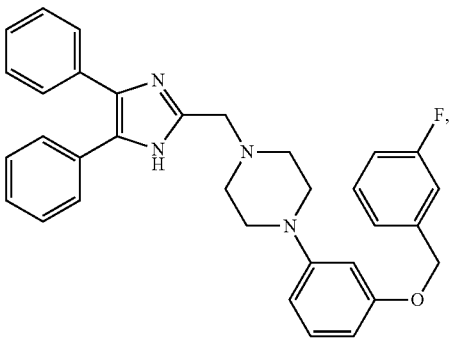

1939

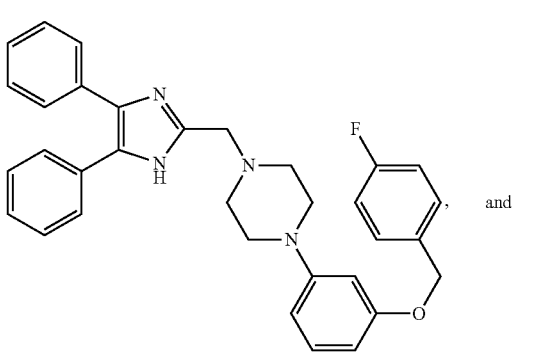

1940

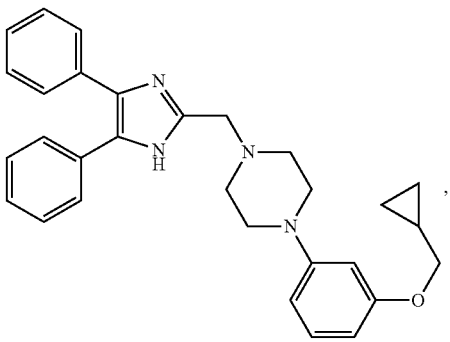

1949 or a pharmaceutically acceptable salt thereof.

* * * * *

UNITED STATES PATENT AND TRADEMARK OFFICE
CERTIFICATE OF CORRECTION

PATENT NO.       : 11,434,231 B2
APPLICATION NO.  : 16/924157
DATED            : September 6, 2022
INVENTOR(S)      : Xiaohong Tian, Jian Hui Wu and Qianhui Yi It is certified that error appears in the above-identified patent and that said Letters Patent is hereby corrected as shown below:

On the Title Page

Item (73) Assignee: "THE ROYAL INSTITUTION FOR THE ADCANCEMENT OF LEARN" should read --THE ROYAL INSTITUTION FOR THE ADVANCEMENT OF LEARNING/McGILL UNIVERSITY--

Signed and Sealed this
Fourteenth Day of November, 2023

Katherine Kelly Vidal
*Director of the United States Patent and Trademark Office*